United States Patent
Copeland et al.

(10) Patent No.: US 6,844,318 B2
(45) Date of Patent: Jan. 18, 2005

(54) PEPTIDASE-CLEAVABLE, TARGETED ANTINEOPLASTIC DRUGS AND THEIR THERAPEUTIC USE

(75) Inventors: Robert A. Copeland, Hockessin, DE (US); Charles F. Albright, West Chester, PA (US); Andrew P. Combs, Kennett Square, PA (US); Randine L. Dowling, Wilmington, DE (US); Nilsa R. Graciani, Wilmington, DE (US); Wei Han, Newark, DE (US); C. Anne Higley, Newark, DE (US); Pearl S. Huang, Lansdale, PA (US); Eddy W. Yue, Landenberg, PA (US); Susan V. DiMeo, Wilmington, DE (US)

(73) Assignee: Bristol Myers Squibb Pharma Company, Princeton, NJ (US)

(*) Notice: Subject to any disclaimer, the term of this patent is extended or adjusted under 35 U.S.C. 154(b) by 0 days.

(21) Appl. No.: 09/808,832

(22) Filed: Mar. 15, 2001

(65) Prior Publication Data

US 2002/0103133 A1 Aug. 1, 2002

Related U.S. Application Data

(60) Provisional application No. 60/189,387, filed on Mar. 15, 2000.

(51) Int. Cl.$^7$ .................... A61K 38/07; A61K 38/08; A61K 38/14; A61K 31/704
(52) U.S. Cl. ................ 514/8; 514/16; 514/17; 514/18; 514/34; 530/322; 530/328; 530/329; 530/330; 536/6.4
(58) Field of Search .................. 514/8, 16, 17, 514/18, 34; 530/322, 328, 329, 330; 536/6.4

(56) References Cited

U.S. PATENT DOCUMENTS

| | | | | |
|---|---|---|---|---|
| 4,703,107 A | | 10/1987 | Monsigny et al. | 530/330 |
| 5,853,713 A | * | 12/1998 | Cooper et al. | 424/78.38 |
| 5,962,216 A | | 10/1999 | Trouet et al. | 435/4 |
| 6,303,569 B1 | * | 10/2001 | Greenwald et al. | 514/2 |
| 6,342,480 B1 | | 1/2002 | Trouet et al. | 514/18 |
| 2002/0147138 A1 | * | 10/2002 | Firestone et al. | 514/8 |

FOREIGN PATENT DOCUMENTS

| | | |
|---|---|---|
| EP | 126685 | 11/1984 |
| EP | 359347 | 3/1990 |
| GB | 2131813 | 6/1984 |
| WO | WO 9600503 | 1/1996 |
| WO | WO 9605863 | 2/1996 |
| WO | WO 9712624 | 4/1997 |
| WO | WO 9714416 | 4/1997 |
| WO | WO 9748725 | 12/1997 |
| WO | WO 9810651 | 3/1998 |
| WO | WO 9810795 | 3/1998 |
| WO | WO 9816240 | 4/1998 |
| WO | WO 9818493 | 5/1998 |
| WO | WO 9846250 | 10/1998 |
| WO | WO 9902175 | 1/1999 |
| WO | WO 0033888 | 6/2000 |
| WO | WO 0059930 | 10/2000 |
| WO | WO 0064486 | 11/2000 |
| WO | WO 0071571 | 11/2000 |

OTHER PUBLICATIONS

Bassiouny et al. Flow Regulation of 72–kD Collagenase IV (MMP–2) After Experimental Aterial Injury. Circulation. vol. 98, pp. 157–163 (1998).*

Timar et al, "The antiproliferative action of a melphalan hexapeptide with collagenase–cleavable site" Cancer Chemotherapy Pharmacology, vol. 41, No. 4, 1998, 292–298.

Masquelier et al, "Amino Acid and Dipeptide Derivatives of Daunorubicin. 1. Synthesis, Physicochemical Properties, and Lysosomal Digestion", Journal of Medicinal Chemistry, American Chemical Society, vol. 23, No. 11, 1980, 1166–1170.

Denmeade et al, "Enzymatic Activation of a Doxorubicin–Peptide Prodrug by Prostate–Specific Antigen", Cancer Research, American Assoc. for Cancer Research, vol. 58, Jun. 15, 1998, 2537–2540.

Safavy et al, "Paclitaxel Derivatives for Targeted Therapy of Caner: Toward the Development of Smart Taxanes" Journal of Medicinal Chemistry, Am. Chem. Soc., vol. 42, 1999, 4919–4924.

McGeehan et al, "Characterization of the Peptide Substrate Specificities of Interstitial Collagenase and 92–KDA Gelatinase Implications of Substrate Optimization" Journal of Biological Chem., vol. 269, No. 52, Dec. 30, 1994, 32814–32820.

Aimes et al, Matrix Metalloproteinase–2 Is an Interstital Collagenase, Journal of Biological Chemistry, vol. 270, No. 11, Mar. 17, 5872–5876, 1995.

Kurschat et al, Tissue Inhibitor or Matrix Metalloproteinase–2 Regulates Matrix Metalloproteinase–2 Activation by Modulation of Membrane–type 1 Matrix Metalloproteinase Activity in High and Low Invasive Melanoma Cell Lines, Journal of Biological Chemistry, vol. 274, No. 30, 21056–21062, 1999.

Garbisa et al, Correlation of Serum Metalloproteinase Levels with Lung Cancer Metastasis and Response to Therapy, Cancer Research, 52, 4548–4549, 1992.

(List continued on next page.)

Primary Examiner—Jeffrey Edwin Russel
(74) Attorney, Agent, or Firm—Elliot Korsen

(57) ABSTRACT

This invention is directed to antineoplastic agents conjugated to enzyme-cleavable peptides comprising the amino acid recognition sequence of a membrane-bound and/or cell-secreted peptidase, and to the use of such conjugated compounds as chemotherapeutic agents in the targeted treatment of cancers.

37 Claims, No Drawings

OTHER PUBLICATIONS

Boven et al, Doxorubicin Compared with Related Compounds in a Nude Mouse Model for Human Ovarian Cancer, Eur. J. Cancer, vol. 26, No. 9, 983–986, 1990.

Knauper et al, Biochemical Characterization of Human Collagenase-3, Biological Chemistry, vol. 271, No. 3, 1544–1550, 1996.

Brooks et al, Localization of Matrix Metalloproteinase MMP-2 to the Surface of Invasive Cells by Interation with Integrin αvβ3, Cell, vol. 85, 683–693, 1996.

Moses et al, Increased Incidence of Matrix Metalloproteinases in Urine of Cancer Patients, Cancer Research, 58, 1395–1399, 1998.

Canal et al, Human pharmacokinetics of N–L–leucyl–doxorubicin, a new anthracycline derivative, and its correlation with clinical toxicities, Clin. Pharmacol. Ther., vol. 51, No. 3, 249–259, 1992.

Boven et al, The anti–tumour effects of the prodrugs N–I–leucyl–doxorubicin and vinblastine–isoleucinate in human ovarian cancer xenografts, Br. J. Cancer, 66, 1044–1047, 1992.

McDonnell et al, Role of matrix metalloproteinases in invasion and metastasis: biology, diagnosis and inhibitors, Cytotechnology, 12, 367–384, 1993.

Brummer et al, Matrix–metalloproteinases 1, 2 and 3 and their tissue inhibitors 1 and 2 in benign and malignant breast lesions: an in situ hybridization study, Virchows Arch, 435, 566–573, 1999.

MacDougall et al, Contributions of tumor and stromal matrix metalloproteinases to tumor progression, invasion and metastasis, Cancer and Metastasis Reviews, 14, 351–362, 1995.

De Jong et al, Plasma Pharmacokinetics and Pharmacodynamics of a New Prodrug N–I–Leucyldoxorubicin and Its Metabolities in a Phase I Clinical Trail, Journal of Clinical Oncology, vol. 10, No. 12, 1897–1906, 1992.

De Groot et al, Synthesis and Biological Evaluation of Novel Prodrugs of Anthracyclines for Selective Activation by the Tumor–Associated Protease Plasmin, J. Med. Chem., 42, 5277–5283, 1999.

Nagase et al, Human Matrix Metalloproteinase Specificity Studies Using Collagen Sequence–Based Synthetic Peptides, Biopolymers, vol. 40, 399–416, 1996.

Whittaker et al, Design and Therapeutic Application of Matrix Metalloproteinase Inhibitors, Chem. Rev. 99, 2735–2776, 1999.

* cited by examiner

__US 6,844,318 B2__

```
                          SEQUENCE LISTING

<160> NUMBER OF SEQ ID NOS: 240

<210> SEQ ID NO 1
<211> LENGTH: 5
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = 4-methoxy-benzenesulfonyl-beta-
      alanine
<220> FEATURE:
<221> NAME/KEY: MISC_FEATURE
<222> LOCATION: (3)..(3)
<223> OTHER INFORMATION: wherein Xaa = homophenylalanine

<400> SEQUENCE: 1

Xaa Gly Xaa Tyr Leu
1               5

<210> SEQ ID NO 2
<211> LENGTH: 5
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = 1, 2-C6H4 (CO) 2-histidine
<220> FEATURE:
<221> NAME/KEY: MISC_FEATURE
<222> LOCATION: (3)..(3)
<223> OTHER INFORMATION: wherein Xaa = homophenylalanine

<400> SEQUENCE: 2

Xaa Gly Xaa Tyr Leu
1               5
```

<210> SEQ ID NO 3
<211> LENGTH: 5
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-proline

<400> SEQUENCE: 3

Xaa Leu Gly Leu Leu
1               5

<210> SEQ ID NO 4
<211> LENGTH: 5
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<220> FEATURE:
<221> NAME/KEY: MISC_FEATURE
<222> LOCATION: (1)..(1)
<223> OTHER INFORMATION: wherein Xaa = acetyl-proline

<400> SEQUENCE: 4

Xaa Leu Gly Leu Leu
1               5

<210> SEQ ID NO 5
<211> LENGTH: 5
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl proline
<220> FEATURE:
<221> NAME/KEY: MISC_FEATURE
<222> LOCATION: (2)..(2)
<223> OTHER INFORMATION: wherein Xaa = beta alanine

<400> SEQUENCE: 5

Xaa Xaa Gly Leu Leu
1               5

<210> SEQ ID NO 6
<211> LENGTH: 5
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-proline
<220> FEATURE:
<221> NAME/KEY: MISC_FEATURE
<222> LOCATION: (2)..(2)
<223> OTHER INFORMATION: wherein Xaa = 4-aminobutyric acid

<400> SEQUENCE: 6

Xaa Xaa Gly Leu Leu
1               5

```
<210> SEQ ID NO 7
<211> LENGTH: 5
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-proline
<220> FEATURE:
<221> NAME/KEY: MISC_FEATURE
<222> LOCATION: (2)..(2)
<223> OTHER INFORMATION: wherein Xaa = cyclohexylalanine

<400> SEQUENCE: 7

Xaa Xaa Gly Leu Leu
1               5

<210> SEQ ID NO 8
<211> LENGTH: 5
<212> TYPE: PRT
<213> ORGANISM: Artificial
<220> FEATURE:
<223> OTHER INFORMATION: Synthetic Sequence

<400> SEQUENCE: 8

Pro Leu Gly Leu Leu
1               5

<210> SEQ ID NO 9
<211> LENGTH: 5
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = MeOCH2CH2OCH2 (=O) -proline

<400> SEQUENCE: 9

Xaa Leu Gly Leu Leu
1               5

<210> SEQ ID NO 10
<211> LENGTH: 5
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = MeOCH2CH2OCH2CH2OCH2C (=O)
      -proline

<400> SEQUENCE: 10

Xaa Leu Gly Leu Leu
1               5

<210> SEQ ID NO 11
<211> LENGTH: 5
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
```

```
<223> OTHER INFORMATION: wherein Xaa = H2NCH2CH2N (CH2CH2) 2NCH2C (=O)
      -proline

<400> SEQUENCE: 11

Xaa Leu Gly Leu Leu
1               5

<210> SEQ ID NO 12
<211> LENGTH: 5
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = AcHNCH2CH2N (CH2CH2) 2NCH2C (=O)
      -proline

<400> SEQUENCE: 12

Xaa Leu Gly Leu Leu
1               5

<210> SEQ ID NO 13
<211> LENGTH: 5
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = AcN(CH2CH2)  2NCH2C (=O) -proline

<400> SEQUENCE: 13

Xaa Leu Gly Leu Leu
1               5

<210> SEQ ID NO 14
<211> LENGTH: 4
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (4)..(4)
<223> OTHER INFORMATION: wherein Xaa = O-benzyl-serine

<400> SEQUENCE: 14

Pro Leu Gly Xaa
1

<210> SEQ ID NO 15
<211> LENGTH: 4
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-proline

<400> SEQUENCE: 15

Xaa Leu Gly Leu
1

<210> SEQ ID NO 16
```

```
<211> LENGTH: 5
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-glycine

<400> SEQUENCE: 16

Xaa Pro Leu Gly Leu
1               5

<210> SEQ ID NO 17
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = N,N-dimethylglycine
<220> FEATURE:
<221> NAME/KEY: MISC_FEATURE
<222> LOCATION: (3)..(3)
<223> OTHER INFORMATION: wherein Xaa = sarcosine (N-methylglycine)
<220> FEATURE:
<221> NAME/KEY: MISC_FEATURE
<222> LOCATION: (4)..(4)
<223> OTHER INFORMATION: wherein Xaa = homophenylalanine
<220> FEATURE:
<221> NAME/KEY: misc_feature
<222> LOCATION: (5)..(5)
<223> OTHER INFORMATION: Xaa can be any naturally occurring amino acid

<400> SEQUENCE: 17

Xaa Pro Arg Xaa Xaa Leu
1               5

<210> SEQ ID NO 18
<211> LENGTH: 5
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-proline
<220> FEATURE:
<221> NAME/KEY: MISC_FEATURE
<222> LOCATION: (4)..(4)
<223> OTHER INFORMATION: wherein Xaa = homophenylalanine

<400> SEQUENCE: 18

Xaa His Gly Xaa Leu
1               5

<210> SEQ ID NO 19
<211> LENGTH: 5
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-proline
<220> FEATURE:
<221> NAME/KEY: MISC_FEATURE
<222> LOCATION: (2)..(2)
```

```
<223> OTHER INFORMATION: wherein Xaa = ornithine
<220> FEATURE:
<221> NAME/KEY: MISC_FEATURE
<222> LOCATION: (4)..(4)
<223> OTHER INFORMATION: wherein Xaa = homophenylalanine

<400> SEQUENCE: 19

Xaa Xaa Gly Xaa Leu
1               5

<210> SEQ ID NO 20
<211> LENGTH: 5
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-proline
<220> FEATURE:
<221> NAME/KEY: MISC_FEATURE
<222> LOCATION: (2)..(2)
<223> OTHER INFORMATION: wherein Xaa = diaminoproprionic acid
<220> FEATURE:
<221> NAME/KEY: MISC_FEATURE
<222> LOCATION: (4)..(4)
<223> OTHER INFORMATION: wherein Xaa = homophenylalanine

<400> SEQUENCE: 20

Xaa Xaa Gly Xaa Leu
1               5

<210> SEQ ID NO 21
<211> LENGTH: 5
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-proline
<220> FEATURE:
<221> NAME/KEY: MISC_FEATURE
<222> LOCATION: (2)..(2)
<223> OTHER INFORMATION: wherein Xaa = N5-aminocarbonylornithine
<220> FEATURE:
<221> NAME/KEY: MISC_FEATURE
<222> LOCATION: (4)..(4)
<223> OTHER INFORMATION: wherein Xaa = homophenylalanine

<400> SEQUENCE: 21

Xaa Xaa Gly Xaa Leu
1               5

<210> SEQ ID NO 22
<211> LENGTH: 5
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-proline
<220> FEATURE:
<221> NAME/KEY: MISC_FEATURE
<222> LOCATION: (4)..(4)
<223> OTHER INFORMATION: wherein Xaa = (O-(3-pyridyl-)) tyrosine

<400> SEQUENCE: 22
```

```
Xaa Leu Gly Xaa Leu
1               5

<210> SEQ ID NO 23
<211> LENGTH: 5
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-proline
<220> FEATURE:
<221> NAME/KEY: MISC_FEATURE
<222> LOCATION: (4)..(4)
<223> OTHER INFORMATION: wherein Xaa = (O-(4-pyridyl-)) tyrosine

<400> SEQUENCE: 23

Xaa Leu Gly Xaa Leu
1               5

<210> SEQ ID NO 24
<211> LENGTH: 5
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl proline
<220> FEATURE:
<221> NAME/KEY: MISC_FEATURE
<222> LOCATION: (4)..(4)
<223> OTHER INFORMATION: wherein Xaa = (4-aza-) homophenylalanine

<400> SEQUENCE: 24

Xaa Leu Gly Xaa Leu
1               5

<210> SEQ ID NO 25
<211> LENGTH: 5
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-proline
<220> FEATURE:
<221> NAME/KEY: MISC_FEATURE
<222> LOCATION: (4)..(4)
<223> OTHER INFORMATION: wherein Xaa = (O-benzyl-) serine

<400> SEQUENCE: 25

Xaa Leu Gly Xaa Leu
1               5

<210> SEQ ID NO 26
<211> LENGTH: 5
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = carbobenzyloxy-proline
<220> FEATURE:
<221> NAME/KEY: MISC_FEATURE
```

```
<222> LOCATION: (4)..(4)
<223> OTHER INFORMATION: wherein Xaa = (O-(4-pyridylmethyl-)) tyrosine

<400> SEQUENCE: 26

Xaa Leu Gly Xaa Leu
 1               5

<210> SEQ ID NO 27
<211> LENGTH: 5
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-proline
<220> FEATURE:
<221> NAME/KEY: MISC_FEATURE
<222> LOCATION: (3)..(3)
<223> OTHER INFORMATION: wherein Xaa = sarcosine (N-methylglycine)

<400> SEQUENCE: 27

Xaa Leu Xaa Leu Leu
 1               5

<210> SEQ ID NO 28
<211> LENGTH: 5
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-proline
<220> FEATURE:
<221> NAME/KEY: MISC_FEATURE
<222> LOCATION: (2)..(2)
<223> OTHER INFORMATION: wherein Xaa = (N-Me-) leucine

<400> SEQUENCE: 28

Xaa Xaa Gly Leu Leu
 1               5

<210> SEQ ID NO 29
<211> LENGTH: 5
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-proline
<220> FEATURE:
<221> NAME/KEY: MISC_FEATURE
<222> LOCATION: (4)..(4)
<223> OTHER INFORMATION: wherein Xaa = (N-Me-) leucine

<400> SEQUENCE: 29

Xaa Leu Gly Xaa Leu
 1               5

<210> SEQ ID NO 30
<211> LENGTH: 5
<212> TYPE: PRT
<213> ORGANISM: Artificial
<220> FEATURE:
<223> OTHER INFORMATION: Synthetic Sequence
<220> FEATURE:
```

```
<221> NAME/KEY: MISC_FEATURE
<222> LOCATION: (1)..(1)
<223> OTHER INFORMATION: wherein Xaa = acetyl 4-hydroxyproline

<400> SEQUENCE: 30

Xaa Leu Gly Leu Leu
1               5

<210> SEQ ID NO 31
<211> LENGTH: 5
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl- (thiazolidine-4-carbonyl)

<400> SEQUENCE: 31

Xaa Leu Gly Leu Leu
1               5

<210> SEQ ID NO 32
<211> LENGTH: 5
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl - (Homo-proline)

<400> SEQUENCE: 32

Xaa Leu Gly Leu Leu
1               5

<210> SEQ ID NO 33
<211> LENGTH: 5
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl- (Homo-proline)
<220> FEATURE:
<221> NAME/KEY: MISC_FEATURE
<222> LOCATION: (4)..(4)
<223> OTHER INFORMATION: wherein Xaa = homophenylalanine

<400> SEQUENCE: 33

Xaa Leu Gly Xaa Leu
1               5

<210> SEQ ID NO 34
<211> LENGTH: 5
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl- (Homo-proline)
<220> FEATURE:
<221> NAME/KEY: MISC_FEATURE
<222> LOCATION: (2)..(2)
<223> OTHER INFORMATION: wherein Xaa = ornithine
```

```
<220> FEATURE:
<221> NAME/KEY: MISC_FEATURE
<222> LOCATION: (4)..(4)
<223> OTHER INFORMATION: wherein Xaa = homophenylalanine

<400> SEQUENCE: 34

Xaa Xaa Gly Xaa Leu
1               5

<210> SEQ ID NO 35
<211> LENGTH: 5
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-Nipecotate

<400> SEQUENCE: 35

Xaa Leu Gly Leu Leu
1               5

<210> SEQ ID NO 36
<211> LENGTH: 5
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-2-carboxyazetidine

<400> SEQUENCE: 36

Xaa Leu Gly Leu Leu
1               5

<210> SEQ ID NO 37
<211> LENGTH: 5
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-cyclohexylglycine

<400> SEQUENCE: 37

Xaa Leu Gly Leu Leu
1               5

<210> SEQ ID NO 38
<211> LENGTH: 5
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-proline
<220> FEATURE:
<221> NAME/KEY: MISC_FEATURE
<222> LOCATION: (2)..(2)
<223> OTHER INFORMATION: wherein Xaa = valerolactam

<400> SEQUENCE: 38
```

```
Xaa Xaa Gly Leu Leu
1               5

<210> SEQ ID NO 39
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-glycine

<400> SEQUENCE: 39

Xaa Pro Leu Gly Leu Phe
1               5

<210> SEQ ID NO 40
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-glycine

<400> SEQUENCE: 40

Xaa Pro Leu Gly Phe Phe
1               5

<210> SEQ ID NO 41
<211> LENGTH: 5
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-leucine

<400> SEQUENCE: 41

Xaa Gly Leu Tyr Leu
1               5

<210> SEQ ID NO 42
<211> LENGTH: 5
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = cyclopropylcarbonyl-leucine

<400> SEQUENCE: 42

Xaa Gly Leu Tyr Leu
1               5

<210> SEQ ID NO 43
<211> LENGTH: 5
<212> TYPE: PRT
<213> ORGANISM: Artificial
<220> FEATURE:
<223> OTHER INFORMATION: Synthetic Sequence
<220> FEATURE:
```

```
<221> NAME/KEY: MISC_FEATURE
<222> LOCATION: (1)..(1)
<223> OTHER INFORMATION: wherein Xaa = cyclobutylcarbonyl-leucine

<400> SEQUENCE: 43

Xaa Gly Leu Tyr Leu
1               5

<210> SEQ ID NO 44
<211> LENGTH: 5
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = pivaloyl-leucine

<400> SEQUENCE: 44

Xaa Gly Leu Tyr Leu
1               5

<210> SEQ ID NO 45
<211> LENGTH: 7
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = 4-hydroxproline

<400> SEQUENCE: 45

Xaa Gly Pro Leu Gly Leu Leu
1               5

<210> SEQ ID NO 46
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-proline

<400> SEQUENCE: 46

Xaa Leu Gly Leu Ala Leu
1               5

<210> SEQ ID NO 47
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-proline

<400> SEQUENCE: 47

Xaa Leu Gly Leu Ala Leu
1               5

<210> SEQ ID NO 48
```

```
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = polyethyleneglycol-proline

<400> SEQUENCE: 48

Xaa Leu Gly Leu Tyr Leu
1               5

<210> SEQ ID NO 49
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = H3CC (=O) NH-polyethyleneglycol
      -proline

<400> SEQUENCE: 49

Xaa Leu Gly Leu Tyr Leu
1               5

<210> SEQ ID NO 50
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = AcHNCH2CH2N (CH2CH2) 2NCH2C (=O)
      -proline

<400> SEQUENCE: 50

Xaa Leu Gly Leu Tyr Leu
1               5

<210> SEQ ID NO 51
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-proline

<400> SEQUENCE: 51

Xaa Leu Gly Leu Ser Leu
1               5

<210> SEQ ID NO 52
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-glycine
```

```
<400> SEQUENCE: 52

Xaa Pro Leu Gly Leu Leu
1               5

<210> SEQ ID NO 53
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = O (CH2CH2) NCH2CH2NHC (=O)
      -glycine

<400> SEQUENCE: 53

Xaa Pro Leu Gly Leu Leu
1               5

<210> SEQ ID NO 54
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-glycine

<400> SEQUENCE: 54

Xaa Pro Leu Gly Leu Tyr
1               5

<210> SEQ ID NO 55
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-proline

<400> SEQUENCE: 55

Xaa Leu Gly Leu Leu Leu
1               5

<210> SEQ ID NO 56
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-glycine
<220> FEATURE:
<221> NAME/KEY: MISC_FEATURE
<222> LOCATION: (5)..(5)
<223> OTHER INFORMATION: wherein Xaa = biphenylalanine

<400> SEQUENCE: 56

Xaa Pro Leu Gly Xaa Phe
1               5
```

<210> SEQ ID NO 57
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-glycine
<220> FEATURE:
<221> NAME/KEY: MISC_FEATURE
<222> LOCATION: (5)..(5)
<223> OTHER INFORMATION: wherein Xaa = norleucine

<400> SEQUENCE: 57

Xaa Pro Leu Gly Xaa Phe
1               5

<210> SEQ ID NO 58
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = carbobenzyloxy-glycine

<400> SEQUENCE: 58

Xaa Pro Leu Gly Leu Leu
1               5

<210> SEQ ID NO 59
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = AcHNCH2CH2N (CH2CH2) 2NCH2C (=O)
      -glycine

<400> SEQUENCE: 59

Xaa Pro Leu Gly Leu Leu
1               5

<210> SEQ ID NO 60
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = H2NCH2CH2N (CH2CH2) 2NCH2C (=O)
      -glycine

<400> SEQUENCE: 60

Xaa Pro Leu Gly Leu Leu
1               5

<210> SEQ ID NO 61
<211> LENGTH: 6
<212> TYPE: PRT
<213> ORGANISM: Artificial

```
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = N,N-dimethylglycine

<400> SEQUENCE: 61

Xaa Pro Leu Gly Leu Leu
1               5

<210> SEQ ID NO 62
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-gamma-glutamic acid

<400> SEQUENCE: 62

Xaa Pro Leu Gly Leu Leu
1               5

<210> SEQ ID NO 63
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-glycine
<220> FEATURE:
<221> NAME/KEY: MISC_FEATURE
<222> LOCATION: (5)..(5)
<223> OTHER INFORMATION: wherein Xaa = 3-thienylalanine

<400> SEQUENCE: 63

Xaa Pro Leu Gly Xaa Phe
1               5

<210> SEQ ID NO 64
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-glycine
<220> FEATURE:
<221> NAME/KEY: MISC_FEATURE
<222> LOCATION: (5)..(5)
<223> OTHER INFORMATION: wherein Xaa = 2-phenylglycine

<400> SEQUENCE: 64

Xaa Pro Leu Gly Xaa Phe
1               5

<210> SEQ ID NO 65
<211> LENGTH: 6
<212> TYPE: PRT
<213> ORGANISM: Artificial
<220> FEATURE:
<223> OTHER INFORMATION: Synthetic Sequence
<220> FEATURE:
```

```
<221> NAME/KEY: MISC_FEATURE
<222> LOCATION: (1)..(1)
<223> OTHER INFORMATION: wherein Xaa = methoxyacetyl-glycine

<400> SEQUENCE: 65

Xaa Pro Leu Gly Leu Leu
1               5

<210> SEQ ID NO 66
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = N,N-dimethylglycine
<220> FEATURE:
<221> NAME/KEY: MISC_FEATURE
<222> LOCATION: (5)..(5)
<223> OTHER INFORMATION: wherein Xaa = 3-thienylalanine

<400> SEQUENCE: 66

Xaa Pro Leu Gly Xaa Leu
1               5

<210> SEQ ID NO 67
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = N,N-dimethylglycine
<220> FEATURE:
<221> NAME/KEY: MISC_FEATURE
<222> LOCATION: (5)..(5)
<223> OTHER INFORMATION: wherein Xaa = 2-phenylglycine

<400> SEQUENCE: 67

Xaa Pro Leu Gly Xaa Leu
1               5

<210> SEQ ID NO 68
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = N,N-dimethylglycine
<220> FEATURE:
<221> NAME/KEY: MISC_FEATURE
<222> LOCATION: (5)..(5)
<223> OTHER INFORMATION: wherein Xaa = O-benzyl-tyrosine

<400> SEQUENCE: 68

Xaa Pro Leu Gly Xaa Leu
1               5

<210> SEQ ID NO 69
<211> LENGTH: 6
<212> TYPE: PRT
<213> ORGANISM: Artificial
<220> FEATURE:
<223> OTHER INFORMATION: Synthetic Sequence
```

```
<220> FEATURE:
<221> NAME/KEY: MISC_FEATURE
<222> LOCATION: (1)..(1)
<223> OTHER INFORMATION: wherein Xaa = N,N-dimethylglycine
<220> FEATURE:
<221> NAME/KEY: MISC_FEATURE
<222> LOCATION: (5)..(5)
<223> OTHER INFORMATION: wherein Xaa = biphenylalanine

<400> SEQUENCE: 69

Xaa Pro Leu Gly Xaa Leu
1               5

<210> SEQ ID NO 70
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-glycine
<220> FEATURE:
<221> NAME/KEY: MISC_FEATURE
<222> LOCATION: (6)..(6)
<223> OTHER INFORMATION: wherein Xaa = biphenylalanine

<400> SEQUENCE: 70

Xaa Pro Leu Gly Phe Xaa
1               5

<210> SEQ ID NO 71
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-glycine
<220> FEATURE:
<221> NAME/KEY: MISC_FEATURE
<222> LOCATION: (6)..(6)
<223> OTHER INFORMATION: wherein Xaa = biphenylalanine

<400> SEQUENCE: 71

Xaa Pro Leu Gly Leu Xaa
1               5

<210> SEQ ID NO 72
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-glycine
<220> FEATURE:
<221> NAME/KEY: MISC_FEATURE
<222> LOCATION: (5)..(5)
<223> OTHER INFORMATION: wherein Xaa = 2-naphthylalanine
<220> FEATURE:
<221> NAME/KEY: MISC_FEATURE
<222> LOCATION: (6)..(6)
<223> OTHER INFORMATION: wherein Xaa = biphenylalanine

<400> SEQUENCE: 72

Xaa Pro Leu Gly Xaa Xaa
```

```
<210> SEQ ID NO 73
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-glycine

<400> SEQUENCE: 73

Xaa Pro Leu Gly Phe Ala
1               5

<210> SEQ ID NO 74
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-glycine
<220> FEATURE:
<221> NAME/KEY: MISC_FEATURE
<222> LOCATION: (5)..(5)
<223> OTHER INFORMATION: wherein Xaa = biphenylalanine

<400> SEQUENCE: 74

Xaa Pro Leu Gly Xaa Ala
1               5

<210> SEQ ID NO 75
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-glycine

<400> SEQUENCE: 75

Xaa Pro Leu Gly Leu Ala
1               5

<210> SEQ ID NO 76
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-glycine
<220> FEATURE:
<221> NAME/KEY: MISC_FEATURE
<222> LOCATION: (5)..(5)
<223> OTHER INFORMATION: wherein Xaa = O-benzyl-tyrosine

<400> SEQUENCE: 76

Xaa Pro Leu Gly Xaa Phe
1               5
```

-continued

```
<210> SEQ ID NO 77
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-glycine

<400> SEQUENCE: 77

Xaa Pro Gln Gly Leu Leu
1               5

<210> SEQ ID NO 78
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-glycine

<400> SEQUENCE: 78

Xaa Pro Arg Gly Leu Leu
1               5

<210> SEQ ID NO 79
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-glycine
<220> FEATURE:
<221> NAME/KEY: MISC_FEATURE
<222> LOCATION: (6)..(6)
<223> OTHER INFORMATION: wherein Xaa =4-pyridyl-alanine

<400> SEQUENCE: 79

Xaa Pro Leu Gly Leu Xaa
1               5

<210> SEQ ID NO 80
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-glycine

<400> SEQUENCE: 80

Xaa Pro Leu Gly Leu Arg
1               5

<210> SEQ ID NO 81
<211> LENGTH: 6
<212> TYPE: PRT
<213> ORGANISM: Artificial
<220> FEATURE:
<223> OTHER INFORMATION: Synthetic Sequence
<220> FEATURE:
```

-continued

```
<221> NAME/KEY: MISC_FEATURE
<222> LOCATION: (1)..(1)
<223> OTHER INFORMATION: wherein Xaa = acetyl-glycine

<400> SEQUENCE: 81

Xaa Pro Leu Gly Leu Trp
1               5

<210> SEQ ID NO 82
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-glycine

<400> SEQUENCE: 82

Xaa Pro Leu Gly Val Leu
1               5

<210> SEQ ID NO 83
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-glycine
<220> FEATURE:
<221> NAME/KEY: MISC_FEATURE
<222> LOCATION: (5)..(5)
<223> OTHER INFORMATION: wherein Xaa = homophenylalanine

<400> SEQUENCE: 83

Xaa Pro Leu Gly Xaa Leu
1               5

<210> SEQ ID NO 84
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-glycine

<400> SEQUENCE: 84

Xaa Pro Leu Ala Leu Leu
1               5

<210> SEQ ID NO 85
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = N, N-dimethylglycine
<220> FEATURE:
<221> NAME/KEY: MISC_FEATURE
<222> LOCATION: (5)..(5)
<223> OTHER INFORMATION: wherein Xaa = biphenylalanine
```

```
<400> SEQUENCE: 85

Xaa Pro Ile Gly Xaa Leu
1               5

<210> SEQ ID NO 86
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = N,N-dimethylglycine
<220> FEATURE:
<221> NAME/KEY: MISC_FEATURE
<222> LOCATION: (3)..(3)
<223> OTHER INFORMATION: wherein Xaa = cyclohexylglycine
<220> FEATURE:
<221> NAME/KEY: MISC_FEATURE
<222> LOCATION: (5)..(5)
<223> OTHER INFORMATION: wherein Xaa = biphenylalanine

<400> SEQUENCE: 86

Xaa Pro Xaa Gly Xaa Leu
1               5

<210> SEQ ID NO 87
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-glycine

<400> SEQUENCE: 87

Xaa Pro Val Gly Leu Leu
1               5

<210> SEQ ID NO 88
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = N,N-dimethylglycine

<400> SEQUENCE: 88

Xaa Pro Ile Gly Leu Leu
1               5

<210> SEQ ID NO 89
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = N,N-dimethylglycine
<220> FEATURE:
<221> NAME/KEY: MISC_FEATURE
<222> LOCATION: (5)..(5)
```

```
<223> OTHER INFORMATION: wherein Xaa = biphenylalanine

<400> SEQUENCE: 89

Xaa Pro Arg Gly Xaa Leu
1               5

<210> SEQ ID NO 90
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-glycine
<220> FEATURE:
<221> NAME/KEY: MISC_FEATURE
<222> LOCATION: (6)..(6)
<223> OTHER INFORMATION: wherein Xaa = O-benzyl-tyrosine

<400> SEQUENCE: 90

Xaa Pro Leu Gly Leu Xaa
1               5

<210> SEQ ID NO 91
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = N, N-dimethylglycine

<400> SEQUENCE: 91

Xaa Pro Leu Gly Glu Leu
1               5

<210> SEQ ID NO 92
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = N,N-dimethylglycine
<220> FEATURE:
<221> NAME/KEY: MISC_FEATURE
<222> LOCATION: (5)..(5)
<223> OTHER INFORMATION: wherein Xaa = biphenylalanine

<400> SEQUENCE: 92

Xaa Pro Lys Gly Xaa Leu
1               5

<210> SEQ ID NO 93
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-glycine

<400> SEQUENCE: 93
```

```
Xaa Pro Leu Gly Leu Glu
1               5

<210> SEQ ID NO 94
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-glycine
<220> FEATURE:
<221> NAME/KEY: MISC_FEATURE
<222> LOCATION: (5)..(5)
<223> OTHER INFORMATION: wherein Xaa = biphenylalanine

<400> SEQUENCE: 94

Xaa Pro Leu Gly Xaa Glu
1               5

<210> SEQ ID NO 95
<211> LENGTH: 7
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = N,N-dimethylglycine
<220> FEATURE:
<221> NAME/KEY: MISC_FEATURE
<222> LOCATION: (4)..(4)
<223> OTHER INFORMATION: wherein Xaa = sarcosine (N-methylglycine)
<220> FEATURE:
<221> NAME/KEY: MISC_FEATURE
<222> LOCATION: (5)..(5)
<223> OTHER INFORMATION: wherein Xaa = homophenylalanine

<400> SEQUENCE: 95

Xaa Pro Arg Xaa Xaa Arg Leu
1               5

<210> SEQ ID NO 96
<211> LENGTH: 7
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = N,N-dimethylglycine
<220> FEATURE:
<221> NAME/KEY: MISC_FEATURE
<222> LOCATION: (5)..(5)
<223> OTHER INFORMATION: wherein Xaa = homophenylalanine

<400> SEQUENCE: 96

Xaa Pro Arg Gly Xaa Arg Leu
1               5

<210> SEQ ID NO 97
<211> LENGTH: 7
<212> TYPE: PRT
<213> ORGANISM: Artificial
<220> FEATURE:
<223> OTHER INFORMATION: Synthetic Sequence
<220> FEATURE:
```

```
<221> NAME/KEY: MISC_FEATURE
<222> LOCATION: (1)..(1)
<223> OTHER INFORMATION: wherein Xaa = N,N-dimethylglycine
<220> FEATURE:
<221> NAME/KEY: MISC_FEATURE
<222> LOCATION: (5)..(5)
<223> OTHER INFORMATION: wherein Xaa = biphenylalanine

<400> SEQUENCE: 97

Xaa Pro Arg Gly Xaa Arg Leu
1               5

<210> SEQ ID NO 98
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-glycine

<400> SEQUENCE: 98

Xaa Pro Leu Gly Asn Leu
1               5

<210> SEQ ID NO 99
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-glycine

<400> SEQUENCE: 99

Xaa Pro Leu Gly Ser Leu
1               5

<210> SEQ ID NO 100
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-glycine
<220> FEATURE:
<221> NAME/KEY: MISC_FEATURE
<222> LOCATION: (5)..(5)
<223> OTHER INFORMATION: wherein Xaa = 4-hydroxy-phenyl-glycine

<400> SEQUENCE: 100

Xaa Pro Leu Gly Xaa Leu
1               5

<210> SEQ ID NO 101
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-proline
```

```
<220> FEATURE:
<221> NAME/KEY: MISC_FEATURE
<222> LOCATION: (4)..(4)
<223> OTHER INFORMATION: wherein Xaa = homophenylalanine

<400> SEQUENCE: 101

Xaa Leu Gly Xaa His Leu
1               5

<210> SEQ ID NO 102
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-proline
<220> FEATURE:
<221> NAME/KEY: MISC_FEATURE
<222> LOCATION: (4)..(4)
<223> OTHER INFORMATION: wherein Xaa = homophenylalanine

<400> SEQUENCE: 102

Xaa Leu Gly Xaa Ala Leu
1               5

<210> SEQ ID NO 103
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-proline
<220> FEATURE:
<221> NAME/KEY: MISC_FEATURE
<222> LOCATION: (4)..(4)
<223> OTHER INFORMATION: wherein Xaa = homophenylalanine

<400> SEQUENCE: 103

Xaa Leu Gly Xaa Tyr Leu
1               5

<210> SEQ ID NO 104
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-proline
<220> FEATURE:
<221> NAME/KEY: MISC_FEATURE
<222> LOCATION: (4)..(4)
<223> OTHER INFORMATION: wherein Xaa = homophenylalanine
<220> FEATURE:
<221> NAME/KEY: MISC_FEATURE
<222> LOCATION: (5)..(5)
<223> OTHER INFORMATION: wherein Xaa = morpholinylpropyl-glycine

<400> SEQUENCE: 104

Xaa Leu Gly Xaa Xaa Leu
1               5

<210> SEQ ID NO 105
```

```
<211> LENGTH: 7
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-gamma-glutamic acid
<220> FEATURE:
<221> NAME/KEY: MISC_FEATURE
<222> LOCATION: (5)..(5)
<223> OTHER INFORMATION: wherein Xaa = homophenylalanine

<400> SEQUENCE: 105

Xaa Pro Leu Gly Xaa Tyr Leu
1               5

<210> SEQ ID NO 106
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = succinyl-proline
<220> FEATURE:
<221> NAME/KEY: MISC_FEATURE
<222> LOCATION: (4)..(4)
<223> OTHER INFORMATION: wherein Xaa = homophenylalanine

<400> SEQUENCE: 106

Xaa Leu Gly Xaa Tyr Leu
1               5

<210> SEQ ID NO 107
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-proline
<220> FEATURE:
<221> NAME/KEY: MISC_FEATURE
<222> LOCATION: (4)..(4)
<223> OTHER INFORMATION: wherein Xaa = homophenylalanine
<220> FEATURE:
<221> NAME/KEY: MISC_FEATURE
<222> LOCATION: (5)..(5)
<223> OTHER INFORMATION: wherein Xaa = (O-(4-pyridylmethyl)-tyrosine)

<400> SEQUENCE: 107

Xaa Leu Gly Xaa Xaa Leu
1               5

<210> SEQ ID NO 108
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-proline
<220> FEATURE:
<221> NAME/KEY: MISC_FEATURE
<222> LOCATION: (4)..(4)
```

```
<223> OTHER INFORMATION: wherein Xaa = homo-tyrosine

<400> SEQUENCE: 108

Xaa Leu Gly Xaa Tyr Leu
1               5

<210> SEQ ID NO 109
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-proline
<220> FEATURE:
<221> NAME/KEY: MISC_FEATURE
<222> LOCATION: (4)..(4)
<223> OTHER INFORMATION: wherein Xaa = 4-aza-homophenylalanine

<400> SEQUENCE: 109

Xaa Leu Gly Xaa Tyr Leu
1               5

<210> SEQ ID NO 110
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-proline
<220> FEATURE:
<221> NAME/KEY: MISC_FEATURE
<222> LOCATION: (4)..(4)
<223> OTHER INFORMATION: wherein Xaa = (O-(4-pyridyl-)-tyrosine)

<400> SEQUENCE: 110

Xaa Leu Gly Xaa Tyr Leu
1               5

<210> SEQ ID NO 111
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-proline
<220> FEATURE:
<221> NAME/KEY: MISC_FEATURE
<222> LOCATION: (4)..(4)
<223> OTHER INFORMATION: wherein Xaa = phenylpropyl-glycine

<400> SEQUENCE: 111

Xaa Leu Gly Xaa Tyr Leu
1               5

<210> SEQ ID NO 112
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
```

```
<222> LOCATION: (1)..(1)
<223> OTHER INFORMATION: wherein Xaa = acetyl-proline
<220> FEATURE:
<221> NAME/KEY: MISC_FEATURE
<222> LOCATION: (4)..(4)
<223> OTHER INFORMATION: wherein Xaa = styryl-alanine

<400> SEQUENCE: 112

Xaa Leu Gly Xaa Tyr Leu
1               5

<210> SEQ ID NO 113
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-proline
<220> FEATURE:
<221> NAME/KEY: MISC_FEATURE
<222> LOCATION: (4)..(4)
<223> OTHER INFORMATION: wherein Xaa = O-benzyl-serine

<400> SEQUENCE: 113

Xaa Leu Gly Xaa Tyr Leu
1               5

<210> SEQ ID NO 114
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-proline
<220> FEATURE:
<221> NAME/KEY: MISC_FEATURE
<222> LOCATION: (2)..(2)
<223> OTHER INFORMATION: wherein Xaa = N,N-dimethyl-lysine
<220> FEATURE:
<221> NAME/KEY: MISC_FEATURE
<222> LOCATION: (4)..(4)
<223> OTHER INFORMATION: wherein Xaa = homophenylalanine

<400> SEQUENCE: 114

Xaa Xaa Gly Xaa Tyr Leu
1               5

<210> SEQ ID NO 115
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-proline
<220> FEATURE:
<221> NAME/KEY: MISC_FEATURE
<222> LOCATION: (4)..(4)
<223> OTHER INFORMATION: wherein Xaa = homphenylalanine
<220> FEATURE:
<221> NAME/KEY: MISC_FEATURE
<222> LOCATION: (5)..(5)
<223> OTHER INFORMATION: wherein Xaa = diaminopropionic acid

<400> SEQUENCE: 115
```

Xaa Leu Gly Xaa Xaa Leu
1               5

<210> SEQ ID NO 116
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-proline
<220> FEATURE:
<221> NAME/KEY: MISC_FEATURE
<222> LOCATION: (4)..(4)
<223> OTHER INFORMATION: wherein Xaa = homophenylalanine
<220> FEATURE:
<221> NAME/KEY: MISC_FEATURE
<222> LOCATION: (5)..(5)
<223> OTHER INFORMATION: wherein Xaa = ornithine

<400> SEQUENCE: 116

Xaa Leu Gly Xaa Xaa Leu
1               5

<210> SEQ ID NO 117
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = polyethyleneglycol-proline
<220> FEATURE:
<221> NAME/KEY: MISC_FEATURE
<222> LOCATION: (4)..(4)
<223> OTHER INFORMATION: wherein Xaa = homophenylalanine
<220> FEATURE:
<221> NAME/KEY: MISC_FEATURE
<222> LOCATION: (5)..(5)
<223> OTHER INFORMATION: wherein Xaa = ornithine

<400> SEQUENCE: 117

Xaa Leu Gly Xaa Xaa Leu
1               5

<210> SEQ ID NO 118
<211> LENGTH: 7
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-gamma-glutamic acid
<220> FEATURE:
<221> NAME/KEY: MISC_FEATURE
<222> LOCATION: (5)..(5)
<223> OTHER INFORMATION: wherein Xaa = homophenylalanine
<220> FEATURE:
<221> NAME/KEY: MISC_FEATURE
<222> LOCATION: (6)..(6)
<223> OTHER INFORMATION: wherein Xaa = ornithine

<400> SEQUENCE: 118

Xaa Pro Leu Gly Xaa Xaa Leu
1               5

```
<210> SEQ ID NO 119
<211> LENGTH: 7
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = gamma-glutamic acid
<220> FEATURE:
<221> NAME/KEY: MISC_FEATURE
<222> LOCATION: (5)..(5)
<223> OTHER INFORMATION: wherein Xaa = homophenylalanine
<220> FEATURE:
<221> NAME/KEY: MISC_FEATURE
<222> LOCATION: (6)..(6)
<223> OTHER INFORMATION: wherein Xaa = ornithine

<400> SEQUENCE: 119

Xaa Pro Leu Gly Xaa Xaa Leu
1               5

<210> SEQ ID NO 120
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-proline
<220> FEATURE:
<221> NAME/KEY: MISC_FEATURE
<222> LOCATION: (2)..(2)
<223> OTHER INFORMATION: wherein Xaa = ornithine
<220> FEATURE:
<221> NAME/KEY: MISC_FEATURE
<222> LOCATION: (4)..(4)
<223> OTHER INFORMATION: wherein Xaa = homophenylalanine
<220> FEATURE:
<221> NAME/KEY: MISC_FEATURE
<222> LOCATION: (5)..(5)
<223> OTHER INFORMATION: wherein Xaa = ornithine

<400> SEQUENCE: 120

Xaa Xaa Gly Xaa Xaa Leu
1               5

<210> SEQ ID NO 121
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-proline
<220> FEATURE:
<221> NAME/KEY: MISC_FEATURE
<222> LOCATION: (2)..(2)
<223> OTHER INFORMATION: wherein Xaa = ornithine
<220> FEATURE:
<221> NAME/KEY: MISC_FEATURE
<222> LOCATION: (4)..(4)
<223> OTHER INFORMATION: wherein Xaa = homophenylalanine

<400> SEQUENCE: 121

Xaa Xaa Gly Xaa Tyr Leu
1               5
```

```
<210> SEQ ID NO 122
<211> LENGTH: 7
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-gamma-glutamic acid
<220> FEATURE:
<221> NAME/KEY: MISC_FEATURE
<222> LOCATION: (3)..(3)
<223> OTHER INFORMATION: wherein Xaa = ornithine
<220> FEATURE:
<221> NAME/KEY: MISC_FEATURE
<222> LOCATION: (5)..(5)
<223> OTHER INFORMATION: wherein Xaa = homophenylalanine

<400> SEQUENCE: 122

Xaa Pro Xaa Gly Xaa Glu Leu
1               5

<210> SEQ ID NO 123
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-proline
<220> FEATURE:
<221> NAME/KEY: MISC_FEATURE
<222> LOCATION: (2)..(2)
<223> OTHER INFORMATION: wherein Xaa = ornithine

<400> SEQUENCE: 123

Xaa Xaa Gly Leu Tyr Leu
1               5

<210> SEQ ID NO 124
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-proline
<220> FEATURE:
<221> NAME/KEY: MISC_FEATURE
<222> LOCATION: (2)..(2)
<223> OTHER INFORMATION: wherein Xaa = 4-aza-phenylalanine

<400> SEQUENCE: 124

Xaa Xaa Gly Leu Tyr Leu
1               5

<210> SEQ ID NO 125
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-proline
<220> FEATURE:
```

```
<221> NAME/KEY: MISC_FEATURE
<222> LOCATION: (4)..(4)
<223> OTHER INFORMATION: wherein Xaa = homophenylalanine
<220> FEATURE:
<221> NAME/KEY: MISC_FEATURE
<222> LOCATION: (5)..(5)
<223> OTHER INFORMATION: wherein Xaa = 2,4-diaminobutanoic acid

<400> SEQUENCE: 125

Xaa Leu Gly Xaa Xaa Leu
1               5

<210> SEQ ID NO 126
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-proline
<220> FEATURE:
<221> NAME/KEY: MISC_FEATURE
<222> LOCATION: (4)..(4)
<223> OTHER INFORMATION: wherein Xaa = homophenylalanine

<400> SEQUENCE: 126

Xaa Leu Gly Xaa Lys Leu
1               5

<210> SEQ ID NO 127
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-proline
<220> FEATURE:
<221> NAME/KEY: MISC_FEATURE
<222> LOCATION: (4)..(4)
<223> OTHER INFORMATION: wherein Xaa = homophenylalanine
<220> FEATURE:
<221> NAME/KEY: MISC_FEATURE
<222> LOCATION: (5)..(5)
<223> OTHER INFORMATION: wherein Xaa = N,N-dimethyl-lysine

<400> SEQUENCE: 127

Xaa Leu Gly Xaa Xaa Leu
1               5

<210> SEQ ID NO 128
<211> LENGTH: 7
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = N,N-dimethylglycine
<220> FEATURE:
<221> NAME/KEY: MISC_FEATURE
<222> LOCATION: (5)..(5)
<223> OTHER INFORMATION: wherein Xaa = homophenylalanine
<220> FEATURE:
<221> NAME/KEY: MISC_FEATURE
<222> LOCATION: (6)..(6)
<223> OTHER INFORMATION: wherein Xaa = N,N-dimethyl-lysine
```

```
<400> SEQUENCE: 128

Xaa Pro Leu Gly Xaa Xaa Leu
1               5

<210> SEQ ID NO 129
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = polyethyleneglycol-proline
<220> FEATURE:
<221> NAME/KEY: MISC_FEATURE
<222> LOCATION: (4)..(4)
<223> OTHER INFORMATION: wherein Xaa = homophenylalanine
<220> FEATURE:
<221> NAME/KEY: MISC_FEATURE
<222> LOCATION: (5)..(5)
<223> OTHER INFORMATION: wherein Xaa = N,N-dimethyl-lysine

<400> SEQUENCE: 129

Xaa Leu Gly Xaa Xaa Leu
1               5

<210> SEQ ID NO 130
<211> LENGTH: 7
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-gamma-glutamic acid
<220> FEATURE:
<221> NAME/KEY: MISC_FEATURE
<222> LOCATION: (5)..(5)
<223> OTHER INFORMATION: wherein Xaa = homophenylalanine
<220> FEATURE:
<221> NAME/KEY: MISC_FEATURE
<222> LOCATION: (6)..(6)
<223> OTHER INFORMATION: wherein Xaa = N,N-dimethyl-lysine

<400> SEQUENCE: 130

Xaa Pro Leu Gly Xaa Xaa Leu
1               5

<210> SEQ ID NO 131
<211> LENGTH: 7
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = gamma-glutamic acid
<220> FEATURE:
<221> NAME/KEY: MISC_FEATURE
<222> LOCATION: (5)..(5)
<223> OTHER INFORMATION: wherein Xaa = homophenylalanine
<220> FEATURE:
<221> NAME/KEY: MISC_FEATURE
<222> LOCATION: (6)..(6)
<223> OTHER INFORMATION: wherein Xaa = N,N-dimethyl-lysine

<400> SEQUENCE: 131

Xaa Pro Leu Gly Xaa Xaa Leu
1               5
```

<210> SEQ ID NO 132
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-proline
<220> FEATURE:
<221> NAME/KEY: MISC_FEATURE
<222> LOCATION: (4)..(4)
<223> OTHER INFORMATION: wherein Xaa = homophenylalanine
<220> FEATURE:
<221> NAME/KEY: MISC_FEATURE
<222> LOCATION: (5)..(5)
<223> OTHER INFORMATION: wherein Xaa = N,N-dimethyl-lysine
<220> FEATURE:
<221> NAME/KEY: MISC_FEATURE
<222> LOCATION: (6)..(6)
<223> OTHER INFORMATION: wherein Xaa = norleucine

<400> SEQUENCE: 132

Xaa Leu Gly Xaa Xaa Xaa
1               5

<210> SEQ ID NO 133
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-proline
<220> FEATURE:
<221> NAME/KEY: MISC_FEATURE
<222> LOCATION: (4)..(4)
<223> OTHER INFORMATION: wherein Xaa = homophenylalanine
<220> FEATURE:
<221> NAME/KEY: MISC_FEATURE
<222> LOCATION: (5)..(5)
<223> OTHER INFORMATION: wherein Xaa = N, N-dimethyl-lysine
<220> FEATURE:
<221> NAME/KEY: MISC_FEATURE
<222> LOCATION: (6)..(6)
<223> OTHER INFORMATION: wherein Xaa = cyclohexylalanine

<400> SEQUENCE: 133

Xaa Leu Gly Xaa Xaa Xaa
1               5

<210> SEQ ID NO 134
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-proline
<220> FEATURE:
<221> NAME/KEY: MISC_FEATURE
<222> LOCATION: (4)..(4)
<223> OTHER INFORMATION: wherein Xaa = homophenylalanine
<220> FEATURE:
<221> NAME/KEY: MISC_FEATURE
<222> LOCATION: (5)..(5)
<223> OTHER INFORMATION: wherein Xaa = N5-aminocarbonylornithine

```
<400> SEQUENCE: 134

Xaa Leu Gly Xaa Xaa Leu
1               5

<210> SEQ ID NO 135
<211> LENGTH: 7
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-gamma-glutamic acid
<220> FEATURE:
<221> NAME/KEY: MISC_FEATURE
<222> LOCATION: (5)..(5)
<223> OTHER INFORMATION: wherein Xaa = homophenylalanine
<220> FEATURE:
<221> NAME/KEY: MISC_FEATURE
<222> LOCATION: (6)..(6)
<223> OTHER INFORMATION: wherein Xaa = N5-aminocarbonylornithine

<400> SEQUENCE: 135

Xaa Pro Leu Gly Xaa Xaa Leu
1               5

<210> SEQ ID NO 136
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-proline
<220> FEATURE:
<221> NAME/KEY: MISC_FEATURE
<222> LOCATION: (4)..(4)
<223> OTHER INFORMATION: wherein Xaa = homophenylalanine

<400> SEQUENCE: 136

Xaa Leu Gly Xaa Gln Leu
1               5

<210> SEQ ID NO 137
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-proline
<220> FEATURE:
<221> NAME/KEY: MISC_FEATURE
<222> LOCATION: (4)..(4)
<223> OTHER INFORMATION: wherein Xaa = homophenylalanine
<220> FEATURE:
<221> NAME/KEY: MISC_FEATURE
<222> LOCATION: (5)..(5)
<223> OTHER INFORMATION: wherein Xaa = 4-aza-phenylalanine

<400> SEQUENCE: 137

Xaa Leu Gly Xaa Xaa Leu
1               5

<210> SEQ ID NO 138
<211> LENGTH: 6
```

```
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-proline
<220> FEATURE:
<221> NAME/KEY: MISC_FEATURE
<222> LOCATION: (4)..(4)
<223> OTHER INFORMATION: wherein Xaa = homophenylalanine

<400> SEQUENCE: 138

Xaa Leu Gly Xaa Val Leu
1               5

<210> SEQ ID NO 139
<211> LENGTH: 7
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-gamma-glutamic acid
<220> FEATURE:
<221> NAME/KEY: MISC_FEATURE
<222> LOCATION: (5)..(5)
<223> OTHER INFORMATION: wherein Xaa = homophenylalanine

<400> SEQUENCE: 139

Xaa Pro Leu Gly Xaa Glu Leu
1               5

<210> SEQ ID NO 140
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-glycine
<220> FEATURE:
<221> NAME/KEY: MISC_FEATURE
<222> LOCATION: (2)..(2)
<223> OTHER INFORMATION: wherein Xaa = 2-carboxyazetidine

<400> SEQUENCE: 140

Xaa Xaa Leu Gly Leu Leu
1               5

<210> SEQ ID NO 141
<211> LENGTH: 5
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl- (4-fluoro-phenylalanine)

<400> SEQUENCE: 141

Xaa Leu Gly Leu Leu
1               5

<210> SEQ ID NO 142
```

```
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-homophenylalanine

<400> SEQUENCE: 142

Xaa Leu Gly Leu Tyr Leu
1               5

<210> SEQ ID NO 143
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-homophenylalanine
<220> FEATURE:
<221> NAME/KEY: MISC_FEATURE
<222> LOCATION: (4)..(4)
<223> OTHER INFORMATION: wherein Xaa = homophenylalanine
<220> FEATURE:
<221> NAME/KEY: MISC_FEATURE
<222> LOCATION: (5)..(5)
<223> OTHER INFORMATION: wherein Xaa = ornithine

<400> SEQUENCE: 143

Xaa Leu Gly Xaa Xaa Leu
1               5

<210> SEQ ID NO 144
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-2-carboxyazetidine

<400> SEQUENCE: 144

Xaa Leu Gly Leu Tyr Leu
1               5

<210> SEQ ID NO 145
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-2-carboxyazetidine
<220> FEATURE:
<221> NAME/KEY: MISC_FEATURE
<222> LOCATION: (4)..(4)
<223> OTHER INFORMATION: wherein Xaa = homophenylalanine
<220> FEATURE:
<221> NAME/KEY: MISC_FEATURE
<222> LOCATION: (5)..(5)
<223> OTHER INFORMATION: wherein Xaa = ornithine

<400> SEQUENCE: 145
```

```
Xaa Leu Gly Xaa Xaa Leu
1               5

<210> SEQ ID NO 146
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-proline

<400> SEQUENCE: 146

Xaa Leu Gly Leu Tyr Gly
1               5

<210> SEQ ID NO 147
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-proline
<220> FEATURE:
<221> NAME/KEY: MISC_FEATURE
<222> LOCATION: (4)..(4)
<223> OTHER INFORMATION: wherein Xaa = homophenylalanine

<400> SEQUENCE: 147

Xaa Leu Gly Xaa Tyr Gly
1               5

<210> SEQ ID NO 148
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-proline
<220> FEATURE:
<221> NAME/KEY: MISC_FEATURE
<222> LOCATION: (6)..(6)
<223> OTHER INFORMATION: wherein Xaa = beta-homo-leucine

<400> SEQUENCE: 148

Xaa Leu Gly Leu Tyr Xaa
1               5

<210> SEQ ID NO 149
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-proline
<220> FEATURE:
<221> NAME/KEY: MISC_FEATURE
<222> LOCATION: (4)..(4)
<223> OTHER INFORMATION: wherein Xaa = homophenylalanine
<220> FEATURE:
<221> NAME/KEY: MISC_FEATURE
```

```
<222> LOCATION: (6)..(6)
<223> OTHER INFORMATION: wherein Xaa = beta-homo-leucine

<400> SEQUENCE: 149

Xaa Leu Gly Xaa Tyr Xaa
 1               5

<210> SEQ ID NO 150
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-proline
<220> FEATURE:
<221> NAME/KEY: MISC_FEATURE
<222> LOCATION: (6)..(6)
<223> OTHER INFORMATION: wherein Xaa = beta-alanine

<400> SEQUENCE: 150

Xaa Leu Gly Leu Tyr Xaa
 1               5

<210> SEQ ID NO 151
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-proline
<220> FEATURE:
<221> NAME/KEY: MISC_FEATURE
<222> LOCATION: (6)..(6)
<223> OTHER INFORMATION: wherein Xaa = 6-aminohexanoic acid

<400> SEQUENCE: 151

Xaa Leu Gly Leu Tyr Xaa
 1               5

<210> SEQ ID NO 152
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-proline
<220> FEATURE:
<221> NAME/KEY: MISC_FEATURE
<222> LOCATION: (6)..(6)
<223> OTHER INFORMATION: wherein Xaa = 4-amino-5-phenylpentanoic acid

<400> SEQUENCE: 152

Xaa Leu Gly Leu Tyr Xaa
 1               5

<210> SEQ ID NO 153
<211> LENGTH: 6
<212> TYPE: PRT
<213> ORGANISM: Artificial
<220> FEATURE:
<223> OTHER INFORMATION: Synthetic Sequence
<220> FEATURE:
```

```
<221> NAME/KEY: MISC_FEATURE
<222> LOCATION: (1)..(1)
<223> OTHER INFORMATION: wherein Xaa = acetyl-proline
<220> FEATURE:
<221> NAME/KEY: MISC_FEATURE
<222> LOCATION: (6)..(6)
<223> OTHER INFORMATION: wherein Xaa = 4-amino-7-methylheptanoic acid

<400> SEQUENCE: 153

Xaa Leu Gly Leu Tyr Xaa
1               5

<210> SEQ ID NO 154
<211> LENGTH: 7
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-proline

<400> SEQUENCE: 154

Xaa Leu Gly Leu Leu Ala Leu
1               5

<210> SEQ ID NO 155
<211> LENGTH: 7
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-proline

<400> SEQUENCE: 155

Xaa Leu Gly Leu Tyr Ala Leu
1               5

<210> SEQ ID NO 156
<211> LENGTH: 7
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-glycine

<400> SEQUENCE: 156

Xaa Pro Leu Gly Leu Ala Leu
1               5

<210> SEQ ID NO 157
<211> LENGTH: 7
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-proline

<400> SEQUENCE: 157

Xaa Leu Gly Leu Ala Ala Leu
```

```
1               5

<210> SEQ ID NO 158
<211> LENGTH: 7
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-proline

<400> SEQUENCE: 158

Xaa Leu Gly Leu Ala Leu Leu
1               5

<210> SEQ ID NO 159
<211> LENGTH: 7
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-proline

<400> SEQUENCE: 159

Xaa Leu Gly Leu Leu Ser Leu
1               5

<210> SEQ ID NO 160
<211> LENGTH: 7
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-proline

<400> SEQUENCE: 160

Xaa Leu Gly Leu Leu Leu Leu
1               5

<210> SEQ ID NO 161
<211> LENGTH: 7
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = N,N-dimethylglycine

<400> SEQUENCE: 161

Xaa Pro Leu Gly Leu Tyr Leu
1               5

<210> SEQ ID NO 162
<211> LENGTH: 7
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
```

```
<222> LOCATION: (1)..(1)
<223> OTHER INFORMATION: wherein Xaa = N,N-dimethylglycine
<220> FEATURE:
<221> NAME/KEY: MISC_FEATURE
<222> LOCATION: (5)..(5)
<223> OTHER INFORMATION: wherein Xaa = 2-phenylglycine

<400> SEQUENCE: 162

Xaa Pro Arg Gly Xaa Tyr Leu
1               5

<210> SEQ ID NO 163
<211> LENGTH: 7
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-glycine

<400> SEQUENCE: 163

Xaa Pro Leu Gly Leu Arg Leu
1               5

<210> SEQ ID NO 164
<211> LENGTH: 4
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = 4-(2-(5,6,7,8-
     tetrahydronaphthenyl))butyl-glycine
<220> FEATURE:
<221> NAME/KEY: MISC_FEATURE
<222> LOCATION: (2)..(2)
<223> OTHER INFORMATION: wherein Xaa = homophenylalanine

<400> SEQUENCE: 164

Xaa Xaa Tyr Leu
1

<210> SEQ ID NO 165
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-proline
<220> FEATURE:
<221> NAME/KEY: MISC_FEATURE
<222> LOCATION: (4)..(4)
<223> OTHER INFORMATION: wherein Xaa = homophenylalanine
<220> FEATURE:
<221> NAME/KEY: MISC_FEATURE
<222> LOCATION: (5)..(5)
<223> OTHER INFORMATION: wherein Xaa = N-methylpiperazinepropyl-glycine

<400> SEQUENCE: 165

Xaa Leu Gly Xaa Xaa Leu
1               5

<210> SEQ ID NO 166
<211> LENGTH: 6
```

```
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = tetrazoleacetyl-proline
<220> FEATURE:
<221> NAME/KEY: MISC_FEATURE
<222> LOCATION: (4)..(4)
<223> OTHER INFORMATION: wherein Xaa = homophenylalanine

<400> SEQUENCE: 166

Xaa Leu Gly Xaa Tyr Leu
1               5

<210> SEQ ID NO 167
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = tetrazoleacetyl-proline
<220> FEATURE:
<221> NAME/KEY: MISC_FEATURE
<222> LOCATION: (4)..(4)
<223> OTHER INFORMATION: wherein Xaa = O-benzyl-serine

<400> SEQUENCE: 167

Xaa Leu Gly Xaa Tyr Leu
1               5

<210> SEQ ID NO 168
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = tetrazoleacetyl-proline
<220> FEATURE:
<221> NAME/KEY: MISC_FEATURE
<222> LOCATION: (4)..(4)
<223> OTHER INFORMATION: wherein Xaa = homophenylalanine
<220> FEATURE:
<221> NAME/KEY: MISC_FEATURE
<222> LOCATION: (6)..(6)
<223> OTHER INFORMATION: wherein Xaa = norleucine

<400> SEQUENCE: 168

Xaa Leu Gly Xaa Tyr Xaa
1               5

<210> SEQ ID NO 169
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (4)..(4)
<223> OTHER INFORMATION: wherein Xaa = O-benzyl-serine

<400> SEQUENCE: 169

Pro Leu Gly Xaa Tyr Leu
```

```
1               5

<210> SEQ ID NO 170
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-proline
<220> FEATURE:
<221> NAME/KEY: MISC_FEATURE
<222> LOCATION: (4)..(4)
<223> OTHER INFORMATION: wherein Xaa = homophenylalanine
<220> FEATURE:
<221> NAME/KEY: MISC_FEATURE
<222> LOCATION: (5)..(5)
<223> OTHER INFORMATION: wherein Xaa = homo-tyrosine

<400> SEQUENCE: 170

Xaa Leu Gly Xaa Xaa Leu
1               5

<210> SEQ ID NO 171
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-proline
<220> FEATURE:
<221> NAME/KEY: MISC_FEATURE
<222> LOCATION: (2)..(2)
<223> OTHER INFORMATION: wherein Xaa = 4-aza-hydroxy-phenylalanine
<220> FEATURE:
<221> NAME/KEY: MISC_FEATURE
<222> LOCATION: (4)..(4)
<223> OTHER INFORMATION: wherein Xaa = 4-aza-hydroxy-phenylalanine

<400> SEQUENCE: 171

Xaa Xaa Gly Xaa Tyr Leu
1               5

<210> SEQ ID NO 172
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-proline
<220> FEATURE:
<221> NAME/KEY: MISC_FEATURE
<222> LOCATION: (4)..(4)
<223> OTHER INFORMATION: wherein Xaa = O-allyl-serine

<400> SEQUENCE: 172

Xaa Leu Gly Xaa Tyr Leu
1               5

<210> SEQ ID NO 173
<211> LENGTH: 6
<212> TYPE: PRT
<213> ORGANISM: Artificial
<220> FEATURE:
```

```
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-proline
<220> FEATURE:
<221> NAME/KEY: MISC_FEATURE
<222> LOCATION: (4)..(4)
<223> OTHER INFORMATION: wherein Xaa = 4-nitro-homophenylalanine

<400> SEQUENCE: 173

Xaa Leu Gly Xaa Tyr Leu
1               5

<210> SEQ ID NO 174
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-proline
<220> FEATURE:
<221> NAME/KEY: MISC_FEATURE
<222> LOCATION: (4)..(4)
<223> OTHER INFORMATION: wherein Xaa = homophenylalanine
<220> FEATURE:
<221> NAME/KEY: MISC_FEATURE
<222> LOCATION: (5)..(5)
<223> OTHER INFORMATION: wherein Xaa = 4-aza-hydroxy-phenylalanine

<400> SEQUENCE: 174

Xaa Leu Gly Xaa Xaa Leu
1               5

<210> SEQ ID NO 175
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-proline
<220> FEATURE:
<221> NAME/KEY: MISC_FEATURE
<222> LOCATION: (4)..(4)
<223> OTHER INFORMATION: wherein Xaa = O-methyl-serine

<400> SEQUENCE: 175

Xaa Leu Gly Xaa Tyr Leu
1               5

<210> SEQ ID NO 176
<211> LENGTH: 7
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-gamma-glutamic acid
<220> FEATURE:
<221> NAME/KEY: MISC_FEATURE
<222> LOCATION: (5)..(5)
<223> OTHER INFORMATION: wherein Xaa = O-benzyl-serine

<400> SEQUENCE: 176
```

```
Xaa Pro Leu Gly Xaa Tyr Leu
1               5
```

<210> SEQ ID NO 177
<211> LENGTH: 7
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-gamma-glutamic acid
<220> FEATURE:
<221> NAME/KEY: MISC_FEATURE
<222> LOCATION: (5)..(5)
<223> OTHER INFORMATION: wherein Xaa = O-benzyl-serine
<220> FEATURE:
<221> NAME/KEY: MISC_FEATURE
<222> LOCATION: (7)..(7)
<223> OTHER INFORMATION: wherein Xaa = norleucine

<400> SEQUENCE: 177

```
Xaa Pro Leu Gly Xaa Tyr Xaa
1               5
```

<210> SEQ ID NO 178
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = 3-pyridinecarbonyl-proline
<220> FEATURE:
<221> NAME/KEY: MISC_FEATURE
<222> LOCATION: (4)..(4)
<223> OTHER INFORMATION: wherein Xaa = homophenylalanine

<400> SEQUENCE: 178

```
Xaa Leu Gly Xaa Tyr Leu
1               5
```

<210> SEQ ID NO 179
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = 2-pyrazinecarbonyl-proline
<220> FEATURE:
<221> NAME/KEY: MISC_FEATURE
<222> LOCATION: (4)..(4)
<223> OTHER INFORMATION: wherein Xaa = homophenylalanine

<400> SEQUENCE: 179

```
Xaa Leu Gly Xaa Tyr Leu
1               5
```

<210> SEQ ID NO 180
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE

```
<222> LOCATION: (1)..(1)
<223> OTHER INFORMATION: wherein Xaa = acetyl-proline
<220> FEATURE:
<221> NAME/KEY: MISC_FEATURE
<222> LOCATION: (4)..(4)
<223> OTHER INFORMATION: wherein Xaa = homophenylalanine
<220> FEATURE:
<221> NAME/KEY: MISC_FEATURE
<222> LOCATION: (5)..(5)
<223> OTHER INFORMATION: wherein Xaa = dimethyl-lysine
<220> FEATURE:
<221> NAME/KEY: MISC_FEATURE
<222> LOCATION: (6)..(6)
<223> OTHER INFORMATION: wherein Xaa = norleucine

<400> SEQUENCE: 180

Xaa Leu Gly Xaa Xaa Xaa
1               5

<210> SEQ ID NO 181
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-proline
<220> FEATURE:
<221> NAME/KEY: MISC_FEATURE
<222> LOCATION: (4)..(4)
<223> OTHER INFORMATION: wherein Xaa = homophenylalanine
<220> FEATURE:
<221> NAME/KEY: MISC_FEATURE
<222> LOCATION: (6)..(6)
<223> OTHER INFORMATION: wherein Xaa = homoserine

<400> SEQUENCE: 181

Xaa Leu Gly Xaa Tyr Xaa
1               5

<210> SEQ ID NO 182
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-proline
<220> FEATURE:
<221> NAME/KEY: MISC_FEATURE
<222> LOCATION: (4)..(4)
<223> OTHER INFORMATION: wherein Xaa = homo-phenylalanine
<220> FEATURE:
<221> NAME/KEY: MISC_FEATURE
<222> LOCATION: (6)..(6)
<223> OTHER INFORMATION: wherein Xaa = homo-leucine

<400> SEQUENCE: 182

Xaa Leu Gly Xaa Tyr Xaa
1               5

<210> SEQ ID NO 183
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
```

```
<222> LOCATION: (1)..(1)
<223> OTHER INFORMATION: wherein Xaa = acetyl-proline
<220> FEATURE:
<221> NAME/KEY: MISC_FEATURE
<222> LOCATION: (4)..(4)
<223> OTHER INFORMATION: wherein Xaa = O-benzyl-threonine

<400> SEQUENCE: 183

Xaa Leu Gly Xaa Tyr Leu
1               5

<210> SEQ ID NO 184
<211> LENGTH: 7
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-gamma-glutamic acid
<220> FEATURE:
<221> NAME/KEY: MISC_FEATURE
<222> LOCATION: (5)..(5)
<223> OTHER INFORMATION: wherein Xaa = homophenylalanine
<220> FEATURE:
<221> NAME/KEY: MISC_FEATURE
<222> LOCATION: (7)..(7)
<223> OTHER INFORMATION: wherein Xaa = norleucine

<400> SEQUENCE: 184

Xaa Pro Leu Gly Xaa Tyr Xaa
1               5

<210> SEQ ID NO 185
<211> LENGTH: 7
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = gamma-glutamic acid
<220> FEATURE:
<221> NAME/KEY: MISC_FEATURE
<222> LOCATION: (3)..(3)
<223> OTHER INFORMATION: wherein Xaa = ornithine
<220> FEATURE:
<221> NAME/KEY: MISC_FEATURE
<222> LOCATION: (5)..(5)
<223> OTHER INFORMATION: wherein Xaa = homophenylalanine

<400> SEQUENCE: 185

Xaa Pro Xaa Gly Xaa Glu Leu
1               5

<210> SEQ ID NO 186
<211> LENGTH: 7
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = gamma glutamic acid
<220> FEATURE:
<221> NAME/KEY: MISC_FEATURE
<222> LOCATION: (5)..(5)
<223> OTHER INFORMATION: wherein Xaa = O-benzyl-serine

<400> SEQUENCE: 186
```

```
Xaa Pro Leu Gly Xaa Tyr Leu
1               5
```

<210> SEQ ID NO 187
<211> LENGTH: 7
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = gamma-glutamic acid
<220> FEATURE:
<221> NAME/KEY: MISC_FEATURE
<222> LOCATION: (5)..(5)
<223> OTHER INFORMATION: wherein Xaa = O-benzyl-serine
<220> FEATURE:
<221> NAME/KEY: MISC_FEATURE
<222> LOCATION: (7)..(7)
<223> OTHER INFORMATION: wherein Xaa = norleucine

<400> SEQUENCE: 187

```
Xaa Pro Leu Gly Xaa Tyr Xaa
1               5
```

<210> SEQ ID NO 188
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (4)..(4)
<223> OTHER INFORMATION: wherein Xaa = O-benzyl-serine

<400> SEQUENCE: 188

```
Pro Leu Gly Xaa Tyr Leu
1               5
```

<210> SEQ ID NO 189
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (4)..(4)
<223> OTHER INFORMATION: O-methyl-serine

<400> SEQUENCE: 189

```
Pro Leu Gly Xaa Tyr Leu
1               5
```

<210> SEQ ID NO 190
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (4)..(4)
<223> OTHER INFORMATION: wherein Xaa = 4-aza-hydroxy-phenylalanine

<400> SEQUENCE: 190

```
Pro Leu Gly Xaa Tyr Leu
1               5
```

-continued

```
<210> SEQ ID NO 191
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (4)..(4)
<223> OTHER INFORMATION: wherein Xaa = homophenylalanine

<400> SEQUENCE: 191

Pro Leu Gly Xaa Tyr Leu
1               5

<210> SEQ ID NO 192
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (4)..(4)
<223> OTHER INFORMATION: wherein Xaa = homophenylalanine

<400> SEQUENCE: 192

Pro Leu Gly Xaa Glu Leu
1               5

<210> SEQ ID NO 193
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (4)..(4)
<223> OTHER INFORMATION: wherein Xaa = O-benzyl-serine
<220> FEATURE:
<221> NAME/KEY: MISC_FEATURE
<222> LOCATION: (6)..(6)
<223> OTHER INFORMATION: wherein Xaa = norleucine

<400> SEQUENCE: 193

Pro Leu Gly Xaa Tyr Xaa
1               5

<210> SEQ ID NO 194
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (4)..(4)
<223> OTHER INFORMATION: wherein Xaa = O-methyl-serine
<220> FEATURE:
<221> NAME/KEY: MISC_FEATURE
<222> LOCATION: (6)..(6)
<223> OTHER INFORMATION: wherein Xaa = norleucine

<400> SEQUENCE: 194

Pro Leu Gly Xaa Tyr Xaa
1               5

<210> SEQ ID NO 195
```

```
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (4)..(4)
<223> OTHER INFORMATION: wherein Xaa = 4-aza-hydroxy-phenylalanine
<220> FEATURE:
<221> NAME/KEY: MISC_FEATURE
<222> LOCATION: (6)..(6)
<223> OTHER INFORMATION: wherein Xaa = norleucine

<400> SEQUENCE: 195

Pro Leu Gly Xaa Tyr Xaa
1               5

<210> SEQ ID NO 196
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (4)..(4)
<223> OTHER INFORMATION: wherein Xaa = homophenylalanine
<220> FEATURE:
<221> NAME/KEY: MISC_FEATURE
<222> LOCATION: (6)..(6)
<223> OTHER INFORMATION: wherein Xaa = norleucine

<400> SEQUENCE: 196

Pro Leu Gly Xaa Tyr Xaa
1               5

<210> SEQ ID NO 197
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (4)..(4)
<223> OTHER INFORMATION: wherein Xaa = homophenylalanine
<220> FEATURE:
<221> NAME/KEY: MISC_FEATURE
<222> LOCATION: (6)..(6)
<223> OTHER INFORMATION: wherein Xaa = norleucine

<400> SEQUENCE: 197

Pro Leu Gly Xaa Glu Xaa
1               5

<210> SEQ ID NO 198
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (4)..(4)
<223> OTHER INFORMATION: wherein Xaa = O-benzyl-serine
<220> FEATURE:
<221> NAME/KEY: MISC_FEATURE
<222> LOCATION: (6)..(6)
<223> OTHER INFORMATION: wherein Xaa = homoleucine

<400> SEQUENCE: 198
```

Pro Leu Gly Xaa Tyr Xaa
1               5

<210> SEQ ID NO 199
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (4)..(4)
<223> OTHER INFORMATION: wherein Xaa = O-methyl-serine
<220> FEATURE:
<221> NAME/KEY: MISC_FEATURE
<222> LOCATION: (6)..(6)
<223> OTHER INFORMATION: wherein Xaa = homoleucine

<400> SEQUENCE: 199

Pro Leu Gly Xaa Tyr Xaa
1               5

<210> SEQ ID NO 200
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (4)..(4)
<223> OTHER INFORMATION: wherein Xaa = 4-aza-hydroxy-phenylalanine
<220> FEATURE:
<221> NAME/KEY: MISC_FEATURE
<222> LOCATION: (6)..(6)
<223> OTHER INFORMATION: wherein Xaa = homoleucine

<400> SEQUENCE: 200

Pro Leu Gly Xaa Tyr Xaa
1               5

<210> SEQ ID NO 201
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (4)..(4)
<223> OTHER INFORMATION: wherein Xaa = homophenylalanine
<220> FEATURE:
<221> NAME/KEY: MISC_FEATURE
<222> LOCATION: (6)..(6)
<223> OTHER INFORMATION: wherein Xaa = homoleucine

<400> SEQUENCE: 201

Pro Leu Gly Xaa Tyr Xaa
1               5

<210> SEQ ID NO 202
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (4)..(4)
<223> OTHER INFORMATION: wherein Xaa = homophenylalanine
<220> FEATURE:
<221> NAME/KEY: MISC_FEATURE

```
<222> LOCATION: (6)..(6)
<223> OTHER INFORMATION: wherein Xaa = homoleucine

<400> SEQUENCE: 202

Pro Leu Gly Xaa Glu Xaa
1               5

<210> SEQ ID NO 203
<211> LENGTH: 4
<212> TYPE: PRT
<213> ORGANISM: Artificial
<220> FEATURE:
<223> OTHER INFORMATION: Synthetic Sequence

<400> SEQUENCE: 203

Pro Leu Gly Leu
1

<210> SEQ ID NO 204
<211> LENGTH: 7
<212> TYPE: PRT
<213> ORGANISM: Artificial
<220> FEATURE:
<223> OTHER INFORMATION: Synthetic Sequence

<400> SEQUENCE: 204

Pro Leu Gly Leu Leu Tyr Leu
1               5

<210> SEQ ID NO 205
<211> LENGTH: 5
<212> TYPE: PRT
<213> ORGANISM: Artificial
<220> FEATURE:
<223> OTHER INFORMATION: Synthetic Sequence

<400> SEQUENCE: 205

Gly Pro Leu Gly Leu
1               5

<210> SEQ ID NO 206
<211> LENGTH: 5
<212> TYPE: PRT
<213> ORGANISM: Artificial
<220> FEATURE:
<223> OTHER INFORMATION: Synthetic Sequence

<400> SEQUENCE: 206

Asp Pro Leu Gly Leu
1               5

<210> SEQ ID NO 207
<211> LENGTH: 5
<212> TYPE: PRT
<213> ORGANISM: Artificial
<220> FEATURE:
<223> OTHER INFORMATION: Synthetic Sequence

<400> SEQUENCE: 207

Pro Glu Gln Gly Leu
1               5

<210> SEQ ID NO 208
<211> LENGTH: 4
<212> TYPE: PRT
<213> ORGANISM: Artificial
<220> FEATURE:
```

<223> OTHER INFORMATION: Synthetic Sequence

<400> SEQUENCE: 208

Pro Gln Gly Leu
1

<210> SEQ ID NO 209
<211> LENGTH: 7
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (5)..(5)
<223> OTHER INFORMATION: wherein Xaa = diphenylalanine

<400> SEQUENCE: 209

Pro Leu Gly Leu Xaa Ala Arg
1               5

<210> SEQ ID NO 210
<211> LENGTH: 4
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (4)..(4)
<223> OTHER INFORMATION: wherein Xaa = homophenylalanine

<400> SEQUENCE: 210

Pro Leu Gly Xaa
1

<210> SEQ ID NO 211
<211> LENGTH: 7
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl-histidine

<400> SEQUENCE: 211

Xaa Ser Ser Lys Leu Gln Leu
1               5

<210> SEQ ID NO 212
<211> LENGTH: 5
<212> TYPE: PRT
<213> ORGANISM: Artificial
<220> FEATURE:
<223> OTHER INFORMATION: Synthetic Sequence

<400> SEQUENCE: 212

Pro Leu Gly Leu Leu
1               5

<210> SEQ ID NO 213
<211> LENGTH: 6
<212> TYPE: PRT
<213> ORGANISM: Artificial
<220> FEATURE:
<223> OTHER INFORMATION: Synthetic Sequence

```
<400> SEQUENCE: 213

Pro Leu Gly Leu Ala Leu
1               5

<210> SEQ ID NO 214
<211> LENGTH: 6
<212> TYPE: PRT
<213> ORGANISM: Artificial
<220> FEATURE:
<223> OTHER INFORMATION: Synthetic Sequence

<400> SEQUENCE: 214

Pro Leu Gly Leu Tyr Leu
1               5

<210> SEQ ID NO 215
<211> LENGTH: 7
<212> TYPE: PRT
<213> ORGANISM: Artificial
<220> FEATURE:
<223> OTHER INFORMATION: Synthetic Sequence

<400> SEQUENCE: 215

Pro Leu Gly Leu Tyr Ala Leu
1               5

<210> SEQ ID NO 216
<211> LENGTH: 7
<212> TYPE: PRT
<213> ORGANISM: Artificial
<220> FEATURE:
<223> OTHER INFORMATION: Synthetic Sequence

<400> SEQUENCE: 216

Pro Leu Gly Leu Ala Ala Leu
1               5

<210> SEQ ID NO 217
<211> LENGTH: 7
<212> TYPE: PRT
<213> ORGANISM: Artificial
<220> FEATURE:
<223> OTHER INFORMATION: Synthetic Sequence

<400> SEQUENCE: 217

Pro Leu Gly Leu Leu Ser Leu
1               5

<210> SEQ ID NO 218
<211> LENGTH: 7
<212> TYPE: PRT
<213> ORGANISM: Artificial
<220> FEATURE:
<223> OTHER INFORMATION: Synthetic Sequence

<400> SEQUENCE: 218

Pro Leu Gly Leu Leu Ala Leu
1               5

<210> SEQ ID NO 219
<211> LENGTH: 6
<212> TYPE: PRT
<213> ORGANISM: Artificial
<220> FEATURE:
<223> OTHER INFORMATION: Synthetic Sequence

<400> SEQUENCE: 219
```

```
Gly Pro Leu Gly Leu Leu
1               5
```

<210> SEQ ID NO 220
<211> LENGTH: 4
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (4)..(4)
<223> OTHER INFORMATION: wherein Xaa = O-benzyl serine

<400> SEQUENCE: 220

```
Pro Leu Gly Xaa
1
```

<210> SEQ ID NO 221
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (4)..(4)
<223> OTHER INFORMATION: wherein Xaa = homophenylalanine

<400> SEQUENCE: 221

```
Pro Leu Gly Xaa Tyr Leu
1               5
```

<210> SEQ ID NO 222
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (4)..(4)
<223> OTHER INFORMATION: wherein Xaa = O-benzyl serine

<400> SEQUENCE: 222

```
Pro Leu Gly Xaa Tyr Leu
1               5
```

<210> SEQ ID NO 223
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (4)..(4)
<223> OTHER INFORMATION: wherein Xaa = homophenylalanine

<400> SEQUENCE: 223

```
Pro Leu Gly Xaa Glu Leu
1               5
```

<210> SEQ ID NO 224
<211> LENGTH: 7
<212> TYPE: PRT
<213> ORGANISM: Artificial
<220> FEATURE:
<223> OTHER INFORMATION: Synthetic Sequence

```
<400> SEQUENCE: 224

Gly Pro Leu Gly Leu Ala Leu
1               5

<210> SEQ ID NO 225
<211> LENGTH: 4
<212> TYPE: PRT
<213> ORGANISM: Artificial
<220> FEATURE:
<223> OTHER INFORMATION: Synthetic Sequence

<400> SEQUENCE: 225

Gly Gly Arg Leu
1

<210> SEQ ID NO 226
<211> LENGTH: 4
<212> TYPE: PRT
<213> ORGANISM: Artificial
<220> FEATURE:
<223> OTHER INFORMATION: Synthetic Sequence

<400> SEQUENCE: 226

Gly Val Phe Arg
1

<210> SEQ ID NO 227
<211> LENGTH: 4
<212> TYPE: PRT
<213> ORGANISM: Artificial
<220> FEATURE:
<223> OTHER INFORMATION: Synthetic Sequence

<400> SEQUENCE: 227

Ala Pro Gly Leu
1

<210> SEQ ID NO 228
<211> LENGTH: 4
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = 2-thienylalanine

<400> SEQUENCE: 228

Xaa Gly Ala Leu
1

<210> SEQ ID NO 229
<211> LENGTH: 4
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = 2-naphthylalanine

<400> SEQUENCE: 229

Xaa Gly Ala Leu
1
```

```
<210> SEQ ID NO 230
<211> LENGTH: 4
<212> TYPE: PRT
<213> ORGANISM: Artificial
<220> FEATURE:
<223> OTHER INFORMATION: Synthetic Sequence

<400> SEQUENCE: 230

Gly Leu Gly Leu
1

<210> SEQ ID NO 231
<211> LENGTH: 6
<212> TYPE: PRT
<213> ORGANISM: Artificial
<220> FEATURE:
<223> OTHER INFORMATION: Synthetic Sequence

<400> SEQUENCE: 231

Gly Pro Leu Gly Leu Tyr
1               5

<210> SEQ ID NO 232
<211> LENGTH: 7
<212> TYPE: PRT
<213> ORGANISM: Artificial
<220> FEATURE:
<223> OTHER INFORMATION: Synthetic Sequence

<400> SEQUENCE: 232

Pro Leu Gly Leu Ala Leu Leu
1               5

<210> SEQ ID NO 233
<211> LENGTH: 7
<212> TYPE: PRT
<213> ORGANISM: Artificial
<220> FEATURE:
<223> OTHER INFORMATION: Synthetic Sequence

<400> SEQUENCE: 233

Pro Leu Gly Leu Leu Leu Leu
1               5

<210> SEQ ID NO 234
<211> LENGTH: 7
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = 4-hydroxyproline

<400> SEQUENCE: 234

Xaa Pro Leu Gly Leu Tyr Leu
1               5

<210> SEQ ID NO 235
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
```

-continued

<223> OTHER INFORMATION: wherein Xaa = acetyl proline

<400> SEQUENCE: 235

Xaa Leu Gly Leu Tyr Leu
1               5

<210> SEQ ID NO 236
<211> LENGTH: 7
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl 4-hydroxyproline

<400> SEQUENCE: 236

Xaa Pro Leu Gly Leu Tyr Leu
1               5

<210> SEQ ID NO 237
<211> LENGTH: 5
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl proline

<400> SEQUENCE: 237

Xaa Pro Leu Gly Leu
1               5

<210> SEQ ID NO 238
<211> LENGTH: 4
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl proline

<400> SEQUENCE: 238

Xaa Leu Gly Leu
1

<210> SEQ ID NO 239
<211> LENGTH: 5
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = acetyl glycine

<400> SEQUENCE: 239

Xaa Pro Leu Gly Leu
1               5

<210> SEQ ID NO 240
<211> LENGTH: 5
<212> TYPE: PRT

```
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: wherein Xaa = Fmoc-4-(2-aminoethyl)-1-
      carboxymethyl piperazine proline

<400> SEQUENCE: 240

Xaa Leu Gly Leu Leu
1               5
```

PEPTIDASE-CLEAVABLE, TARGETED ANTINEOPLASTIC DRUGS AND THEIR THERAPEUTIC USE

FIELD OF THE INVENTION

This invention is directed to antineoplastic agents conjugated to enzyme-cleavable peptides comprising the amino acid recognition sequence of a membrane-bound and/or cell-secreted peptidase, and to the use of such conjugated compounds as chemotherapeutic agents in the targeted treatment of cancers.

BACKGROUND OF THE INVENTION

Many anti-tumor compounds are restricted in their use because of their narrow therapeutic index, that is, the toxicities induced when the compounds are administered above certain dose levels outweigh the benefits thereby afforded. Anthracycline (e.g. doxorubicin) therapy, for example, is limited in that administration of the drug at levels in excess of cumulative 500 to 550 mg doxorubicin/$m^2$ produces a substantial risk of cardiotoxicity and myelosuppression (von Hoff, et al.). However, compounds such as doxorubicin often remain the drug of choice for particular forms of chemotherapy; therefore it would be quite useful to develop means of lowering the compounds' toxicities whilst maintaining their therapeutic potential.

One means of approaching this objective that has been tried for several decades is the design of prodrug molecules that are differentially activated in tumor tissue, that is, drug molecules inactive or significantly less active upon administration that are selectively processed in tumor tissue so as to be therapeutically active therein. Leu-Dox (the amino acid leucine conjugated to the anthracycline doxorubicin), for example, is a prodrug found to require hydrolysis of the amino acid from the prodrug by intracellular proteases in order to release the anthracycline (Boven, et al. (1990)). Conversion of Leu-Dox to Dox in mice occurs rapidly, although incompletely, to approximately 20% overall conversion (de Jong, et al. (1992 a)). A similar observation has been made upon administration of Leu-Dox to humans (de Jong, et al. (1992 b); Canal, et al.); in a Phase I trial, approximately 25% conversion of Leu-Dox to Dox occurred rapidly in the tumor tissue. Moreover, in a human ovarian tumor xenograft mouse model, Leu-Dox has been shown to be a more effective anti-tumor agent than free doxorubicin, at equitoxic doses (Boven et al. (1992)).

Conjugation of additional amino acids to Leu-Dox may further decrease the availability of this compound to cells which do not secrete the requisite protease, and hence, further limits the compound's activity outside of tumors. In this regard, for example, Denmeade et al. have shown that a peptide-doxorubicin pro-drug targeted to the prostate-specific antigen ("PSA"). Ac-HSSKLQ-Leu-Dox (SEQ ID NO: 211) is a substrate for the PSA protease and is active against prostate tumor cells which express the protease activity. Furthermore, other mono and dipeptide conjugates on anthracyclines in addition to Leu-Dox have also been shown to have biological activity (Masquelier, et al.; Baurain, et al.). While a comprehensive analysis of dipeptide-anthracycline conjugates has not been reported, compounds consisting of Leu-Leu-Daunorubicin, Ala-Leu-Daunorubicin, and Leu-Ala-Daunorubicin have been shown to have considerable biological activity.

Various matrix-metalloproteinases ("MMPs") have been described, and have had associated with them identifiable peptide cleavage sites (Nagase, et al.; McGeehan, et. al.). Moreover, the association between metastatic tumor progression has been made. In this regard, multiple researchers have shown that the enzymes MMP-2, MMP-9 and, more recently, MMP-14 (MT1–MMP) are associated with tumor progression (see, e.g., McDonnell and Fingleton; MacDougall and Matrisian). Increased expression of MMP-2 has also been reported in lung, stomach and breast carcinomas as compared to corresponding normal tissues. Increased expression of MMPs is not limited to the tumor itself. Increased expression of MMP-2 and MMP-14 has been observed in stromal and endothelial cells which are proximal to the tumor (e.g., Soini, Brummer). Thus, the level of MMP expressed is elevated at the tumor site.

Elevated expression of MMPs in tumor and supporting tissues implies that elevated activity is also present. While pro-forms of MMP-2 and MMP-9 enzyme are secreted by cells and readily detected in human serum and urine (Garbisa, et al.; Moses, et al.), the active form of the enzyme is found on the cell surface. In the case of MMP-2, the pro-form can be activated at the cell surface by the transmembrane enzyme, MMP-14 (Sato, et al.; Kurschatt, et al.). Activation of pro-MMP-2 has also been described to occur through binding of the preform of the enzyme to an integrin (Brooks, et al.). Activation of MMP-9 has been shown to occur through specific binding to the cell surface antigen, CD-44 (Yu and Stamenkovic). Based on these findings, it is anticipated that elevated MMP protease activity will be highest on the surface of tumor cells, so differential activation of the pro-drugs will be highest at the tumor site.

Safavy et al. (A. Safavy et al. (J. Med. Chem. 42:49194924 (1999)) describe the attachment of a seven amino acid synthetic peptide to the antitumor agent paclitaxel.

Trouet and Baurain describe tumor-activated prodrug compounds in U.S. Pat. No. 5,962,216, issued Oct. 5, 1999.

WO 99/02175, WO 98/18493 and WO 98/10651 conjugate certain prostate specific antigen ("PSA") cleavable peptides to cytotoxic agents.

WO 98/16240 attaches peptides to lipids, for subsequent inclusion of the resulting conjugates in liposomes so as to target delivery of the vesicles' cytotoxic agent contents to tumors.

WO 00/33888 describes peptide conjugates of doxorubicin that are processed by an enzyme called trouase.

WO 00/21571 describes the use of FAP (Fibroblast Activation Protein) to deliver doxorubicin to tumors.

WO 00/64486 claims MMP activated conjugates for delivery of substances to tumors.

However, there remains a need to develop chemotherapeutic prodrug compounds which are inactive or significantly less active upon administration, thereby lowering the compounds' toxicities, that are selectively processed in or near tumor tissue so as to become therapeutically active anticancer agents.

The current invention discloses novel compounds useful for the treatment of cancer which comprises a matrix metalloproteinase (MMP) enzyme-cleavable peptide conjugated to doxorubicin. Furthermore, the current invention discloses novel compounds useful for the treatment of cancer which upon cleavage by a matrix metalloproteinase produces a second peptide doxorubicin substrate which can be further cleaved or processed by aminopeptidases expressed in the tumor environment. None of the references above suggest the compounds of the current invention.

SUMMARY OF THE INVENTION

This invention provides a compound comprising an enzyme-cleavable peptide conjugated to an antineoplastic agent, e.g., an anthracycline, vinca alkaloid, bleomycin, mitomycin, taxane, cytotoxic nucleotide, pteridine, or podophyllotoxin. An enzyme-cleavable peptide is a peptide comprising an amino acid sequence capable of being selectively recognized and cleaved by a membrane-bound and/or cell-secreted peptidase, for example a matrix metalloproteinase. Such compounds are useful in the treatment of cancer.

Also provided herein is a pharmaceutical composition comprising said compounds and a pharmaceutically acceptable carrier. Further provided herein is a method of delivering compounds of this invention to the cells of a mammal afflicted with a cancer, or other disorder, which comprises contacting the cells with the compound in the presence of a peptidase capable of cleaving the peptide.

It is appreciated that certain features of the invention, which are for clarity, described in the context of separate embodiments, may also be provided in combination in a single embodiment. Conversely, various features of the invention, which are for brevity, described in the context of a single embodiment, may also be provided for separately or in any suitable subcombination.

DETAILED DESCRIPTION OF THE INVENTION

This invention provides a compound comprising an antineoplastic agent conjugated to an enzyme-cleavable peptide.

In a first embodiment the invention provides a compound of Formula (I):

$E^{cp}$-A (I)

or a pharmaceutically acceptable salt form thereof, wherein;

$E^{CP}$ is an enzyme cleavable peptide conjugated to A and selected from:
Cap-Paa-Xa2-Gly-Xp1-Laa-;
  Cap-Xa2-Gly-Xp1-Laa-;
Cap-Paa-Xa2-Gly-Xp1-Xp2-Laa-;
  Cap-Xa2-Gly-Xp1-Xp2-Laa-;
    Cap-Gly-Xp1-Xp2-Laa-;
Cap-Paa-Xa2-Gly-Xp1-Xp2-Xp3-Laa-;
  Cap-Xa2-Gly-Xp1-Xp2-Xp3-Laa-;
    Cap-Gly-Xp1-Xp2-Xp3-Laa-;
    Cap Paa-Xa2-Sar-Xp1-Laa-;
      Cap Xa2-Sar-Xp1-Laa-;
Cap-Paa-Xa2-Sar-Xp1-Xp2-Laa-;
  Cap-Xa2-Sar-Xp1-Xp2-Laa-;
    Cap-Sar-Xp1-Xp2-Laa-;
Cap-Paa-Xa2-Sar-Xp1-Xp2-Xp3-Laa-;
  Cap-Xa2-Sar-Xp1-Xp2-Xp3-Laa-; and
    Cap-Sar-Xp1-Xp2-Xp3-Laa-;

Paa is a Pro, Hyp, Aze, homo-Pro, Chg, Fph, Npa, Tzc, or proline mimetic;
Xa2 is an amino acid;
Xp1 is an amino acid wherein -Gly-Xp1- or -Sar-Xp1- form a bond cleavable by a matrixin;
Xp2 is an amino acid;
Xp3 is an amino acid;
Laa is an amino acid selected from Leu, Ile, Nle, β-homo-Leu, Hol, Hos, Ala, β-Ala, Cha, Cba, Cta, 4-pyridyl-Ala, 3-pyridyl-Ala, 2-pyridyl-Ala, Gly, Abu, Aib, Iva, Nva, Ahx, Aph, Amh, Phe, Bip, Glu, Arg, Trp, Tyr, O-($C_1$–$C_4$ alkyl)-Tyr, O-(phenyl($C_1$–$C_4$ alkyl)-)-Tyr, ($C_3$–$C_8$ alkyl)-Gly, and aminoalkyl carboxylic acid;
Cap is an N-terminus group selected from R—; Xa4-; and R-Xa4-;
Xa4- is an amino acid;
R is an amino capping group; and
A is an antineoplastic agent.

In a preferred embodiment the invention provides a compound of Formula (I) wherein A is doxorubicin, a doxorubicin derivative, or a doxorubicin analogue.

In a more preferred embodiment the invention provides a compound of Formula (I) wherein A is doxorubicin.

In a preferred embodiment the invention provides a compound of Formula (Ia):

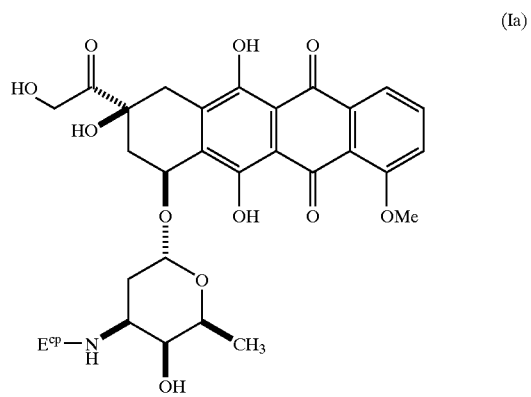

(Ia)

or a pharmaceutically acceptable salt form thereof, wherein; $E^{cp}$ is an enzyme cleavable peptide selected from:
Cap-Paa-Xa2-Gly-Xp1-Laa-;
  Cap-Xa2-Gly-Xp1-Laa-;
Cap-Paa-Xa2-Gly-Xp1-Xp2-Laa-;
  Cap-Xa2-Gly-Xp1-Xp2-Laa-;
    Cap-Gly-Xp1-Xp2-Laa-;
Cap-Paa-Xa2-Gly-Xp1-Xp2-Xp3-Laa-;
  Cap-Xa2-Gly-Xp1-Xp2-Xp3-Laa-;
    Cap-Gly-Xp1-Xp2-Xp3-Laa-;
    Cap-Paa-Xa2-Sar-Xp1-Laa-;
      Cap-Xa2-Sar-Xp1-Laa-;
Cap-Paa-Xa2-Sar-Xp1-Xp2-Laa-;
  Cap-Xa2-Sar-Xp1-Xp2-Laa-;
    Cap-Sar-Xp1-Xp2-Laa-;
Cap-Paa-Xa2-Sar-Xp1-Xp2-Xp3-Laa-;
  Cap-Xa2-Sar-Xp1-Xp2-Xp3-Laa-; and
    Cap-Sar-Xp1-Xp2-Xp3-Laa-;

Paa is a Pro, Hyp, Aze, homo-Pro, Chg, Fph, Npa, Tzc, or proline mimetic;
Xa2 is an amino acid;
Xp1 is an amino acid wherein -Gly-Xp1- or -Sar-Xp1-form a bond cleavable by a matrixin;
Xp2 is an amino acid;
Xp3 is an amino acid;
Laa is an amino acid selected from Leu, Ile, Nle, β-homo-Leu, Hol, Hos, Ala, β-Ala, Cha, Cba, Cta, 4-pyridyl-Ala, 3-pyridyl-Ala, 2-pyridyl-Ala, Gly, Abu, Aib, Iva, Nva, Ahx, Aph, Amh, Phe, Bip, Glu, Arg, Trp, Tyr, O—($C_1$–$C_4$ alkyl) Tyr, O-(phenyl($C_1$–$C_4$ alkyl)-)-Tyr, ($C_3$–$C_8$ alkyl)-Gly, and aminoalkyl carboxylic acid;
Cap is an N-terminus group selected from R—; Xa4-; and R-Xa4-;
Xa4- is an amino acid;

R is selected from: $H_3CC(=O)-$;
$HOC(=O)-(CH_2)_n C(=O)-$, wherein v is 1, 2, 3, 4, 5, or 6;
$H_3CO-(CH_2CH_2O)_t-CH2 C(=O)-$,
$HO_2CCH_2O-(CH_2CH_2O)_t-CH_2C(=O)-$,
$H_2N-(CH_2CH_2O)_t-CH_2C(=O)-$, and
$H_3CC(=O)HN-(CH_2CH_2O)_t-CH_2C(=O)-$, wherein t is 1, 2, 3, or 4;
$R^1-C(=O)-$;
$R^1-S(=O)_2-$;
$R^1-NHC(=O)-$;
$R^{1a}-CH_2C(=O)-$;
proline substituted with $-OR^3$;
$C_1-C_4$ alkyl substituted with 0–1 $R^4$;
2-carboxyphenyl-$C(=O)-$; and
$(O=)C$-phenyl-$C(=O)-$;

$R^1$ is $C_3-C_6$ cycloalkyl substituted with 0, 1, or 2 substituents selected from —OH, methoxy and —$CO_2H$;
  5–6 membered heterocycle; said heterocycle being saturated, partially saturated or unsaturated; said heterocycle containing 1, 2, 3, or 4 heteroatoms selected from N, O, and S; said heterocycle optionally substituted with 1 or 2-OH, methoxy or —$CO_2H$;
  phenyl substituted with 0, 1, or 2 substituents selected from —OH, methoxy and —$CO_2H$; or
  $C_1-C_6$ alkyl substituted with 0–4 $R^{1a}$;

$R^{1a}$ is —OH, $C_1-C_3$ alkyl, $C_1-C_4$ alkoxy, —$CO_2H$, —$N(CH_2CH_2)_2N-R^2$, —$SO_3H$;
  $C_3-C_6$ cycloalkyl substituted with 0, 1, or 2 substituents selected from methoxy and —OH;
  5–6 membered heterocycle; said heterocycle being saturated, partially saturated or unsaturated; said heterocycle containing 1, 2, 3, or 4 heteroatoms selected from N, O, and S; said heterocycle optionally substituted with 1 or 2-OH; or phenyl substituted with 0, 1, or 2 substituents selected from methoxy and —OH;

$R^2$ is —H, $H_2N(C_2-C_4$ alkyl)-, acetyl(H)N($C_2-C_4$ alkyl)-, or acetyl;

$R^3$ is —H, $C_1-C_4$ alkyl, $C_3-C_6$ cycloalkyl, phenyl, or benzyl;

$R^4$ is —OH, $C_1-C_3$ alkyl, $C_1-C_4$ alkoxy, —$CO_2H$, —$N(CH_2CH_2)_2N-R^2$;
  $C_3-C_6$ cycloalkyl substituted with 0, 1, or 2 substituents selected from methoxy and —OH;
  5–6 membered heterocycle; said heterocycle being saturated, partially saturated or unsaturated; said heterocycle containing 1, 2, 3, or 4 heteroatoms selected from N, O, and S; said heterocycle optionally substituted with 1 or 2-OH; or
  $C_6-C_{10}$ carbocycle substituted with 0, 1, or 2 substituents selected from methoxy and —OH.

In a preferred embodiment the invention provides a compound of Formula (1a), or a pharmaceutically acceptable salt form thereof, wherein;

$E^{cp}$ is an enzyme cleavable peptide selected from:
  Cap-Paa-Xa2-Gly-Xp1-Laa-;
    Cap-Xa2-Gly-Xp1-Laa-;
  Cap-Paa-Xa2-Gly-Xp1-Xp2-Laa-;
    Cap-Xa2-Gly-Xp1-Xp2-Laa-;
      Cap-Gly-Xp1-Xp2-Laa-;
  Cap-Paa-Xa2-Gly-Xp1-Xp2-Xp3-Laa-;
    Cap-Xa2-Gly-Xp1-Xp2-Xp3-Laa-;
      Cap-Gly-Xp1-Xp2-Xp3-Laa-;

Paa is a Pro, Hyp, Aze, homo-Pro, Chg, Fph, Npa, Tzc, or proline mimetic;

Xa2 is an amino acid;

Xp1 is an amino acid wherein-Gly-Xp1- forms a bond cleavable by a matrixin;

Xp2 is an amino acid;

Xp3 is an amino acid;

Laa is an amino acid selected from Leu, Ile, Nle, β-homo-Leu, Hol, Hos, Ala, β-Ala, Cha, Cba, Cta, 4-pyridyl-Ala, Abu, Aib, Iva, Nva, Phe, Bip, Tyr, O-benzyl-Tyr; and Cap is an N-terminus group selected from R—; Xa4-; and R-Xa4-;

Xa4- is an amino acid;

R is selected from: $H_3CC(=O)-$;
$HOC(=O)-(CH_2)_vC(=O)-$, wherein v is 1, 2, 3, or 4;
$H_3CO-(CH_2CH_2O)_t-CH_2C(=O)-$,
$HO_2CCH_2O-(CH_2CH_2O)_t-CH_2C(=O)-$,
$H_2N-(CH_2CH_2O)_t-CH_2C(=O)-$, and
$H_3CC(=O)HN-(CH_2CH_2O)_t-CH_2C(=O)-$, wherein t is 1, 2, or 3;
$R^1-C(=O)-$;
$R^1-S(=O)_2-$;
$R^1-NHC(=O)-$;
$R^{1a}-CH_2C(=O)-$;
proline substituted with $-OR^3$;
$C_1-C_4$ alkyl substituted with 0–1 $R^4$;
$HO_3SCH_2CH(NH_2)C(=O)-$;
2-carboxyphenyl-$C(=O)-$; and
$(O=)C$-phenyl-$C(=O)-$;

$R^1$ is $C_3-C_6$ cycloalkyl substituted with 0, 1, or 2 substituents selected from —OH, methoxy and —$CO_2H$;
  5–6 membered heterocycle; said heterocycle being saturated, partially saturated or unsaturated; said heterocycle containing 1, 2, 3, or 4 heteroatoms selected from N, O, and S; said heterocycle optionally substituted with 1 or 2-OH, methoxy or —$CO_2H$;
  phenyl substituted with 0, 1, or 2 substituents selected from —OH, methoxy and —$CO_2H$; or
  $C_1-C_6$ alkyl substituted with 0–4 $R^{1a}$;

$R^{1a}$ is —OH, $C_1-C_3$ alkyl, $C_1-C_4$ alkoxy, —$CO_2H$, —$N(CH_2CH_2)_2N-R^2$, —$SO_3H$;
  $C_3-C_6$ cycloalkyl substituted with 0, 1, or 2 substituents selected from methoxy and —OH;
  5–6 membered heterocycle; said heterocycle being saturated, partially saturated or unsaturated; said heterocycle containing 1, 2, 3, or 4 heteroatoms selected from N, O, and S; said heterocycle optionally substituted with 1 or 2-OH; or
  phenyl substituted with 0, 1, or 2 substituents selected from methoxy and —OH;

$R^2$ is —H, $H_2N(C_2-C_4$ alkyl)-, acetyl(H)N($C_2-C_4$ alkyl)-, or acetyl;

$R^3$ is —H, $C_1-C_4$ alkyl, $C_3-C_6$ cycloalkyl, phenyl, or benzyl;

$R^4$ is —OH, $C_1-C_3$ alkyl, $C_1-C_4$ alkoxy, —$CO_2H$, —$N(CH_2CH_2)_2N-R^2$;
  $C_3-C_6$ cycloalkyl substituted with 0, 1, or 2 substituents selected from methoxy and —OH;
  5–6 membered heterocycle; said heterocycle being saturated, partially saturated or unsaturated; said heterocycle containing. 1, 2, 3, or 4 heteroatoms selected from N, O, and S; said heterocycle optionally substituted with 1 or 2-OH; or $C_6$–$C_{10}$ carbocycle substituted with 0, 1, or 2 substituents selected from methoxy and —OH.

In a preferred embodiment the invention provides a compound of Formula (1a), wherein-Gly-Xp1- forms a bond cleavable by the matrixin selected from MMP-2, MMP-9, and MMP-14.

In a preferred embodiment the invention provides a compound of Formula (1a), wherein-Gly-Xp1- forms a bond cleavable by the matrixin selected from MMP-2 and MMP-9.

In a preferred embodiment the invention provides a compound of Formula (1a), wherein-Gly-Xp1- forms a bond cleavable by the matrixin MMP-14.

In a preferred embodiment the invention provides a compound of Formula (1a), wherein-Gly-Xp1- forms a bond cleavable by MMP-2, MMP-9, and MMP-14.

In a preferred embodiment the invention provides a compound of Formula (1a), or a pharmaceutically acceptable salt form thereof, wherein;

$E^{cp}$ is an enzyme cleavable peptide selected from:
Cap-Paa-Xa2-Gly-Xp1-Laa-;
Cap-Xa2-Gly-Xp1-Laa-;
Cap-Paa-Xa2-Gly-Xp1-Xp2-Laa-;
Cap-Xa2-Gly-Xp1-Xp2-Laa-;
Cap-Gly-Xp1-Xp2-Laa-;
Cap-Paa-Xa2-Gly-Xp1-Xp2-Xp3-Laa-;
Cap-Xa2-Gly-Xp1-Xp2-Xp3-Laa-;
Cap-Gly-Xp1-Xp2-Xp3-Laa-;
wherein-Gly-Xp1-forms a bond cleavable by a matrixin;
Paa is a Pro, Hyp, Aze, homo-Pro, Chg, Fph, Npa, Tzc, or proline mimetic of formula:

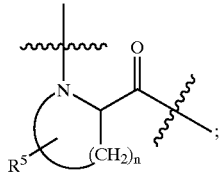

wherein $R^5$ is selected from H, halogen, $C_1$–$C_6$ alkyl, —OH, $C_1$–$C_6$ alkoxy, and benzyloxy; and n is 2, 3, 4, or 5;
Xa2 is an amino acid selected from
Hof, Leu, His, Arg, Gln, Ile, Val, Lys, (R)-Leu, Orn, β-Ala, γ-Abu, Cha, Chg, Dap, Cit, N-methyl-Leu, valerolactam, N,N-dimethyl-Lys, 4-aza-Phe, morpholinylpropyl-Gly, N-methylpiperazinepropyl-Gly, 4-aza-Hof, Ala, Asn, Asp, Aze, Cys, Glu, Gly, Hyp, Irg, Met, Phe, Phe(4-fluoro), Pro, Sar, Ser, Thr, Trp, Tyr, Cya, Hca, and Spa;
Xp1 is an amino acid selected from Hof; Leu; Bip; Phe; nor-Leu; Tha; Phg; Val; Glu; Asn; Ser; Ala; homo-Tyr; Aze; 4-aza-Hof; O-(3-pyridyl)-Tyr; O-(4-pyridyl)-Tyr; O-benzyl-Tyr; O-benzyl-Thr; O-benzyl-Ser; O-methyl-Ser; O-allyl-Ser; 4-nitro-Hof; N-methyl-Leu; O-(4-pyridylmethyl)-Tyr; 4-hydroxy-phenyl-Gly, phenylpropyl-Gly; styryl-Ala, and 2Nal;
Xp2 is an amino acid selected from Tyr; Ala; Ser; Leu; Gin; Val; Glu, His; Lys; Arg; Orn; Aze; Hof; homo-Tyr; Cit; 4-aza-Phe; N,N-Dimethyl-Lys; Dab; Dap; Asn, Asp, Aze, Cha, Cys, Gly, Hyp, Ile, Irg, Met, Phe, Phe(4-fluoro), Pro, Sar, Thr, Trp, Cya, Hca, Spa, morpholinylpropyl-Gly; O-(4-pyridylmethyl)-Tyr; and N-methylpiperazinepropyl-Gly;
Xp3 is an amino acid selected from Tyr, Ala, Ser, Leu, Hof, Arg, Asn, Asp, Aze, Cha, Cys, Dpa, Gin, Glu, Gly, His, Hyp, Ile, Irg, Lys, Met, Orn, Phe, Phe(4-fluoro), Pro, Sar, Thr, Trp, and Val;
Laa is an amino acid selected from Leu, Ile, Nle, β-homo-Leu, Hol, Hos, Ala, β-Ala, Cha, Cba, Cta, 4-pyridyl-Ala, Abu, Aib, Iva, Nva, and Phe;
Cap is an N-terminus group selected from R—; Xa4-; and R-Xa4-;
Xa4-is an amino acid selected from Gly, Pro, γ-Glu, Dmg, Ala, Arg, Asn, Asp, β-Asp, Aze, Cha, Cys, Dpa, Gin, Glu, His, Hyp, Ile, Irg, Leu, Lys, Met, Orn, Phe, Sar, Ser, Thr, Trp, Tyr, and Val;
R is selected from: $H_3CC(=O)$—;
$HOC(=O)CH_2CH_2C(=O)$—;
$HOC(=O)CH_2CH_2CH_2C(=O)$—;
$HOC(=O)CH_2CH_2CH_2CH_2C(=O)$—;
$H_3COCH_2CH_2OCH_2C(=O)$—,
$H_3COCH_2CH_2OCH_2CH_2OCH_2C(=O)$—,
$H_2CCH_2OCH_2CH_2OCH_2C(=O)$—,
$H_2NCH_2CH_2OCH_2C(=O)$—,
$H_2NCH_2CH_2OCH_2CH_2OCH_2C(=O)$—,
$H_3CC(=O)HNCH_2CH_2OCH_2C(=O)$—,
$H_3CC(=O)HNCH_2CH_2OCH_2CH_2OCH_2C(=O)$—,
$H_2NCH_2CH_2N(CH_2CH_2)_2NCH_2C(O)$—;
$H_3CC(=O)HNCH_2CH_2N(CH_2CH_2)_2NCH_2C(O)$—;
$H_3CC(=O)N(CH_2CH_2)_2NCH_2C(O)$—;
$O(CH_2CH_2)_2NCH_2CH_2NHC(O)$—
$HO_2CCH_2C(CO_2H)(OH)CH_2C(=O)$—,
$HO_2CCH_2C(CH_3)(OH)CH_2C(=O)$—,
2-carboxycyclohexyl-$C(=O)$—;
2-carboxycyclopentyl-$C(=O)$—;
carbobenzyloxy;
4-methoxy-benzenesulfonyl;
cyclopropylcarbonyl;
cyclobutylcarbonyl;
3-pyridinecarbonyl;
2-pyrazinecarbonyl;
tetrazoleacetyl;
pivaloyl;
methoxyacetyl;
hydroxyproline; and
4-(2-(5,6,7,8-tetrahydronaphthenyl))butyl.

In a preferred embodiment the invention provides a compound of Formula (Ia), wherein-Gly-Xp1-forms a bond cleavable by the matrixin selected from MMP-2, MMP-9, and MMP-14.

In a preferred embodiment the invention provides a compound of Formula (Ia), wherein-Gly-Xp1-forms a bond cleavable by the matrixin selected from MMP-2 and MMP-9.

In a preferred embodiment the invention provides a compound of Formula (Ia), wherein-Gly-Xp1-forms a bond cleavable by the matrixin MMP-14.

In a preferred embodiment the invention provides a compound of Formula (Ia), wherein-Gly-Xp1-forms a bond cleavable by MMP-2, MMP-9, and MMP-14.

In a preferred embodiment the invention provides a compound of Formula (Ia), or a pharmaceutically acceptable salt form thereof, wherein;
$E^{CP}$ is an enzyme cleavable peptide selected from:
Cap-Paa-Xa2-Gly-Leu-Laa-;
Cap-Paa-Xa2-Gly-Hof-Laa-;
Cap-Xa2-Gly-Leu-Laa-;
Cap-Xa2-Gly-Hof-Laa-;
Cap-Paa-Xa2-Gly-Leu-Xp2-Laa-;
Cap-Paa-Xa2-Gly-Hof-Xp2-Laa-;
Cap-Xa2-Gly-Leu-Xp2-Laa-;

Cap-Xa2-Gly-Hof-Xp2-Laa-;
Cap-Gly-Leu-Xp2-Laa-; and
Cap-Gly-Hof-Xp2-Laa-;
wherein-Gly-Leu- and -Gly-Hof-form a bond cleavable by a matrixin;

Paa is a Pro, Hyp, Aze, homo-Pro, or Npa;

Xa2 is an amino acid selected from
Hof, Leu, His, Arg, Gln, Ile, Val, Lys, (R)-Leu, Orn, β-Ala, γ-Abu, Cha, Chg, Dap, Cit, N-methyl-Leu, valerolactam, N,N-dimethyl-Lys, 4-aza-Phe, morpholinylpropyl-Gly, N-methylpiperazinepropyl-Gly, 4-aza-Hof, Ala, Asn, Asp, Aze, Cys, Glu, Gly, Hyp, Irg, Met, Phe, Phe(4-fluoro), Pro, Sar, Ser, Thr, Trp, Tyr, Cya, Hca, and Spa;

Xp2 is an amino acid selected from Tyr; Ala; Ser; Leu; Gln; Val; Glu, His; Lys; Arg; Orn; Aze; Hof; homo-Tyr; Cit; 4-aza-Phe; N,N-Dimethyl-Lys; Dab; Dap; Asn, Asp, Aze, Cha, Cys, Gly, Hyp, Ile, Irg, Met, Phe, Phe(4-fluoro), Pro, Sar, Thr, Trp, Cya, Hca, Spa, morpholinylpropyl-Gly; O-(4-pyridylmethyl)-Tyr; and N-methylpiperazinepropyl-Gly;

Laa is an amino acid selected from Leu, Cha, Nle, and Hol;

Cap is an N-terminus group selected from R—; Xa4-; and R-Xa4-;

Xa4-is an amino acid selected from Gly, Pro, γ-Glu, and Dmg;

R is selected from: $H_3CC(=O)$—;
$HOC(=O)CH_2CH_2C(=O)$—;
$HOC(=O(O))CH_2CH_2CH_2C(=O)$—;
$HOC(=O)CH_2CH_2CH_2CH_2C(=O)$—;
$H_3COCH_2CH_2OCH_2C(=O)$—,
$H_3COCH_2CH_2OCH_2CH_2OCH_2C(=O)$—,
$HO_2CCH_2OCH_2CH_2OCH_2C(=O)$—,
$H_2NCH_2CH_2OCH_2C(=O)$—,
$H_2NCH_2CH_2OCH_2CH_2OCH_2C(=O)$—,
$H_3CC(=O)HNCH_2CH_2OCH_2C(=O)$—,
$H_3CC(=O)HNCH_2CH_2OCH_2CH_2OCH_2C(=O)$—,
$H_2NCH_2CH_2N(CH_2CH_2)_2NCH_2C(O)$—;
$H_3CC(=O)HNCH_2CH_2N(CH_2CH_2)_2NCH_2C(O)$—;
$H_3CC(=O)N(CH_2CH_2)_2NCH_2C(O)$—;
$O(CH_2CH_2)_2NCH_2CH_2NHC(O)$—
$HO_2CCH_2C(CO_2H)(OH)CH_2C(=O)$—,
$HO_2CCH_2C(CH_3)(OH)CH_2C(=O)$—,
2-carboxycyclohexyl-C(=O)—;
2-carboxycyclopentyl-C(=O)—;
carbobenzyloxy;
4-methoxy-benzenesulfonyl;
cyclopropylcarbonyl;
cyclobutylcarbonyl;
3-pyridinecarbonyl;
2-pyrazinecarbonyl;
tetrazoleacetyl;
pivaloyl;
methoxyacetyl;
hydroxyproline; and
4(2-(5,6,7,8-tetrahydronaphthenyl))butyl.

In a preferred embodiment the invention provides a compound of Formula (Ia), wherein -Gly-Leu- and -Gly-Hof- form a bond cleavable by the matrixin selected from MMP-2, MMP-9, and MMP-14.

In a preferred embodiment the invention provides a compound of Formula (Ia), wherein -Gly-Leu- and -Gly-Hof- form a bond cleavable by the matrixin selected from MMP-2 and MMP-9.

In a preferred embodiment the invention provides a compound of Formula (Ia), wherein -Gly-Leu- and -Gly-Hof- form a bond cleavable by the matrixin MMP-14.

In a preferred embodiment the invention provides a compound of Formula (Ia), wherein -Gly-Leu- and -Gly-Hof- form a bond cleavable by MMP-2, MMP-9, and MMP-14.

In a preferred embodiment the invention provides a compound of Formula (Ia), or a pharmaceutically acceptable salt form thereof, wherein;

$E^{cp}$ is an enzyme cleavable peptide selected from:
Cap-Paa-Xa2-Gly-Leu-Leu-;
Cap-Paa-Xa2-Gly-Leu-Cha-;
Cap-Paa-Xa2-Gly-Leu-Nle-;
Cap-Paa-Xa2-Gly-Leu-Hol-;
Cap-Paa-Xa2-Gly-Hof-Leu-;
Cap-Paa-Xa2-Gly-Hof-Cha-;
Cap-Paa-Xa2-Gly-Hof-Nle-;
Cap-Paa-Xa2-Gly-Hof-Hol-;
Cap-Paa-Xa2-Gly-Leu-Xp2-Leu-;
Cap-Paa-Xa2-Gly-Leu-Xp2-Cha-;
Cap-Paa-Xa2-Gly-Leu-Xp2-Nle-;
Cap-Paa-Xa2-Gly-Leu-Xp2-Hol-;
Cap-Paa-Xa2-Gly-Hof-Xp2-Leu-;
Cap-Paa-Xa2-Gly-Hof-Xp2-Cha-;
Cap-Paa-Xa2-Gly-Hof-Xp2-Nle-;
Cap-Paa-Xa2-Gly-Hof-Xp2-Hol-;

wherein -Gly-Leu- and -Gly-Hof-form a bond cleavable by a matrixin;

Paa is a Pro, Hyp, Aze, homo-Pro, or Npa;

Xa2 is an amino acid selected from
Hof, Leu, His, Arg, Gln, Ile, Val, Lys, (R)-Leu, Orn, β-Ala, γ-Abu, Cha, Chg, Dap, Cit, N-methyl-Leu, valerolactam, N,N-dimethyl-Lys, 4-aza-Phe, morpholinylpropyl-Gly, N-methylpiperazinepropyl-Gly, 4-aza-Hof, Ala, Asn, Asp, Aze, Cys, Glu, Gly, Hyp, Irg, Met, Phe, Phe(4-fluoro), Pro, Sar, Ser, Thr, Trp, and Tyr;

Xp2 is an amino acid selected from Tyr; Ala; Ser; Leu; Gln; Val; Glu, His; Lys; Arg; Orn; Aze; Hof; homo-Tyr; Cit; 4-aza-Phe; N,N-dimethyl-Lys; Dab; Dap; Asn, Asp, Aze, Cha, Cys, Gly, Hyp, Ile, Irg, Met, Phe, Phe(4-fluoro), Pro, Sar, Thr, Trp; morpholinylpropyl-Gly; O-(4-pyridylmethyl)-Tyr; and N-methylpiperazinepropyl-Gly;

Cap is an N-terminus group selected from R—; Xa4-; and R-Xa4-;

Xa4-is an amino acid selected from Gly, Pro, γ-Glu, and Dmg;

R is selected from: $H_3CC(=O)$—;
$HOC(=O)CH_2CH_2C(=O)$—;
$HOC(=O)CH_2CH_2CH_2C(=O)$—;
$HOC(=O)CH_2CH_2CH_2CH_2C(=O)$—;
$H_3COCH_2CH_2OCH_2C(=O)$—;
$H_3COCH_2CH_2OCH_2CH_2OCH_2C(=O)$—;
2-carboxycyclohexyl-C(=O)—;
2-carboxycyclopentyl-C(=O)—; and
tetrazoleacetyl.

In a preferred embodiment the invention provides a compound of Formula (Ia), wherein -Gly-Leu- and -Gly-Hof- form a bond cleavable by the matrixin selected from MMP-2, MMP-9, and MMP-14.

In a preferred embodiment the invention provides a compound of Formula (Ia), wherein -Gly-Leu- and -Gly-Hof- form a bond cleavable by the matrixin selected from MMP-2 and MMP-9.

In a preferred embodiment the invention provides a compound of Formula (Ia), wherein -Gly-Leu- and -Gly-Hof- form a bond cleavable by the matrixin MMP-14.

In a preferred embodiment the invention provides a compound of Formula (Ia), wherein -Gly-Leu- and -Gly-Hof- form a bond cleavable by MMP-2, MMP-9, and MMP-14.

In a preferred embodiment the invention provides a compound of Formula (Ia), or a pharmaceutically acceptable salt form thereof, wherein;
$E^{CP}$ is an enzyme cleavable peptide selected from:
- Cap-Xa2-Gly-Leu-Leu-;
- Cap-Xa2-Gly-Leu-Cha-;
- Cap-Xa2-Gly-Leu-Nle-;
- Cap-Xa2-Gly-Leu-Hol-;
- Cap-Xa2-Gly-Hof-Leu-;
- Cap-Xa2-Gly-Hof-Cha-;
- Cap-Xa2-Gly-Hof-Nle-;
- Cap-Xa2-Gly-Hof-Hol-;
- Cap-Xa2-Gly-Leu-Xp2-Leu-;
- Cap-Xa2-Gly-Leu-Xp2-Cha-;
- Cap-Xa2-Gly-Leu-Xp2-Nle-;
- Cap-Xa2-Gly-Leu-Xp2-Hol-;
- Cap-Xa2-Gly-Hof-Xp2-Leu-;
- Cap-Xa2-Gly-Hof-Xp2-Cha-;
- Cap Xa2-Gly-Hof-Xp2-Nle-; and
- Cap-Xa2-Gly-Hof-Xp2-Hol-;

wherein -Gly-Leu- and -Gly-Hof- form a bond cleavable by a matrixin;

Xa2 is an amino acid selected from
Hof, Leu, His, Arg, Gln, Ile, Val, Lys, (R)-Leu, Orn, β-Ala, γ-Abu, Cha, Chg, Dap, Cit, N-methyl-Leu, valerolactam, N,N-dimethyl-Lys, 4-aza-Phe, morpholinylpropyl-Gly, N-methylpiperazinepropyl-Gly, 4-aza-Hof, Ala, Asn, Asp, Aze, Cys, Glu, Gly, Hyp, Irg, Met, Phe, Phe(4-fluoro), Pro, Sar, Ser, Thr, Trp, and Tyr;

Xp2 is an amino acid selected from Tyr; Ala; Ser; Leu; Gln; Val; Glu, His; Lys; Arg; Orn; Aze; Hof; homo-Tyr; Cit; 4-aza-Phe; N,N-dimethyl-Lys; Dab; Dap; Asn, Asp, Aze, Cha, Cys, Gly, Hyp, Ile, Irg, Met, Phe, Phe(4-fluoro), Pro, Sar, Thr, Trp; morpholinylpropyl-Gly; O-(4-pyridylmethyl)-Tyr; and N-methylpiperazinepropyl-Gly;

Cap is an N-terminus group selected from R—; Xa4-; and R-Xa4-;

Xa4-is an amino acid selected from Gly, Pro, γ-Glu, and Dmg;

R is selected from: $H_3CC(=O)$—;
$HOC(=O)CH_2CH_2C(=O)$—;
$HOC(=O)CH_2CH_2CH_2C(=O)$—;
$HOC(=O)CH_2CH_2CH_2CH_2C(=O)$—;
$H_3COCH_2CH_2OCH_2C(=O)$—;
$H_3COCH_2CH_2OCH_2CH_2OCH_2C(=O)$—;
2-carboxycyclohexyl-$C(=O)$—;
2-carboxycyclopentyl-$C(=O)$—; and
tetrazoleacetyl.

In a preferred embodiment the invention provides a compound of Formula (Ia), wherein -Gly-Leu- and -Gly-Hof- form a bond cleavable by the matrixin selected from MMP-2, MMP-9, and MMP-14.

In a preferred embodiment the invention provides a compound of Formula (Ia), wherein -Gly-Leu- and -Gly-Hof- form a bond cleavable by the matrixin selected from MMP-2 and MMP-9.

In a preferred embodiment the invention provides a compound of Formula (Ia), wherein -Gly-Leu- and -Gly-Hof-form a bond cleavable by the matrixin MMP-14.

In a preferred embodiment the invention provides a compound of Formula (Ia), wherein -Gly-Leu- and -Gly-Hof- form a bond cleavable by MMP-2, MMP-9, and MMP-14.

In another preferred embodiment the invention provides a compound of Formula (Ia), or a pharmaceutically acceptable salt form thereof, wherein;
$E^{CP}$ is an enzyme cleavable peptide selected from:

| | |
|---|---|
| SEQ ID NO: 185 | R-γ-E-P-Orn-G-Hof-E-L-; |
| SEQ ID NO: 186: | R-γ-E-P-L-G-(O-benzyl-S)-Y-L-; |
| SEQ ID NO: 187: | R-γ-E-P-L-G-(O-benzyl-S)-Y-Nle-; |
| SEQ ID NO: 188 | R-P-L-G-(O-benzyl-S)-Y-L-; |
| SEQ ID NO: 189 | R-P-L-G-(O-methyl-S)-Y-L-; |
| SEQ ID NO: 190 | R-P-L-G-(azaHof)-Y-L-; |
| SEQ ID NO: 191 | R-P-L-G-Hof-Y-L-; |
| SEQ ID NO: 192 | R-P-L-G-Hof-E-L-; |
| SEQ ID NO: 193 | R-P-L-G-(O-benzyl-S)-Y-Nle-; |
| SEQ ID NO: 194 | R-P-L-G-(O-methyl-S)-Y-Nle-; |
| SEQ ID NO: 195 | R-P-L-G-(azaHof)-Y-Nle-; |
| SEQ ID NO: 196 | R-P-L-G-Hof-Y-Nle-; |
| SEQ ID NO: 197 | R-P-L-G-Hof-E-Nle-; |
| SEQ ID NO: 198 | R-P-L-G-(O-benzyl-S)-Y-Hol-; |
| SEQ ID NO: 199 | R-P-L-G-(O-methyl-S)-Y-Hol-; |
| SEQ ID NO: 200 | R-P-L-G-(azaHof)-Y-Hol-; |
| SEQ ID NO: 201 and | R-P-L-G-Hof-Y-Hol-; |
| SEQ ID NO: 202 | R-P-L-G-Hof-E-Hol-; |

R is selected from: $H_3CC(=O)$—;
$HOC(=O)$—$(CH_2)_v C(=O)$—, wherein v is 1, 2, 3, 4, 5, or 6;
$H_3CO$—$(CH_2CH_2O)_t$—$CH_2C(=O)$—,
$HO_2CCH_2O$—$(CH_2CH_2O)_t$—$CH_2C(=O)$—,
$H_2N$—$(CH_2CH_2O)_t$—$CH_2C(=O)$—, and
$H_3CC(=O)HN$—$(CH_2CH_2O)_t$—$CH_2C(=O)$—, wherein t is 1, 2, 3, or 4;
$R^1$-$C(=O)$—;
$R^1$-$S(=O)_2$—;
$R^1$—$NHC(=O)$—;
$R^{1a}$-$CH_2C(=O)$—;
proline substituted with —$OR^3$.
$C_1$–$C_4$ alkyl substituted with 0–1 $R^4$;
2-carboxyphenyl-$C(=O)$—; and
$(O=)C$-phenyl-$C(=O)$—;

$R^1$ is $C_3$–$C_6$ cycloalkyl substituted with 0, 1, or 2 substituents selected from —OH, methoxy and —$CO_2H$;
5–6 membered heterocycle; said heterocycle being saturated, partially saturated or unsaturated; said heterocycle containing 1, 2, 3, or 4 heteroatoms selected from N, O, and S; said heterocycle optionally substituted with 1 or 2-OH, methoxy or —$CO_2H$;
phenyl substituted with 0, 1, or 2 substituents selected from —OH, methoxy and —$CO_2H$; or
$C_1$–$C_6$ alkyl substituted with 0–4 $R^{1a}$;

$R^{1a}$ is —OH, $C_1$–$C_3$ alkyl, $C_1$–$C_4$ alkoxy, —$CO_2H$, —$N(CH_2CH_2)_2N$—$R^2$, —$SO_3H$;
$C_3$–$C_6$ cycloalkyl substituted with 0, 1, or 2 substituents selected from methoxy and —OH;
5–6 membered heterocycle; said heterocycle being saturated, partially saturated or unsaturated; said heterocycle containing 1, 2, 3, or 4 heteroatoms selected from N, O, and S; said heterocycle optionally substituted with 1 or 2-OH; or
phenyl substituted with 0, 1, or 2 substituents selected from methoxy and —OH;

$R^2$ is —H, $H_2N(C_2$–$C_4$ alkyl)-, acetyl(H)N($C_2$–$C_4$ alkyl)-, or acetyl;

$R^3$ is —H, $C_1$–$C_4$ alkyl, $C_3$–$C_6$ cycloalkyl, phenyl, or benzyl;

$R^4$ is —OH, $C_1$–$C_3$ alkyl, $C_1$–$C_4$ alkoxy, —$CO_2H$, —$N(CH_2CH_2)_2N$—$R^2$;

$C_3$–$C_6$ cycloalkyl substituted with 0, 1, or 2 substituents selected from methoxy and —OH;

5–6 membered heterocycle; said heterocycle being saturated, partially saturated or unsaturated; said heterocycle containing 1, 2, 3, or 4 heteroatoms selected from N, O, and S; said heterocycle optionally substituted with 1 or 2-OH; or $C_6$–$C_{10}$ carbocycle substituted with 0, 1, or 2 substituents selected from methoxy and —OH.

In a preferred embodiment the invention provides a compound of Formula (Ia), or a pharmaceutically acceptable salt form thereof, wherein;

$E^{CP}$ is an enzyme cleavable peptide selected from:

| | |
|---|---|
| SEQ ID NO: 185 | R-γ-E-P-Orn-G-Hof-E-L; |
| SEQ ID NO: 186: | R-γ-E-P-L-G-(O-benzyl-S)-Y-L-; |
| SEQ ID NO: 187: | R-γ-E-P-L-G-(O-benzyl-S)-Y-Nle-; |
| SEQ ID NO: 188 | R-P-L-G-(O-benzyl-S)-Y-L-; |
| SEQ ID NO: 189 | R-P-L-G-(O-methyl-S)-Y-L-; |
| SEQ ID NO: 190 | R-P-L-G-(azaHof)-Y-L-; |
| SEQ ID NO: 191 | R-P-L-G-Hof-Y-L-; |
| SEQ ID NO: 192 | R-P-L-G-Hof-E-L-; |
| SEQ ID NO: 193 | R-P-L-G-(O-benzyl-S)-Y-Nle-; |
| SEQ ID NO: 194 | R-P-L-G-(O-methyl-S)-Y-Nle-; |
| SEQ ID NO: 195 | R-P-L-G-(azaHof)-Y-Nle-; |
| SEQ ID NO: 196 | R-P-L-G-Hof-Y-Nle-; |
| SEQ ID NO: 197 | R-P-L-G-Hof-E-Nle-; |
| SEQ ID NO: 198 | R-P-L-G-(O-benzyl-S)-Y-Hol-; |
| SEQ ID NO: 199 | R-P-L-G-(O-methyl-S)-Y-Hol-; |
| SEQ ID NO: 200 | R-P-L-G-(azaHof)-Y-Hol-; |
| SEQ ID NO: 201 and | R-P-L-G-Hof-Y-Hol-; |
| SEQ ID NO: 202 | R-P-L-G-Hof-E-Hol-; |

R is selected from: $H_3CC(=O)$—;
$HOC(=O)CH_2CH_2C(=O)$—;
$HOC(=O)CH_2CH_2CH_2C(=O)$—;
$HOC(=O)CH_2CH_2CH_2CH_2C(=O)$—;
$H_3COCH_2CH_2OCH_2C(=O)$—,
$H_3COCH_2CH_2OCH_2CH_2OCH_2C(=O)$—,
$HO_2CCH_2OCH_2CH_2OCH_2C(=O)$—,
$H_2NCH_2CH_2OCH_2C(=O)$—,
$H_2NCH_2CH_2OCH_2CH_2OCH_2C(=O)$—,
$H_3CC(=O)HNCH_2CH_2OCH_2C(=O)$—,
$H_3CC(=O)HNCH_2CH_2OCH_2CH_2OCH_2C(=O)$—,
$H_2NCH_2CH_2N(CH_2CH_2)_2NCH_2C(O)$—;
$H_3CC(=O)HNCH_2CH_2N(CH_2CH_2)_2NCH_2C(O)$—;
$H_3CC(=O)N(CH_2CH2)_2NCH_2C(O)$—;
$O(CH_2CH_2)_2NCH_2CH_2NHC(O)$—$HO_2CCH_2C(CO_2H)(OH)CH_2C(=O)$—,
$HO_2CCH_2C(CH_3)(OH)CH_2C(=O)$—,
2-carboxycyclohexyl-$C(=O)$—;
2-carboxycyclopentyl-$C(=O)$—;
carbobenzyloxy;
4-methoxy-benzenesulfonyl;
cyclopropylcarbonyl;
cyclobutylcarbonyl;
3-pyridinecarbonyl;
2-pyrazinecarbonyl;
tetrazoleacetyl;
pivaloyl;
methoxyacetyl;
hydroxyproline; and
4-(2-(5,6,7,8-tetrahydronaphthenyl))butyl.

In a preferred embodiment the invention provides a compound of Formula (Ia), or a pharmaceutically acceptable salt form thereof, wherein;

$E^{CP}$ is an enzyme cleavable peptide selected from:

| | |
|---|---|
| SEQ ID NO: 185 | R-γ-E-P-Orn-G-Hof-E-L-; |
| SEQ ID NO: 186: | R-γ-E-P-L-G-(O-benzyl-S)-Y-L-; |
| SEQ ID NO: 187: | R-γ-E-P-L-G-(O-benzyl-S)-Y-Nle-; |
| SEQ ID NO: 188 | R-P-L-G-(O-benzyl-S)-Y-L-; |
| SEQ ID NO: 189 | R-P-L-G-(O-methyl-S)-Y-L-; |
| SEQ ID NO: 190 | R-P-L-G-(azaHof)-Y-L-; |
| SEQ ID NO: 191 | R-P-L-G-Hof-Y-L-; |
| SEQ ID NO: 192 | R-P-L-G-Hof-E-L-; |
| SEQ ID NO: 193 | R-P-L-G-(O-benzyl-S)-Y-Nle-; |
| SEQ ID NO: 194 | R-P-L-G-(O-methyl-S)-Y-Nle-; |
| SEQ ID NO: 195 | R-P-L-G-(azaHof)-Y-Nle-; |
| SEQ ID NO: 196 | R-P-L-G-Hof-Y-Nle-; |
| SEQ ID NO: 197 | R-P-L-G-Hof-E-Nle-; |
| SEQ ID NO: 198 | R-P-L-G-(O-benzyl-S)-Y-Hol-; |
| SEQ ID NO: 199 | R-P-L-G-(O-methyl-S)-Y-Hol-; |
| SEQ ID NO: 200 | R-P-L-G-(azaHof)-Y-Hol-; |
| SEQ ID NO: 201 and | R-P-L-G-Hof-Y-Hol-; |
| SEQ ID NO: 202 | R-P-L-G-Hof-E-Hol-; |

R is selected from: $H_3CC(=O)$—;
$HOC(=O)CH_2CH_2C(=O)$—;
$HOC(=O)CH_2CH_2CH_2C(=O)$—;
$HOC(=O)CH_2CH_2CH_2CH_2C(=O)$—;
$H_3COCH_2CH_2OCH_2C(=O(O))$—;
$H_3COCH_2CH_2OCH_2CH_2OCH_2C(=O)$—; and
tetrazoleacetyl.

In another preferred embodiment, the invention provides a compound selected from:

| | |
|---|---|
| SEQ ID NO: 1: | 4-methoxy-benzenesulfonyl-β-Ala-G-Hof-Y-L-Dox; |
| SEQ ID NO: 2: | 1,2-$C_6H_4$ $(CO)_2$-H-G-Hof-Y-L-Dox; |
| SEQ ID NO: 3: | acetyl-P-L-G-L-L-Dox; |
| SEQ ID NO: 4: | acetyl-P-(R)L-G-L-L-Dox; |
| SEQ ID NO: 5: | acetyl-P-(β-Ala)-G-L-L-Dox; |
| SEQ ID NO: 6: | acetyl-P-(γ-Abu)-G-L-L-Dox; |
| SEQ ID NO: 7: | acetyl-P-Cha-G-L-L-Dox; |
| SEQ ID NO: 8: | P-L-G-L-L-Dox; |
| SEQ ID NO: 9: | MeOCH$_2$CH$_2$OCH$_2$C(=O)-P-L-G-L-L-Dox; |
| SEQ ID NO: 10: | MeOCH$_2$CH$_2$OCH$_2$CH$_2$OCH$_2$C(=O)-P-L-G-L-L-Dox; |
| SEQ ID NO: 11: | H$_2$NCH$_2$CH$_2$N(CH$_2$CH$_2$)$_2$NCH$_2$C(=O)-P-L-G-L-L-Dox; |
| SEQ ID NO: 12: | AcHNCH$_2$CH$_2$N(CH$_2$CH$_2$)$_2$NCH$_2$C(=O)-P-L-G-L-L-Dox; |
| SEQ ID NO: 13: | AcN(CH$_2$CH$_2$)$_2$NCH$_2$C(=O)-P-L-G-L-L-Dox; |
| SEQ ID NO: 17: | Dmg-P-R-Sar-Hof-L-Dox; |
| SEQ ID NO: 18: | acetyl-P-H-G-Hof-L-Dox; |
| SEQ ID NO: 19: | acetyl-P-Orn-G-Hof-L-Dox; |
| SEQ ID NO: 20: | acetyl-P-Dap-G-Hof-L-Dox; |
| SEQ ID NO: 21: | acetyl-P-Cit-G-Hof-L-Dox; |
| SEQ ID NO: 22: | acetyl-P-L-G-(O-(3-pyridyl-))Y-L-Dox; |
| SEQ ID NO: 23: | acetyl-P-L-G-(O-(4-pyridyl-))Y-L-Dox; |
| SEQ ID NO: 24: | acetyl-P-L-G-(4-aza-)Hof-L-Dox; |
| SEQ ID NO: 25: | acetyl-P-L-G-(O-benzyl-)S-L-Dox; |
| SEQ ID NO: 26: | Cbz-P-L-G-(O-(4-pyridylmethyl-))Y-L-Dox; |
| SEQ ID NO: 27: | acetyl-P-L-Sar-L-L-Dox; |
| SEQ ID NO: 28: | acetyl-P-(N-Me-)L-G-L-L-Dox; |
| SEQ ID NO: 29: | acetyl-P-L-G-(N-Me-)L-L-Dox; |
| SEQ ID NO: 30: | acetyl-Hyp-L-G-L-L-Dox; |
| SEQ ID NO: 31: | acetyl-Tzc-L-G-L-L-Dox; |
| SEQ ID NO: 32: | acetyl-(Homo-P)-L-G-L-L-Dox; |
| SEQ ID NO: 33: | acetyl-(Homo-P)-L-G-Hof-L-Dox; |
| SEQ ID NO: 34: | acetyl-(Homo-P)-Orn-G-Hof-L-Dox; |
| SEQ ID NO: 35: | acetyl-Nipecotate-L-G-L-L-Dox; |
| SEQ ID NO: 36: | acetyl-Aze-L-G-L-L-Dox; |
| SEQ ID NO: 37: | acetyl-Chg-L-G-L-L-Dox; |
| SEQ ID NO: 38: | acetyl-P-valerolactam-G-L-L-Dox; |

-continued

SEQ ID NO: 41:   acetyl-L-G-L-Y-L-Dox;
SEQ ID NO: 42:   cyclopropylcarbonyl-L-G-L-Y-L-Dox;
SEQ ID NO: 43:   cyclobutylcarbonyl-L-G-L-Y-L-Dox;
SEQ ID NO: 44:   pivaloyl-L-G-L-Y-L-Dox.
SEQ ID NO: 45:   Hyp-G-P-L-G-L-L-Dox;
SEQ ID NO: 46:   acetyl-P-L-G-L-A-L-Dox;
SEQ ID NO: 47:   acetyl-P-L-G-L-Y-L-Dox;
SEQ ID NO: 48:   Peg-P-L-G-L-Y-L-Dox;
SEQ ID NO: 49:   H$_3$CC(=O)NH-Peg-P-L-G-L-Y-L-Dox;
SEQ ID NO: 50:   AcHNCH$_2$CH$_2$N(CH$_2$CH$_2$)$_2$NCH$_2$C(=O)-P-L-G-L-Y-L-Dox;
SEQ ID NO: 51:   acetyl-P-L-G-L-S-L-Dox;
SEQ ID NO: 52:   acetyl-G-P-L-G-L-L-Dox;
SEQ ID NO: 53:   O(CH$_2$CH$_2$)NCH$_2$CH$_2$NHC(=O)-G-P-L-G-L-L-Dox;
SEQ ID NO: 55:   acetyl-P-L-G-L-L-L-Dox;
SEQ ID NO: 58:   Cbz-G-P-L-G-L-L-Dox;
SEQ ID NO: 59:   AcHNCH$_2$CH$_2$N(CH$_2$CH$_2$)$_2$NCH$_2$C(=O)-G-P-L-G-L-L-Dox;
SEQ ID NO: 60:   H$_2$NCH$_2$CH$_2$N(CH$_2$CH$_2$)$_2$NCH$_2$C(=O)-G-P-L-G-L-L-Dox;
SEQ ID NO: 61:   Dmg-P-L-G-L-L-Dox;
SEQ ID NO: 62:   acetyl-γ-E-P-L-G-L-L-Dox;
SEQ ID NO: 65:   methoxyacetyl-G-P-L-G-L-L-Dox;
SEQ ID NO: 66:   Dmg-P-L-G-Tha-L-Dox;
SEQ ID NO: 67:   Dmg-P-L-G-Phg-L-Dox;
SEQ ID NO: 68:   Dmg-P-L-G-(O-benzyl-Y)-L-Dox;
SEQ ID NO: 69:   Dmg-P-L-G-Bip-L-Dox;
SEQ ID NO: 77:   acetyl-G-P-Q-G-L-L-Dox;
SEQ ID NO: 78:   acetyl-G-P-R-G-L-L-Dox;
SEQ ID NO: 82:   acetyl-G-P-L-G-V-L-Dox;
SEQ ID NO: 83:   acetyl-G-P-L-G-Hof-L-Dox;
SEQ ID NO: 84:   acetyl-G-P-L-A-L-L-Dox;
SEQ ID NO: 85:   Dmg-P-I-G-Bip-L-Dox;
SEQ ID NO: 86:   Dmg-P-Chg-G-Bip-L-Dox;
SEQ ID NO: 87:   acetyl-G-P-V-G-L-L-Dox;
SEQ ID NO: 88:   Dmg-P-I-G-L-L-Dox;
SEQ ID NO: 89:   Dmg-P-R-G-Bip-L-Dox;
SEQ ID NO: 91:   acetyl-G-P-L-G-E-L-Dox;
SEQ ID NO: 92:   Dmg-P-R-G-Hof-R-L-Dox;
SEQ ID NO: 95:   Dmg-P-R-G-Bip-R-L-Dox;
SEQ ID NO: 96:   Dmg-P-K-G-Bip-L-Dox;
SEQ ID NO: 97:   Dmg-P-R-Sar-Hof-R-L-Dox;
SEQ ID NO: 98:   acetyl-G-P-L-G-N-L-Dox;
SEQ ID NO: 99:   acetyl-G-P-L-G-S-L-Dox;
SEQ ID NO: 100:  acetyl-G-P-L-G-(4-hydroxy-phenyl-G)-L-Dox;
SEQ ID NO: 101:  acetyl-P-L-G-Hof-H-L-Dox;
SEQ ID NO: 102:  acetyl-P-L-G-Hof-A-L-Dox;
SEQ ID NO: 103:  acetyl-P-L-G-Hof-Y-L-Dox;
SEQ ID NO: 104:  acetyl-P-L-G-Hof-(morpholinylpropyl-G)-L-Dox;
SEQ ID NO: 105:  acetyl-γ-E-P-L-G-Hof-Y-L-Dox;
SEQ ID NO: 106:  succinyl-P-L-G-Hof-Y-L-Dox;
SEQ ID NO: 107:  acetyl-P-L-G-Hof-(O-(4-pyridylmethyl)-Y)-L-Dox;
SEQ ID NO: 108:  acetyl-P-L-G-(homo-Y)-Y-L-Dox;
SEQ ID NO: 109:  acetyl-P-L-G-(4-aza-Hof)-Y-L-Dox;
SEQ ID NO: 110:  acetyl-P-L-G-(O-(4-pyridyl-)-Y)-Y-L-Dox;
SEQ ID NO: 111:  acetyl-P-L-G-(phenylpropyl-G)-Y-L-Dox;
SEQ ID NO: 112:  acetyl-P-L-G-(styryl-A)-Y-L-Dox;
SEQ ID NO: 113:  acetyl-P-L-G-(O-benzyl-S)-Y-L-Dox:
SEQ ID NO: 114:  acetyl-P-(N,N-dimethyl-K)-G-Hof-Y-L-Dox;
SEQ ID NO: 115:  acetyl-P-L-G-Hof-Dap-L-Dox;
SEQ ID NO: 116:  acetyl-P-L-G-Hof-Orn-L-Dox;
SEQ ID NO: 117:  Peg-P-L-G-Hof-Orn-L-Dox;
SEQ ID NO: 118:  acetyl-γ-E-P-L-G-Hof-Orn-L-Dox;
SEQ ID NO: 119:  γ-E-P-L-G-Hof-Orn-L-Dox;
SEQ ID NO: 120:  acetyl-P-Orn-G-Hof-Orn-L-Dox;
SEQ ID NO: 121:  acetyl-P-Orn-G-Hof-Y-L-Dox;
SEQ ID NO: 122:  acetyl-γ-E-P-Orn-G-Hof-E-L-Dox;
SEQ ID NO: 123:  acetyl-P-Orn-G-L-Y-L-Dox;
SEQ ID NO: 124:  acetyl-P-(4-aza-F)-G-L-Y-L-Dox;
SEQ ID NO: 125:  acetyl-P-L-G-Hof-Dab-L-Dox;
SEQ ID NO: 126:  acetyl-P-L-G-Hof-K-L-Dox;
SEQ ID NO: 127:  acetyl-P-L-G-Hof-(N,N-dimethyl-K)-L-Dox;
SEQ ID NO: 128:  Dmg-P-L-G-Hof-(N,N-dimethyl-K)-L-Dox;
SEQ ID NO: 129:  Peg-P-L-G-Hof-(N,N-dimethyl-K)-L-Dox;
SEQ ID NO: 130:  acetyl-γ-E-P-L-G-Hof-(N,N-dimethyl-K)-L-Dox;
SEQ ID NO: 131:  γ-E-P-L-G-Hof-(N,N-dimethyl-K)-L-Dox;
SEQ ID NO: 132:  acetyl-P-L-G-Hof-(N,N-dimethyl-K)-Nle-Dox;
SEQ ID NO: 133:  acetyl-P-L-G-Hof-(N,N-dimethyl-K)-Cha-Dox;
SEQ ID NO: 134:  acetyl-P-L-G-Hof-Cit-L-Dox;
SEQ ID NO: 135:  acetyl-γ-E-P-L-G-Hof-Cit-L-Dox;
SEQ ID NO: 136:  acetyl-P-L-G-Hof-Q-L-Dox;
SEQ ID NO: 137:  acetyl-P-L-G-Hof-(4-aza-F)-L-Dox;
SEQ ID NO: 138:  acetyl-P-L-G-Hof-V-L-Dox;
SEQ ID NO: 139:  acetyl-γ-E-P-L-G-Hof-E-L-Dox;
SEQ ID NO: 140:  acetyl-G-Aze-L-G-L-L-Dox;
SEQ ID NO: 141:  acetyl-(4-fluoro-F)-L-G-L-L-Dox;
SEQ ID NO: 142:  acetyl-(homo-P)-L-G-L-Y-L-Dox;
SEQ ID NO: 143:  acetyl-(homo-P)-L-G-Hof-Orn-L-Dox;
SEQ ID NO: 144:  acetyl-Aze-L-G-L-Y-L-Dox;
SEQ ID NO: 145:  acetyl-Aze-L-G-Hof-Orn-L-Dox;
SEQ ID NO: 154:  acetyl-P-L-G-L-L-A-L-Dox;
SEQ ID NO: 155:  acetyl-P-L-G-L-Y-A-L-Dox;
SEQ ID NO: 156:  acetyl-G-P-L-G-L-A-L-Dox;
SEQ ID NO: 157:  acetyl-P-L-G-L-A-A-L-Dox;
SEQ ID NO: 158:  acetyl-P-L-G-L-A-L-L-Dox;
SEQ ID NO: 159:  acetyl-P-L-G-L-L-S-L-Dox;
SEQ ID NO: 160:  acetyl-P-L-G-L-L-L-L-Dox;
SEQ ID NO: 161:  Dmg-P-L-G-L-Y-L-Dox;
SEQ ID NO: 162:  Dmg-P-R-G-Phg-Y-L-Dox;
SEQ ID NO: 163:  acetyl-G-P-L-G-L-R-L-Dox;
SEQ ID NO: 164:  4-(2-(5,6,7,8-tetrahydronaphthenyl))butyl-G-Hof-Y-L-Dox;
SEQ ID NO: 165:  acetyl-P-L-G-Hof-(N-methylpiperazinepropyl-G)-L-Dox;
SEQ ID NO: 166:  tetrazoleacetyl-P-L-G-Hof-Y-L-Dox;
SEQ ID NO: 167:  tetrazoleacetyl-P-L-G-(O-benzyl-S)-Y-L-Dox;
SEQ ID NO: 168:  tetrazoleacetyl-P-L-G-Hof-Y-Nle-Dox;
SEQ ID NO: 169:  P-L-G-(O-benzyl-S)-Y-L-Dox;
SEQ ID NO: 170:  acetyl-P-L-G-Hof-(homoY)-L-Dox;
SEQ ID NO: 171:  acetyl-P-AzaHof-G-AzaHof-Y-L-Dox;
SEQ ID NO: 172:  acetyl-P-L-G-(O-allyl-S)-Y-L-Dox;
SEQ ID NO: 173:  acetyl-P-L-G-(4-nitro-Hof)-Y-L-Dox;
SEQ ID NO: 174:  acetyl-P-L-G-Hof-AzaHof-L-Dox;
SEQ ID NO: 175:  acetyl-P-L-G-(O-methyl-S)-Y-L-Dox;
SEQ ID NO: 176:  acetyl-γ-E-P-L-G-(O-benzyl-S)-Y-L-Dox;
SEQ ID NO: 177:  acetyl-γ-E-P-L-G-(O-benzyl-S)-Y-Nle-Dox;
SEQ ID NO: 178:  3-pyridinecarbonyl-P-L-G-Hof-Y-L-Dox;
SEQ ID NO: 179:  2-pyrazinecarbonyl-P-L-G-Hof-Y-L-Dox;
SEQ ID NO: 180:  acetyl-P-L-G-Hof-(N,N-dimethyl-K)-Nle-Dox;
SEQ ID NO: 182:  acetyl-P-L-G-Hof-Y-Hol-Dox;
SEQ ID NO: 183:  acetyl-P-L-G-Thr(O-Benzyl)-Y-L-Dox;
SEQ ID NO: 184:  acetyl-γ-E-P-L-G-Hof-Y-Nle-Dox;

In another preferred embodiment the invention provides a compound selected from:

| SEQ ID NO: 39:  | acetyl-G-P-L-G-L-F-Dox; |
| SEQ ID NO: 40:  | acetyl-G-P-L-G-F-F-Dox; |
| SEQ ID NO: 54:  | acetyl-G-P-L-G-L-Y-Dox; |
| SEQ ID NO: 56:  | acetyl-G-P-L-G-Bip-F-Dox; |
| SEQ ID NO: 57:  | acetyl-G-P-L-G-Nle-F-Dox; |
| SEQ ID NO: 63:  | acetyl-G-P-L-G-Tha-F-Dox; |
| SEQ ID NO: 64:  | acetyl-G-P-L-G-Phg-F-Dox; |
| SEQ ID NO: 70:  | acetyl-G-P-L-G-F-Bip-Dox; |
| SEQ ID NO: 71:  | acetyl-G-P-L-G-L-Bip-Dox; |
| SEQ ID NO: 72:  | acetyl-G-P-L-G-(2Nal)-Bip-Dox; |
| SEQ ID NO: 73:  | acetyl-G-P-L-G-F-A-Dox; |
| SEQ ID NO: 74:  | acetyl-G-P-L-G-Bip-A-Dox; |
| SEQ ID NO: 75:  | acetyl-G-P-L-G-L-A-Dox; |
| SEQ ID NO: 76:  | acetyl-G-P-L-G-(O-benzyl-Y)-F-Dox; |
| SEQ ID NO: 79:  | acetyl-G-P-L-G-(4-pyridyl-A)-Dox; |
| SEQ ID NO: 80:  | acetyl-G-P-L-G-R-Dox; |
| SEQ ID NO: 81:  | acetyl-G-P-L-G-W-Dox; |
| SEQ ID NO: 90:  | acetyl-G-P-L-G-L-(O-benzyl-Y)-Dox; |
| SEQ ID NO: 93:  | acetyl-G-P-L-G-L-E-Dox; |
| SEQ ID NO: 94:  | acetyl-G-P-L-G-Bip-E-Dox; |
| SEQ ID NO: 146: | acetyl-P-L-G-L-Y-G-Dox; |
| SEQ ID NO: 147: | acetyl-P-L-G-Hof-Y-G-Dox; |
| SEQ ID NO: 148: | acetyl-P-L-G-L-Y-(β-homo-L)-Dox; |
| SEQ ID NO: 149: | acetyl-P-L-G-Hof-Y-(β-homo-L)-Dox; |
| SEQ ID NO: 150: | acetyl-P-L-G-L-Y-(β-Ala)-Dox; |
| SEQ ID NO: 151: | acetyl-P-L-G-L-Y-Ahx-Dox; |
| SEQ ID NO: 152: | acetyl-P-L-G-L-Y-Aph-Dox; |

-continued

| | |
|---|---|
| SEQ ID NO: 153: | acetyl-P-L-G-L-Y-Amh-Dox; |
| SEQ ID NO: 181: | acetyl-P-L-G-Hof-Y-Hos-Dox; |

In second embodiment the invention provides a pharmaceutical composition comprising a compound of Formula (I) or (Ia) and a pharmaceutically acceptable carrier.

In third embodiment the invention provides for a method of treating a mammal afflicted with a cancer comprising administering to a mammal afflicted with a cancer a therapeutically effective amount of a compound of Formula (I) or (Ia).

In a preferred embodiment the invention provides for a method of treating a mammal afflicted with a cancer wherein the cancer is a breast, ovarian, brain, stomach, lung, colon, prostate or liver cancer or wherein the cancer is a leukemia, lymphoma, carcinoma, sarcoma, or melanoma.

In fourth embodiment the invention provides for a method of delivering a compound to the cells of a mammal afflicted with a cancer comprising contacting the cells of a mammal afflicted with a cancer with a of Formula (I) or (Ia), wherein the contacting is in the presence of a peptidase comprising a matrixin.

In a preferred embodiment the invention provides for a method wherein the cancer is a breast, ovarian, brain, stomach, lung, colon, prostate or liver cancer or wherein the cancer is a leukemia, lymphoma, carcinoma, sarcoma, or melanoma.

In a fifth embodiment the invention provides for a compound of Formula (1):

$$E^{cp}\text{-}A \quad (I)$$

comprising an enzyme-cleavable peptide, $E^{cp}$, conjugated to an antineoplastic agent, A.

In a preferred embodiment the invention provides for a compound of Formula (I) wherein the antineoplastic agent is an anthracycline, vinca alkaloid, bleomycin, mitomycin, taxane, cytotoxic nucleotide, pteridine or podophyllotoxin.

In a preferred embodiment the invention provides for a compound of Formula (I) wherein the antineoplastic agent is an anthracycline.

In a preferred embodiment the invention provides for a compound of Formula (I) wherein the antineoplastic agent is the anthracycline doxorubicin.

In a preferred embodiment the invention provides for a compound of Formula (I) wherein the amino acid sequence is selected from the group consisting of

| | |
|---|---|
| PLGL | SEQ ID NO: 203 |
| PLGLL | SEQ ID NO: 212 |
| PLGLAL | SEQ ID NO: 213 |
| PLGLYL | SEQ ID NO: 214 |
| PLGLYAL | SEQ ID NO: 215 |
| PLGLAAL | SEQ ID NO: 216 |
| PLGLLSL | SEQ ID NO: 217 |
| PLGLLAL | SEQ ID NO: 218 |
| PLGLLYL | SEQ ID NO: 204 |
| GPLGL | SEQ ID NO: 205 |
| GPLGLL | SEQ ID NO: 219 |
| PLGHof | SEQ ID NO: 210 |
| PLG-(O-Benzyl)-S | SEQ ID NO: 220 |
| PLGHofYL | SEQ ID NO: 221 |
| PLG-(O-Benzyl)-SYL | SEQ ID NO: 222 |

-continued

| | |
|---|---|
| PLGHofEL | SEQ ID NO: 223 |
| GPLGLAL | SEQ ID NO: 224 |

In a preferred embodiment the invention provides for a compound of Formula (I) wherein the amino acid sequence is selected from the group consisting of

| | |
|---|---|
| PLGL | SEQ ID NO: 203 |
| PLGLL | SEQ ID NO: 212 |
| PLGLAL | SEQ ID NO: 213 |
| PLGLYL | SEQ ID NO: 214 |
| PLGLLAL | SEQ ID NO: 218 |
| PLGLLYL | SEQ ID NO: 204 |
| GPLGL | SEQ ID NO: 205 |
| GPLGLL | SEQ ID NO: 219 |
| GPLGLAL | SEQ ID NO: 224 |

In a preferred embodiment the invention provides for a compound of Formula (I) wherein the enzyme-cleavable peptide comprises an amino acid sequence recognized by a peptidase wherein the peptidase is a matrixin.

In a preferred embodiment the invention provides for a compound of Formula (I) wherein the peptidase is a matrixin comprising MMP-2, MMP-9, or MMP-14.

In a preferred embodiment the invention provides for a compound of Formula (I) wherein the agent is doxorubicin and wherein the enzyme-cleavable peptide comprises an amino acid sequence selected from the group consisting of

| | |
|---|---|
| PLGL | SEQ ID NO: 203 |
| PLGLL | SEQ ID NO: 212 |
| PLGLAL | SEQ ID NO: 213 |
| PLGLYL | SEQ ID NO: 214 |
| PLGLLAL | SEQ ID NO: 218 |
| PLGLLYL | SEQ ID NO: 204 |
| PLGLYAL | SEQ ID NO: 215 |
| GPLGL | SEQ ID NO: 205 |
| GPLGLL | SEQ ID NO: 219 |
| GPLGLAL | SEQ ID NO: 224 |

In a preferred embodiment the invention provides for a compound of Formula (I) wherein the agent is doxorubicin and wherein the enzyme-cleavable peptide comprises an amino acid sequence recognized by a peptidase selected from the group consisting of matrixin MMP-2, MMP-9, or MMP-14.

In another preferred embodiment the invention provides for a pharmaceutical composition comprising the compound of Formula (I) and a pharmaceutically acceptable carrier.

In another preferred embodiment the invention provides method of delivering a compound to the cells of a mammal afflicted with a cancer comprising contacting the cells of a mammal afflicted with a cancer with the compound of Formula (I), wherein the contacting is in the presence of a peptidase comprising a matrixin.

In another preferred embodiment the invention provides a method of delivering a compound of Formula (I) to the cells of a mammal afflicted with a cancer wherein the cancer is a breast, ovarian, brain, stomach, lung, colon, prostate or liver cancer or wherein the cancer is a leukemia, lymphoma, carcinoma, sarcoma, or melanoma.

In another preferred embodiment the invention provides a method of delivering a compound of Formula (I) to the cells of a mammal afflicted with a cancer wherein the anticancer agent is an anthracycline, vinca alkaloid, bleomycin, mitomycin, taxane, cytotoxic nucleotide, pteridine or podophyllotoxin.

In another preferred embodiment the invention provides a method of delivering a compound of Formula (I) to the cells of a mammal afflicted with a cancer wherein the anticancer agent is an anthracycline, vinca alkaloid, bleomycin, mitomycin, taxane, cytotoxic nucleotide, pteridine or podophyllotoxin and wherein the agent is the anthracycline doxorubicin.

Also included in the present invention are compounds as set forth above wherein the enzyme-cleavable peptide is selectively recognized by a matrixin comprising MMP-2, MMP-9, and/or MMP-14 and not selectively recognized by the enzyme human fibroblast activation protein (FAPα).

Also included in the present invention are compounds as set forth above wherein the amino acid Laa is not proline or a proline analogue wherein the substituents on the alpha nitrogen and substituents on the alpha carbon form a cyclic group.

Also included in the present invention are compounds as set forth above provided that the amino capping group, Cap, is not a polyhydroxyalkanoyl, that is, wherein the hydroxyalkanoyl capping groups are limited to those with one hydroxy substituent on the alkanoyl group.

Also included in the present invention are compounds as set forth above wherein the enzyme-cleavable peptide is selectively recognized by a matrixin comprising MMP-2, MMP-9, and/or MMP-14 and not selectively recognized by the enzyme Trouase.

Also included in the present invention are compounds as set forth above provided that the amino acid Xa2 is a natural amino acid.

Also included in the present invention are compounds as set forth above provided that Cap is not a non-natural amino acid or succinyl.

Also included in the present invention are compounds as set forth above wherein the enzyme-cleavable peptide is selectively recognized by a matrixin comprising MMP-2, MMP-9, and/or MMP-14 and not selectively recognized by prostate specific antigen (PSA).

Also included in the present invention are compounds as set forth above provided $E^{CP}$ does not comprise a dipeptide linkage selected from-Tyr-Ser-; -Tyr-Thr-; -Phe-Ser-; -Gln-Ser-; -Gln-Thr-, and -Asn-Ser.

Also included in the present invention are compounds as set forth above provided $E^{CP}$ is not-Gly-Gly-Arg-Leu-(SEQ ID NO: 225).

Also included in the present invention are compounds as set forth above provided $E^{CP}$ is not-Gly-Val-Phe-Arg-(SEQ ID NO: 226).

Also included in the present invention are compounds as set forth above provided $E^{CP}$ is not-Ala-Pro-Gly-Leu-(SEQ ID NO: 227).

Also included in the present invention are compounds as set forth above provided $E^{CP}$ is not 2-thienylalanine-Gly-Ala-Leu-(SEQ ID NO: 228).

Also included in the present invention are compounds as set forth above provided $E^{CP}$ is not 2-naphthylalanine-Gly-Ala-Leu-(SEQ ID NO: 229).

Also included in the present invention are compounds as set forth above provided $E^{CP}$ is not-Gly-Leu-Gly-Leu-(SEQ ID NO: 230). "Antineoplastic agents" as used herein means agents which have cytotoxic effects on tumor cells, these include both compounds such as alkylating agents, tubulin-binding agents, and antiproliferative agents, as well as proteins, e.g., tumor necrosis factor, interferons and various growth factors, which may negatively impact upon the growth of cancerous cells. Specific "antineoplastic agents" suitable for use herein include, without limitation: anthracyclines, bleomycin, vinca alkaloids (e.g., vincristine and vinblastine), mitomycin, cytotoxic nucleotides, taxanes (e.g., paclitaxel and taxotere, (see DeGroot)), pteridines, podophyllotoxins, and folic acid derivatives (see Lu). Such compounds may be modified, e.g., to enhance the compounds' potential therapeutic efficacies or to ease their conjugation to peptides, at various points on their structures, by means well known to ordinarily skilled artisans.

As used herein the "antineoplastic agents" which are anthracyclines are intended to include doxorubicin, doxorubicin derivatives, and doxorubicin anologues, examples of which include, but are not limited to, doxorubicin (adriamycin), daunorubicin (daunomycin), epirubicin, detorubicin, idarubicin, esorubicin, and carminomycin, as well as, mitoxantrone. A preferred anthracycline is doxorubicin, referred to herein as "Dox" or "dox".

Enzyme cleavable peptides comprise amino acid sequences recognized and cleaved by membrane bound and/or cell-secreted peptidases, which are peptide-cleaving enzymes well known in the art to recognize particular amino acid sequences and to cleave said sequences between specific amino acids (see, e.g., Ames and Quigley et al.; Knauper et al., McGeehan et al., Nagase et al., Nakajima et al., Odake et al.). Such enzymes include, for example and without limitation, matrix metalloproteinases or "MMP's" (also referred to herein as matrixins), e.g., MMP-2, MMP-9, MMP-14, serine proteases, cysteine proteases, elastase, stromelysins, human collagenases, cathepsins, granzymes, dipeptidyl peptidases, plasmins, plasminogen activators, lysozymes and e.g., aminopeptidase P, aminopeptidase A, and aminopeptidase N. Peptides with suitable MMP substrate selectivity suitable for conjugation to cytotoxic agents herein include, for example and without limitation, those having the amino acid sequences:

| | |
|---|---|
| PLGL | SEQ ID NO: 203 |
| PLGLL | SEQ ID NO: 212 |
| PLGLAL | SEQ ID NO: 213 |
| PLGLYL | SEQ ID NO: 214 |
| PLGLLAL | SEQ ID NO: 218 |
| PLGLALL | SEQ ID NO: 232 |
| PLGLLLL | SEQ ID NO: 233 |
| PLGLLYL | SEQ ID NO: 204 |
| PLGLYAL | SEQ ID NO: 215 |
| PLGLAAL | SEQ ID NO: 216 |
| PLGLLSL | SEQ ID NO: 217 |
| GPLGL | SEQ ID NO: 205 |
| GPLGLY | SEQ ID NO: 231 |
| GPLGLL | SEQ ID NO: 219 |
| GPLGLAL | SEQ ID NO: 224 |
| DPLGL | SEQ ID NO: 206 |
| PEQGL | SEQ ID NO: 207 |
| PQGL | SEQ ID NO: 208 |
| PLGL-Dpa-AR | SEQ ID NO: 209 | and similar sequence (Nagase).

Each of these amino acid sequences optionally includes any of the various modified amino acids, e.g., hydroxyproline, described herein, and each of the sequences is optionally modified by any of the amino or carboxy terminal modifications, e.g., acetyl, described herein. Thus, in addition to the specific amino acid sequences set forth, this invention also provides corresponding versions containing one or more natural, modified, or unnatural amino acids and one or more terminal modifications, e.g., this invention provides peptides comprising the amino acid sequence PLG- LYL (SEQ ID NO:214), as well as Hyp-PLGLYL (SEQ ID NO: 234), AcPLGLYL (SEQ ID NO: 235) and AcHypPLGLYL (SEQ ID NO: 236).

As used herein "matrixin" is intended to generically describe matrix metalloproteinases or MMP's as a class of enzymes which recognize the enzyme-cleavable peptides of the compounds of the present invention. Preferred MMP's are MMP-2, MMP-9, and/or MMP-14. Matrixin does not describe the enzyme neprilysin.

As used herein "a bond cleavable by a matrixin" is intended to describe an amide bond of the enzyme-cleavable peptide which is amenable to proteolytic cleavage in vitro by a matrixin, as defined herein. It is intended that matrixins, as defined herein, are preferably selective for the bond cleavable by a matrixin. It is also understood that proteolytic degradation of the enzyme-cleavable peptide may occur at any bond on the enzyme-cleavable peptide following the administration of the compound in vivo.

Enzyme cleavable peptides must contain the minimum number of amino acids, substitutions or modifications thereof, for recognition and cleavage by the corresponding peptidase (e.g., PLGL (SEQ ID NO: 203), AA). Alternatively, the peptides' amino acid sequences may comprise one or more amino acids in addition to those minimally necessary for peptidase-mediated cleavage (e.g., peptides comprising, in order, the amino acids P, L, G and L may have the amino acid sequence PLGLL (SEQ ID NO: 212), and peptides comprising the amino acid sequence AA may actually have the sequence AAPV). Such additional amino acids are included in the peptides, at the amino and/or carboxy terminal ends, for a variety of reasons well known to ordinarily skilled artisans given the teachings of this invention, e.g., to further decrease the availability to nonpeptidase-secreting cells of compounds to which the peptides are conjugated. Additionally, the amino acid sequence remaining on the cytotoxic agent after the initiating peptidase cleavage event must be composed of sequences that are capable of being removed or processed by cellular aminopeptidases after tumor associated peptidase cleavage. (e.g., LL-Dox or LAL-Dox)

Compounds of the present invention conjugated to enzyme cleavable peptides recognized and cleaved by matrix metalloproteinases MMP-2, MMP-9, and/or MMP-14, are believed to recognize particular amino acid sequences and to cleave said sequences containing glycine or sarcocine at the cleavage site. As such, enzyme cleavable peptides of the present invention contain the dipeptides -Gly-Xp1- or -Sar-Xp1-at the cleavage site wherein Xp1 is an amino acid which forms a bond to Gly or Sar cleavable by a free matrixin or matrix metalloproteinase. Preferred examples of Xp1 include, but are not limited to, Leu, Hof, azaHof, Ser(Omethyl), and Ser(Obenzyl). In addition to the above dipeptides, MMP-2, MMP-9, and/or MMP-14, are believed to recognize and cleave amino acid sequences -Paa-Xaa-Gly-Xp1- and -Paa-Xaa-Sar-Xp1-, wherein Paa is a proline, proline derivative, or proline mimetic and Xaa is an amino acid. Preferred examples of Paa include, but are not limited to, Pro and Hyp.

In addition to the matrix metalloproteinases (MMP's) MMP-2, MMP-9, and MMP-14 disclosed above, the present invention intends for the use of matrixins MMP-13 and MMP-8 to also be used in a cytotoxic peptide conjugate targeting approach. Enzyme/amino acid recognition sequence pairings include, for example, MMP-13 recognizing the sequence PLGL (SEQ ID NO: 203), (see, e.g., Knauper et al.), and MMP-8 recognizing the sequences AAPF or AAPM; particularly where these have been N-terminal modified by succinyl or methoxysuccinyl (see, e.g., Nakajima et al). The contents of these descriptions are incorporated herein by reference.

Such peptides, as well as other enzyme-cleavable peptides, including peptides containing substitute, modified, unnatural or natural amino acids in their sequences, as well as peptides modified at their amino or carboxy terminus, are made from their component amino acids by a variety of methods well known to ordinarily skilled artisans, and practiced thereby using readily available materials and equipment, (see, e.g., *The Practice of Peptide Synthesis* (2nd. ed.), M. Bodanskzy and A. Bodanskzy, Springer-Verlag, New York, N.Y. (1994), the contents of which are incorporated herein by reference). These include, for example and without limitation: solid-phase synthesis using the Fmoc protocol (see, e.g., Change and Meieinhofer, Int. J. Pept. Protein Res. 11:246–9 (1978)). Other documents describing peptide synthesis include, for example and without limitation: Miklos Bodansky, *Peptide Chemistry, A Practical Textbook* 1988, Springer-Verlag, N.Y.; *Peptide Synthesis Protocols*, Michael W. Pennington and Ben M. Dunn editors, 1994, Humana Press Totowa, N.J.

As described hereinabove, enzyme-cleavable peptides comprise an amino acid sequence which serves as the recognition site for a peptidase capable of cleaving the peptide. The amino acids comprising the enzyme cleavable peptides may include natural, modified, or unnatural amino acids, wherein the natural, modified, or unnatural amino acids may be in either D or L configuration. Natural amino acids include the amino acids alanine, cysteine, aspartic acid, glutamic acid, phenylalanine, glycine, histidine, isoleucine, lysine, leucine, methionine, asparganine, proline, glutamine, arginine, serine, threonine, valine, tryptophan, and tyrosine. Natural amino acids, as used herein, have the following abbreviations:

| 1-Letter Code | 3-Letter Code | Name |
|---|---|---|
| A | Ala | Alanine |
| C | Cys | Cysteine |
| D | Asp | Asparticacid |
| E | Glu | Glutamic acid |
| F | Phe | Phenylalanine |
| G | Gly | Glycine |
| H | His | Histidine |
| I | Ile | Isoleucine |
| K | Lys | Lysine |
| L | Leu | Leucine |
| M | Met | Methionine |
| N | Asn | Asparagine |
| P | Pro | Proline |
| Q | Gln | Glutamine |
| R | Arg | Arginine |
| S | Ser | Serine |
| T | Thr | Threonine |
| U | Scy | Selenocysteine |
| V | Val | Valine |
| W | Trp | Tryptophan |
| Y | Tyr | Tyrosine |

Enzyme-cleavable peptides may also comprise a variety of unnatural or modified amino acids suitable for substitution into the enzyme-cleavable peptide of the invention. A definite list of unnatural amino acids is disclosed in Roberts and Vellaccio, *The Peptides*, Vol. 5, 341–449 (1983) Academic Press, New York, and is incorporated herein by reference for that purpose. Examples of unnatural or modified amino acids used herein include, without limitation:

| 3-Letter Code | Name |
|---|---|
| Aaa | alpha-amino acid |
| Aad | 2-aminoadipic acid (2-aminohexanedioic acid) |
| Aan | alpha-asparagine |
| Abu | 2-aminobutanoic acid or 2-aminobutyric acid |
| γAbu | 4-aminobutyric acid |
| Aca | 2-aminocapric acid (2-aminodecanoic acid) |
| Acp | 6-aminocaproic acid |
| Agn | alpha-glutamine |
| Ahe | 2-aminoheptanoic acid |
| Ahx | 6-aminohexanoic acid |
| Aib | alpha-aminoisobutyric acid (2-aminoalanine) |
| 3-Aib | 3-aminoisobutyric acid |
| β-Ala | beta-alanine |
| aHyl | allo-hydroxylysine |
| aIle | allo-isoleucine |
| Amh | 4-amino-7-methylheptanoic acid |
| Aph | 4-amino-5-phenylpentanoic acid |
| Apm | 2-aminopimelic acid (2-aminoheptanedioic acid) |
| App | gamma-amino-beta-hydroxybenzenepentanoic acid |
| Asu | 2-aminosuberic acid (2-aminooctanedioic acid) |
| Aze | 2-carboxyazetidine |
| Bal | beta-alanine |
| Bas | beta-aspartic acid |
| Bip | Biphenylalanine |
| Bly | 3,6-diaminohexanoic acid (beta-lysine) |
| Bua | butanoic acid |
| Bux | 4-amino-3-hydroxybutanoic acid |
| Cap | gamma-amino-beta-hydroxycyclohexanepentanoic acid) |
| Cba | cyclobutyl alanine |
| Cha | Cyclohexylalanine |
| Chg | Cyclohexylglycine |
| Cit | N5-aminocarbonylornithine |
| Cpa | cyclopentyl alanine |
| Cta | cyclopropyl alanine |
| Cya | 3-sulfoalanine or cysteic acid |
| Dab | 2,4-diaminobutanoic acid |
| Dap | diaminopropionic acid |
| Dbu | 2,4-diaminobutyric acid |
| Dpa | diphenyl alanine |
| Dmg | N,N-dimethylglycine |
| Dpm | diaminopimelic acid |
| Dpr | 2,3-diaminopropanoic acid or 2,3-diaminopropionic acid |
| Edc | S-ethylthiocysteine |
| EtAsn | N-ethylasparagine |
| EtGly | N-ethylglycine |
| Faf | 4-aza-phenylalanine |
| Fph | 4-fluoro-phenylalanine |
| Ggu | gamma-glutamic acid or (γ-E) or (γ-Glu) |
| Gla | gamma-carboxyglutamic acid |
| Glc | hydroxyacetic acid (glycolic acid) |
| Glp | pyroglutamic acid |
| Har | homoarginine |
| Hca | homocysteic acid |
| Hcy | homocysteine |
| Hhs | homohistidine |
| Hiv | 2-hydroxyisovaleric acid |
| Hof | homophenylalanine |
| Hol | homoleucine or homo-L |
| Hop | homoproline or homo-P |
| Hos | homoserine |
| Hse | homoserine |
| Hva | 2-hydroxypentanoic acid |
| Hyl | 5-hydroxylysine |
| Hyp | 4-hydroxyproline |
| Inc | 2-carboxyoctahydroindole |
| Iqc | 3-carboxyisoquinoline |
| Iva | isovaline |
| Lac | 2-hydroxypropanoic acid (lactic acid) |
| Maa | mercaptoacetic acid |
| Mba | mercaptobutanoic acid |
| MeGly | N-methylglycine or sarcosine |
| Mhp | 4-methyl-3-hydroxyproline |
| Mpa | mercaptopropanoic acid |
| Nle | norleucine |
| Npa | nipecotic acid |
| Nty | nortyrosine |
| Nva | norvaline |

-continued

| 3-Letter Code | Name |
|---|---|
| Oaa | omega-amino acid |
| Orn | ornithine |
| Pen | penicillamine (3-mercaptovaline) |
| Phg | 2-phenylglycine |
| Pip | 2-carboxypiperidine |
| Sar | sarcosine (N-methylglycine) |
| Spa | 2-amino-3-(4-sulfophenyl)propionic acid |
| Spg | 1-amino-1-carboxycyclopentane |
| Sta | statin (4-amino-3-hydroxy-6-methylheptanoic acid) |
| Tha | 3-thienylalanine |
| Tml | epsilon-N-trimethyllysine |
| Tza | 3-thiazolylalanine |
| Tzc | thiazolidine 4-carboxylic acid |
| Und | undefined |
| Xaa | any amino acid |
| Wil | alpha-amino-2,4-dioxopyrimidinepropanoic acid |
| 2Nal | 2-naphthylalanine |

Enzyme-cleavable peptides may also comprise a variety of modified amino acids wherein an amine or hydroxy function of the amino acid has been chemically modified with an alkyl group, an alkenyl group, a phenyl group, a phenylalkyl group, a heterocyclic group, a heterocyclicalkyl group, a carbocyclic group, or a carbocyclicalkyl group. Examples of chemical modification substituents include, but are not limited to, methyl, ethyl, propyl, butyl, allyl, phenyl, benzyl, pyridyl, pyridylmethyl, and imidazolyl. "The Peptides" Vol 3, 3–88 (1981) discloses numerous suitable sidechain functional groups for modifying amino acids, and is herein incorporated for that purpose. Examples of modified amino acids include, but are not limited to, N-methylated amino acids, N-methylglycine, N-ethylglycine, N-ethylasparagine, N,N-dimethyllysine, N'-(2-imidazolyl)lysine, O-methyltyrosine, O-benzyltyrosine, O-pyridyltyrosine, O-pyridylmethyltyrosine, O-methylserine, O-t-butylserine, O-allylserine, O-benzylserine, O-methylthreonine, O-t-butylthreonine, O-benzylthreonine, O-methylaspartic acid, O-t-butylaspartic acid, O-benzylaspartic acid, O-methylglutamic acid, O-t-butylglutamic acid, and O-benzylglutamic acid, Enzyme-cleavable peptides may also comprise a modified amino acid which is 4-azahydroxyphenylalanine (4-azaHof or azaHof), 4-aminomethylalanine, 4-pryidylalanine, 4-azaphenylalanine, morpholinylpropyl glycine, piperazinylpropyl glycine, N-methylpiperazinylpropyl glycine, 4-nitro-hydroxyphenylalanine, 4-hydroxyphenyl glycine, or a 2-(4,6-dimethylpyrimidinyl)lysine.

Enzyme-cleavable peptides may also comprise an amino acid designated Paa, which is the natural amino acid proline or can be a modified or unnatural amino acid which mimics proline. "Proline mimetics", as used herein, are of the general formula

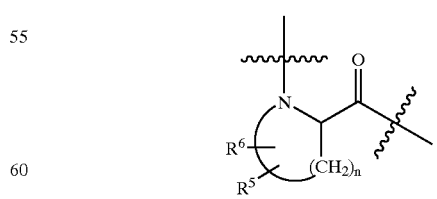

wherein $R^5$ is selected from H, halogen, $C_1$–$C_6$ alkyl, —OH, $C_1$–$C_6$ alkoxy, hydroxymethyl-, phenoxy, and benzyloxy; $R^6$ is selected from H, $C_1$–$C_6$ alkyl, —OH, $C_1$–$C_6$ alkoxy; and n is 2, 3, 4, or 5. Preferred proline mimetics are of the general formula

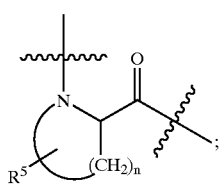

wherein $R^5$ is selected from H, halogen, $C_1$–$C_6$ alkyl, —OH, $C_1$–$C_6$ alkoxy, and benzyloxy; and n is 2, 3, 4, or 5. More preferred n is 3 or 4. Examples of proline mimetics are 4-hydroxyproline, 3-methylproline, 4-methylproline, 5-methylproline, 4,4-dimethylproline, 4-fluoroproline, 4,4-difluoroproline, 4-bromoproline, 4-chloroproline, 4-hydroxymethylproline, 3-hydroxyproline, 3-hydroxy-5-methylproline, 3,4-dihydroxyproline, 3-phenoxyproline, 2-azetidinecarboxylic acid, 4-methyl-2-azetidinecarboxylic acid, pipecolic acid, 5-hydroxypipecolic acid, and 4,5-dihydroxypipecolic acid. Preferred examples of proline mimetics are 4-hydroxyproline, 2-azetidinecarboxylic acid, and pipecolic acid. Examples of Paa include, but are not limited to Pro, 4-hydroxyproline, dihydroxyproline, 2-carboxyazetidine, homo-Pro, cyclohexylglycine, 4-fluorophenylalanine, nipecotic acid, and thiazolidine 4-carboxylic acid.

Enzyme-cleavable peptides have amino acid sequences wherein one or more of the amino acids is optionally substituted by homologous or isoteric amino acids, such that the peptides recognition and cleavage by cell-secreted peptides is not adversely affected. For example, and without limitation, the following amino acid substitutions may be made (in either direction): A-G; R-K-Orn; N-Q; D-E; 1-V-L-M-Nle; F-W-Y; and S-T.

Moreover, enzyme cleavable peptides are optionally modified at the end not conjugated to the antineoplastic agent by what is known in the art as a capping group; for example, the N-terminus of the enzyme cleavable peptide is modified with a N-terminus capping group or an "amino capping group". Such modifications are for a number of reasons; for example, to increase plasma stability of the peptide against enzymatic degradation by non selective enzymes in the plasma or to increase solubility.

Amino capping groups are known in the art and occur in a variety of ways, for example, various acyl, thioacyl, alkyl, sulfonyl, phosphoryl, and phosphinyl groups comprised of 1 to 20 carbon atoms; wherein substituents on these groups may be either alkyl, aryl, alkylaryl, and so forth, which may contain the heteroatoms, O, S, and N as a substituent or in-chain component. A number of amino capping groups are recognized by those skilled in the art of peptide synthesis. Gross and Meinhoffer, eds., *The Peptides*, Vol 3; 3–88 (1981), Academic Press, New York, and Greene and Wuts Protective Groups in Organic Synthesis, 315–405 (1991), J. Wiley and Sons, Inc., New York disclose numerous suitable amine protecting groups useful for the invention herein and they are incorporated herein by reference for that purpose.

In addition to the above, more preferred "amino capping groups" may be alkanoyls, hydroxylated alkanoyls, polyhydroxylated alkanoyls, aroyls, hydroxylated aroyls, polyhydroxylated aroyls, cycloalkyloyls, heterocycloyls, polyethyleneglycols, glycosylates, sugars, carboxy sugars, amino acids, dicarboxylic acids, and crown ethers; each linked to the N-terminal end of the peptide by way of an amide linkage. Examples of amino capping groups include, but are not limited to, acetyl (Ac), pivaloyl, methoxyacetyl, malonyl, succinyl (Suc), glutaryl, benzoyl, methoxy-succinyl (MeO-Suc), pyridinecarbonyl, pyrazinecarbonyl, benzyloxycarbonyl (Cbz), and t-butoxycarbonyl. Alternatively, amino capping groups containing an amine function, such as various carboxy sugars and amino acids containing basic amines; can be linked to the N-terminus of the peptide conjugate by a urea linkage.

Polyethyleneglycols as a class of compounds known as amino capping groups are ethyleneoxy compounds of general formula $H_3CO$—$(CH_2CH_2O)_t$—$CH_2C(=O)$—, wherein t is 1 to 10. Preferred polyethyleneglycols are where t is 1, 2, 3, or 4; more preferred is where t is 1 or 2. Unless otherwise specified, "polyethyleneglycol" or "PEG" or "Peg" means an amino capping group of formula $H_3COCH_2CH_2OCH_2CH_2OCH_2C(=O)$—. Polyethyleneglycols as amino capping groups can be modified to include amino-polyethyleneglycols of formula $H_2N$—$(CH_2CH_2O)_t$-$CH_2C(=O)$—, wherein t is 1, 2, 3, or 4, as well as acetamido-polyethyleneglycols of formula $H_3CC(=O)HN$—$(CH_2CH_2O)_t$—$CH_2C(=O)$—, wherein t is 1, 2, 3, or 4; as well as carboxymethyl-polyethyleneglycols of formula $HO_2CCH_2O$ $(CH_2CH_2O)_t$—$CH_2C(=O)$—, wherein t is 1, 2, 3, or 4.

Moreover, an amino capping group may optionally be an amino acid modified by an alkanoyl, a dicarboxylic acid, a tricarboxylic acid, or a dicarboxylic acid ester. Examples include, but are not limited to, an acetyl (Ac), methoxyacetyl, malonyl, succinyl (Suc), glutaryl, 3-hydroxy-3-methylglutaryl (HMG), citryl, methoxy-succinyl (MeO-Suc), methoxy-malonyl, or methoxy-glutaryl group modified on the amino terminus of, for example, serine or gamma-glutamic acid. For example, acetyl-serine (Ac-Ser), methoxysuccinyl-serine (MeO-Suc-Ser), and succinyl-serine (Suc-Ser).

Peptides are conjugated to antineoplastic agents so as to derive the compounds provided herein; said conjugation may be via either the amino or carboxy terminus of the peptide. "Conjugation," as used herein, means the linking of a peptide to a bioactive agent. Such linkage can be directly, through covalent bonding between the peptide and the agent, by means, and using reagents, well known to ordinarily skilled artisans. Covalent bonding between the peptide and agent includes the formation of an amide bond between a free amino group on the antineoplastic agent and the carboxyl group at the peptides C-terminus, or between the peptide's N-terminal amino group and a carboxyl group on the agent. Additionally, ester linkages can be formed between the C-terminal carboxyl group of the peptide and a free hydroxyl group on the antineoplastic agent or vice versa.

Alternatively, the peptide and antineoplastic agent can be conjugated indirectly through a linker group having free, active moities available for separate interactions with both the peptide and the agent. Such linkers include, for example, and without limitation, biscarbonyl alkyl diradicals, having a group available to form an amide bond with a free amino group on the antineoplastic agent as well as a second free group available to form an amide bond with the N-terminal amino group of the peptide. Suitable linker groups also include diaminoalkyl diradicals, having free amino groups available for amide bond formation with both the peptide's C-terminal carboxyl group and a free carboxyl group on the agent. Means of forming such amide, ester and other linkages between peptides and cytotoxic agents, either directly, or via linker groups, are well known to those of ordinary skill in the art.

Preferably, the antineoplastic agent used herein is doxorubicin and the enzyme cleavable peptide comprises an amino acid sequence recognized and cleaved by a matrixin, e.g., MMP-2, MMP-9, or MMP-14. More preferably, the peptide comprises the amino acid sequence PLGL (SEQ ID NO: 203), and can include the sequences PLGL (SEQ ID NO: 203), preferably as shown below

| PLGL | SEQ ID NO: 203 |
|---|---|
| PLGLL | SEQ ID NO: 212 |
| PLGLAL | SEQ ID NO: 213 |
| PLGLYL | SEQ ID NO: 214 |
| PLGLYAL | SEQ ID NO: 215 |
| PLGLAAL | SEQ ID NO: 216 |
| PLGLLSL | SEQ ID NO: 217 |
| PLGLLAL | SEQ ID NO: 218 |
| PLGLLYL | SEQ ID NO: 204 |
| GPLGL | SEQ ID NO: 205 |
| GPLGLL | SEQ ID NO: 219 |
| PLGHof | SEQ ID NO: 210 |
| PLG-(O-Benzyl)-S | SEQ ID NO: 220 |
| GPLGLAL | SEQ ID NO: 224 | and other sequences as exemplified in the Tables of Examples.

As used herein, "alkyl" or "alkylene" is intended to include both branched and straight-chain saturated aliphatic hydrocarbon groups having the specified number of carbon atoms; for example, "$C_1$–$C_6$ alkyl" denotes alkyl having 1 to 6 carbon atoms. Examples of alkyl include, collectively or individually, but are not limited to, methyl, ethyl, n-propyl, i-propyl, n-butyl, i-butyl, sec-butyl, t-butyl, n-pentyl, n-hexyl, 2-methylbutyl, 2-methylpentyl, 2-ethylbutyl, 3-methylpentyl, and 4-methylpentyl. Examples of $C_1$–$C_4$ alkyl include, collectively or individually, methyl, ethyl, n-propyl, i-propyl, n-butyl, i-butyl, sec-butyl, and t-butyl.

"Alkenyl" or "alkenylene" is intended to include hydrocarbon chains of either a straight or branched configuration having the specified number of carbon atoms and one or more unsaturated carbon—carbon bonds which may occur in any stable point along the chain. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, 4-methyl-3-pentenyl, and the like.

"Alkynyl" or "alkynylene" is intended to include hydrocarbon chains of either a straight or branched configuration and one or more carbon—carbon triple bonds which may occur in any stable point along the chain, such as ethynyl, propynyl, butynyl, pentynyl, hexynyl and the like.

"Cycloalkyl" is intended to include saturated ring groups, having the specified number of carbon atoms. For example, "$C_3$–$C_6$ cycloalkyl" denotes such as cyclopropyl, cyclobutyl, cyclopentyl, or cyclohexyl.

"Alkoxy" or "alkyloxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Similarly, "alkylthio" or "thioalkoxy" represents an alkyl group as defined above with the indicated number of carbon atoms attached through a sulpher bridge.

"Halo" or "halogen" as used herein refers to fluoro, chloro, bromo, and iodo; and "counterion" is used to represent a small, negatively charged species such as chloride, bromide, hydroxide, acetate, sulfate, and the like.

As used herein, "carbocycle" is intended to mean any stable 3- to 7-membered monocyclic or bicyclic or 7- to 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, or tetrahydronaphthyl (tetralin).

As used herein, the term "heterocycle" or "heterocyclic ring" is intended to mean a stable 5- to 7-membered monocyclic or bicyclic or 7- to 14-membered bicyclic heterocyclic ring which is saturated partially unsaturated or unsaturated (aromatic), and which consists of carbon atoms and 1, 2, 3 or 4 heteroatoms independently selected from the group consisting of N, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1.

Examples of heterocycles include, but are not limited to, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazalonyl, carbazolyl, 4aH-carbazolyl, b-carbolinyl, chromanyl, chromenyl, cinnolinyl, decahydroquinolinyl, 2H, 6H-1,5,2-dithiazinyl, dihydrofuro [2,3-b]tetrahydrofuran, furanyl, furazanyl, imidazolidinyl, imidazolinyl, imidazolyl, imidazolopyridinyl, 1H-indazolyl, indolenyl, indolinyl, indolizinyl, indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolopyridinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thiazolopyridinyl, thienyl, thienothiazolyl, thienooxazolyl, thienoimidazolyl, thiophenyl, triazinyl, 1,2,3-triazolyl, 1,2, 4-triazolyl, 1,2,5-triazolyl, 1,3,4-triazolyl, and xanthenyl. Preferred heterocycles include, but are not limited to, pyridinyl, furanyl, thienyl, pyrrolyl, pyrazolyl, pyrazinyl, piperazinyl, imidazolyl, indolyl, benzimidazolyl, 1H-indazolyl, oxazolidinyl, benzotriazolyl, benzisoxazolyl, benzoxazolyl, oxindolyl, benzoxazolinyl, benzthiazolyl, benzisothiazolyl, isatinoyl, isoxazolopyridinyl, isothiazolopyridinyl, thiazolopyridinyl, oxazolopyridinyl, imidazolopyridinyl, and pyrazolopyridinyl. Preferred 5 to 6 membered heterocycles include, but are not limited to, pyridinyl, furanyl, thienyl, pyrrolyl, pyrazolyl, pyrazinyl, piperazinyl, imidazolyl, and oxazolidinyl. Also included are fused ring and spiro compounds containing, for example, the above heterocycles.

As used herein, the term "aryl", or aromatic residue, is intended to mean an aromatic moiety containing the specified number of carbon atoms, such as phenyl and naphthyl.

Also provided herein are pharmaceutical composition comprising compounds provided herein and a pharmaceutically acceptable carrier. Such carriers are media generally accepted in the art for the delivery of biologically active agents to animals, in particular, mammals. Pharmaceutically acceptable carriers are generally formulated according to a number of factors well within the purview of those of ordinary skill in the art to determine and account for. These include, without limitation: the type and nature of the active agent being formulated; the subject to which the agent-containing composition is to be administered; the intended route of administration of the composition; and, the therapeutic indication being targeted.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, well known to those of ordinary skill in the art. Descriptions of suitable pharmaceutically acceptable carriers, and factors involved in their selection, are found in a variety of readily available sources, e.g., *Remington's Pharmaceutical Sciences,* 17th ed., Mack Publishing Company, Easton, Pa., 1985, the contents of which are incorporated herein by reference.

Compounds of this invention are administered, for example, parenterally in various aqueous media such as aqueous dextrose and saline solutions; glycol solutions are also useful carriers. Solutions for parenteral administration preferably contain a water soluble salt of the active ingredient, suitable stabilizing agents, and if necessary, buffer substances. Antioxidizing agents, such as sodium bisulfite, sodium sulfite, or ascorbic acid, either alone or in combination, are suitable stabilizing agents. Also used are citric acid and its salts, and EDTA. In addition, parenteral solutions can contain preservatives such as benzalkonium chloride, methyl- or propyl-paraben, and chlorobutanol.

Alternatively, the compounds are administered orally in solid dosage forms, such as capsules, tablets and powders; or in liquid forms such as elixirs, syrups, and/or suspensions. Gelatin capsules can be used to contain the active ingredient and a suitable carrier such as but not limited to lactose, starch, magnesium stearate, stearic acid, or cellulose derivatives. Similar diluents can be used to make compressed tablets. Both tablets and capsules can be manufactured as sustained release products to provide for continuous release of medication over a period of time. Compressed tablets can be sugar-coated or film-coated to mask any unpleasant taste, or used to protect the active ingredients from the atmosphere, or to allow selective disintegration of the tablet in the gastrointestinal tract.

Further provided herein is a method of delivering compound of this invention to the cells of a mammal in need of antineoplastic treatment, said method comprising contacting the cells with therapeutically effective amounts of the compounds in the presence of the corresponding peptidase. "Therapeutically effective amounts" are any amounts of a compound effective to ameliorate, alleviate, lessen or inhibit the symptoms, progression thereof, or the underlying manifestations of a particular disease, disorder or condition; typically, for in vivo treatment, therapeutically effective amounts are from about 0.1 mg of a compound per kg of body weight of the mammal being treated, to about 1000 mg/kg. Said mammals may be suffering from breast, ovarian, brain, stomach, lung, colon, prostate or liver cancers, or leukemias, lymphomas, carcinomas, sarcomas, or melanomas, as well as other forms of cancers.

The conjugated compounds of the present invention are useful as chemotherapeutic agents in the targeted treatment of cancers. For example, in the treatment of cancers, peptides and antineoplastic agents are conjugated to produce stable conjugates which can be administered to mammals and circulate in the blood stream stable to nonspecific enzymatic degradation, for example neprolysin. Conjugation also reduces the antineoplastic agent's ability to exert its effects on tissue, i.e., healthy, nontarget tissue; such that the agent's toxicity is greatly reduced in comparison to use in its unconjugated, free form. However, once the peptide is cleaved from the antineoplastic agent by one or a combination of membrane-bound and/or cell-secreted peptidases, the agent is released such that it can then exert its desired therapeutic effect on cells in the surrounding area. While multiple peptidases may be involved in removing or processing of the amino acids from the antineoplastic agent, an initiating peptidase cleavage event is required to activate these conjugates. Peptidases, such as the matrixins MMP-2 and MMP-9 and MMP-14, are found in the tumor environment. Hence, conjugation of a matrixin or MMP enzyme-cleavable peptide to an antineoplastic agent offers a novel means of delivering the agent as a therapeutic entity specifically to tumors while reducing the agent's toxicity on healthy, nontarget tissue. However, the conjugate is also designed so that the product of the first proteolytic event is an acceptable substrate for aminopeptidases expressed in the tumor tissue which further remove or process remaining amino acids from the antineoplastic agent. It is known that such aminopeptidases, e.g., dipeptidyl aminopeptidase and neutral aminopeptidase, are expressed in tumor tissue (Pasqualini). Thus, the compounds of the present invention, upon first proteolytic cleavage by a matrix metalloproteinase, are not intended to produce unconjugated Dox.

Peptide/antineoplastic agent conjugates of the present invention are stable in plasma, such stability being demonstrated by a number of means well known in the art, e.g., by incubation in various media (see, e.g., Example 6 hereinbelow). Hence, the conjugates of the present invention can be effectively used as therapeutic entities for administration to mammals. Matrixins and aminopeptidases, are known to be produced in neoplastic cells, and to be found in the cells, or in their vicinity. Endothelial and stromal cells, which may be found in proximity to the tumor, may also contain peptidase activities that contribute to the delivery of therapeutic entities to the tumor. Such matrixins and aminopeptidases, as described hereinabove, are have been shown to recognize and cleave enzyme-cleavable peptides conjugated to cytotoxic agents herein (see Example 7, hereinbelow), releasing the peptide, in a complete or truncated form, and the agent, with or without amino acids attached. Cleavage releases the cytotoxic antineoplastic agent from the conjugate such that it can then exert its beneficial therapeutic effect on neoplastic cells. Accordingly, conjugation of a matrixin or MMP enzyme-cleavable peptide to a cytotoxic agent affords targeted delivery of the agent as a therapeutic entity specifically to tumors, while minimizing the adverse impact of the agent on healthy, nontarget tissue.

Following is the bibliographic information for the documents cited hereinabove. Ames, R. and Quigley, J., *J. Biol. Chem.* 270:5872–5876 (1995); Baurain, R., et al., *J. Med. Chem.* 23:1170–1174 (1980); Boven, E., et al., *Eur. J. Cancer* 26:983–986 (1990); Boven, E., et al., Br. *J. Cancer* 66:1044–1047 (1992); Brooks, P., et al., *Cell* 85:683–693 (1996); Brummer, O., et al., *Virchows Arch.* 435:566–573 (1999); Canal, P., et al., *Clin. Pharmacol. Therp.* 51:249–259 (1992); de Groot, F. M. H. et al., *J. Med. Chem.* 43:3093–3102 (2000); Denmeade, et al., *Cancer Res.* 58:2537–2540 (1998); de Jong, J., et al., *Cancer Chemother Pharmacol.* 31:156–160 (1992a); de Jong, J., et al., *J. Clin. Oncology* 10:1897–1906 (1992b); Garbisa, S., et al., *Cancer Res.*, 53:4548–4549 (1992); Kandukuri, S. P. et al., *J. Med. Chem.* 28:1079–1088 (1985); Knauper, V., et al., *J. Biol. Chem.* 271:1544–1550(1996); Kurschatt, P., et al., *J. Biol. Chem.* 274:21056–21062 (1999); Li, C. et al., *J. Biol. Chem,* 270:5723–5728(1995); Lu, J. Y. et al., *J. Drug Targeting* 7(1)$_{43}$–53 (1999); Liotta, L., et al., *Cell* 64:327–336 (1991); MacDougall, J. and Matrisian, L., *Cancer and Metastasis Reviews* 14:351–362 (1995); Masquelier, M., et al., *J. Med. Chem.* 23:1166–1170 (1980); McDonnell, S. and Fingleton, B., *Cytotechnology* 12:367–384 (1993); McGeehan, G., et al., *J. Biol. Chem.* 269:32814–32820 (1994)); Nagase, H., et al., *Biopolymers* 40:399416 (1996); Moses, M., et al., *Cancer Res.* 58:1395–1399 (1998)); Nakajima, K., et al., *J. Biol. Chem.* 254:4027–4032 (1979); Odake, S., et al., *Biochemistry* 30:2217–2227 (1991); R. Pasqualini, *Cancer Research* 60:722–727 (2000); A. Safavy et al. (*J. Med. Chem.* 42:4919–4924 (1999); Sato, J., et al., *Nature* 370:61–65 (1994); Trouet and Baurain, U.S. Pat. No. 5,962,216 (issued Oct. 5, 1999); Soini, Y. et al., *J. Histochem. Cytochem.* 42:945–951(1994); Sundfor, K. et al., Br. *J. Chem.* 78:822 (1998); von Hoff, D., et al., *Ann. Intern. Med.* 91:710–717 (1979) Yu, Q. and Stamenkovic, I., *Genes and Dev.* 13:35–48 (1999). Rhusolahti, Cancer Research In another embodiment, the invention describes a method of treating cancer in a patient in need thereof, comprising administering to said patient a pharmaceutically effective amount of a compound as set forth above, or a pharmaceutically acceptable salt form thereof, wherein the cancer is selected from the group consisting of: carcinoma such as bladder, breast, colon, kidney, liver, lung, including small cell lung cancer, esophagus, gall-bladder, ovary, pancreas, stomach, cervix, thyroid, prostate, and skin, including squamous cell carcinoma; hematopoietic tumors of lymphoid lineage, including leukemia, acute lymphocytic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma; hematopoietic tumors of myeloid lineage, including acute and chronic myelogenous leukemias, myelodysplastic syndrome and promyelocytic leukemia; tumors of mesenchymal origin, including fibrosarcoma and rhabdomyosarcoma; tumors of the central and peripheral nervous system, including astrocytoma, neuroblastoma, glioma and schwannomas; other tumors, including melanoma, seminoma, teratocarcinoma, osteosarcoma, xenoderoma pigmentosum, keratoctanthoma, thyroid follicular cancer and Kaposi's sarcoma.

In another embodiment, the invention describes a method of treating cancer in a patient in need thereof, comprising administering to said patient a pharmaceutically effective amount of a compound of Formula (I) or (Ia) as set forth above, or a pharmaceutically acceptable salt form thereof, in combination (administered together or sequentially) with known anti-cancer treatments such as radiation therapy or with cytostatic or cytotoxic agents, wherein such agents are selected from the group consisting of: DNA interactive agents, such as cisplatin or doxorubicin; topoisomerase II inhibitors, such as etoposide; topoisomerase I inhibitors such as CPT-11 or topotecan; tubulin interacting agents, such as paclitaxel, docetaxel or the epothilones; hormonal agents, such as tamoxifen; thymidilate synthase inhibitors, such as 5-fluorouracil; and anti-metabolites, such as methoxtrexate.

In another embodiment, the invention describes a method treating cancer in a patient in need thereof, comprising administering to said patient a pharmaceutically effective amount of a compound of Formula (I) or (Ia) as set forth above, or a pharmaceutically acceptable salt form thereof, in combination (administered together or sequentially) with known anti-proliferating agents selected from the group consisting of:, altretamine, busulfan, chlorambucil, cyclophosphamide, ifosfamide, mechlorethamine, melphalan, thiotepa, cladribine, fluorouracil, floxuridine, gemcitabine, thioguanine, pentostatin, methotrexate, 6-mercaptopurine, cytarabine, carmustine, lomustine, streptozotocin, carboplatin, cisplatin, oxaliplatin, iproplatin, tetraplatin, lobaplatin, JM216, JM335, fludarabine, aminoglutethimide, flutamide, goserelin, leuprolide, megestrol acetate, cyproterone acetate, tamoxifen, anastrozole, bicalutamide, dexamethasone, diethylstilbestrol, prednisone, bleomycin, dactinomycin, daunorubicin, doxirubicin, idarubicin, mitoxantrone, losoxantrone, mitomycin-c, plicamycin, paclitaxel, docetaxel, CPI-11, cpothilones, topotecan, irinotecan, 9-amino camptothecan, 9-nitro camptothecan, GS-211, etoposide, teniposide, vinblastine, vincristine, vinorelbine, procarbazine, asparaginase, pegaspargase, methoxtrexate, octreotide, estramustine, and hydroxyurea.

As used herein the term "effective amount" means an amount of a compound/composition according to the present invention effective in producing the desired therapeutic effect.

As used herein the term "treating" refers to: (i) preventing a disease, disorder or condition from occurring in an animal which may be predisposed to the disease, disorder and/or condition but has not yet been diagnosed as having it; (ii) inhibiting the disease, disorder or condition, i.e., arresting its development; and (iii) relieving the disease, disorder or condition, i.e., causing regression of the disease, disorder and/or condition.

As used herein the term "patient" includes both human and other mammals.

As used herein the term "pharmaceutical composition" means a composition comprising a compound of Formula (I) or (Ia) and at least one component selected from the group comprising pharmaceutically acceptable carriers, diluents, adjuvants, excipients, or vehicles, such as preserving agents, fillers, disintegrating agents, wetting agents, emulsifying agents, suspending agents, sweetening agents, flavoring agents, per-fuming agents, antibacterial agents, antifungal agents, lubricating agents and dispensing agents, depending on the nature of the mode of administration and dosage forms. Examples of suspending agents include ethoxylated isostearyl alcohols, polyoxyethylene sorbitol and sorbitan esters, microcrystalline cellulose, aluminum metahydroxide, bentonite, agar—agar and tragacanth, or mixtures of these substances. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride and the like. Prolonged absorption of the injectable pharmaceutical form can be brought about by the use of agents delaying absorption, for example, aluminum monosterate and gelatin. Examples of suitable carriers, diluents, solvents or vehicles include water, ethanol, polyols, suitable mixtures thereof, vegetable oils (such as olive oil) and injectable organic esters such as ethyl oleate. Examples of excipients include lactose, milk sugar, sodium citrate, calcium carbonate, dicalcium phosphate phosphate. Examples of disintegrating agents include starch, alginic acids and certain complex silicates. Examples of lubricants include magnesium stearate, sodium lauryl sulphate, talc, as well as high molecular weight polyethylene glycols.

This invention will be better understood when read in light of the following Examples. However, those of ordinary skill in the art will readily understand that the examples are merely illustrative of the invention as defined in the claims which follow thereafter.

EXAMPLES

Conjugation of Peptides to Antineoplastic Compounds

Example 00

Synthesis of Ac-PLGL-Dox (SEQ ID NO: 237)

The peptide acid was synthesized on the solid phase from commercially available Fmoc-Leu-Wang resin (0.40 g, 0.6 mmol). The synthesis was performed on an ABI 433A peptide synthesizer using four equivalents of Fmoc protected amino acids and HBTU activation. The peptide resin was acetylated with acetic anhydride. The peptide was cleaved from the resin with 90% TFA in water for 2h. After solvent removal the peptide was dissolved in $H_2O$: $CH_3CN$ and freeze-dried. Product was confirmed by ES MS 496.3 (M–H). Analytical HPLC on a Metachem Monochrom C18 reverse phase column (50×4.6 mm) showed crude peptide to be 85% pure. To this intermediate (0.0199 g, 0.04 mmol) dissolved in DMF (0.2 mL) in a small amber vial was added Pybop (0.0208 g, 0.04 mmol). Doxorubicin hydrochloride (0.0186 g, 0.032 mmol) was added as a suspension in DMF (0.1 mL) followed by diisopropylethylamine (DIEA) (0.0139 mL, 0.08 mmol). The reaction was stirred for 2 h. Solvent was removed under vacuum. Sample was dissolved in $H_2O$: $CH_3CN$ and purified using a Dynamax C18 reverse phase column (41.4×250 mm) with a linear gradient from 30–50% acetonitrile, 0.05% ammonium acetate over 20 minutes with a flow rate of 45 mL/minute. Fractions were pooled and freeze dried to afford the purified peptide-Dox conjugate (ES MS 964.6 (M–H)).

Solid Phase Synthesis of Doxorubicin Conjugates

Example 47

Synthesis of Ac-PLGLYL-Dox (SEQ ID NO: 47).

The peptide acid was synthesized on the solid phase from commercially available Fmoc-leu-Wang resin (0.42 g, 0.25 mmol). The synthesis was performed on an ABI 433A peptide synthesizer using four equivalents of Fmoc protected amino acids and HBTU activation. The peptide resin was acetylated with acetic anhydride. The peptide was cleaved from the resin with 90% TFA in water for 2h. After solvent removal the peptide was dissolved in $H_2O$: $CH_3CN$ and freeze-dried. Product was confirmed by ES MS 717.4 (M+H). Analytical HPLC on a Metachem Monochrom C18 reverse phase column (50×4.6 mm) showed crude peptide to be 80% pure. To this intermediate (0.0286 g, 0.04 mmol) dissolved in DMF (0.2 mL) in a small amber vial was added PyBop (0.0208 g, 0.04 mmol). Doxorubicin hydrochloride (0.0186 g, 0.032 mmol) was added as a suspension in DMF (0.1 mL) followed by diisopropylethylamine (DIEA) (0.0139 mL, 0.08 mmol). The reaction was stirred for 2 h. Solvent was removed under vacuum. Sample was dissolved in $H_2O$: $CH_3CN$ and purified using a Dynamax C18 reverse phase column (41.4×250 mm) with a linear gradient from 35–55% acetonitrile, 0.05% ammonium acetate over 20 minutes with a flow rate of 45 mL/minute. Fractions were pooled and freeze dried to afford the purified peptide-Dox conjugate (ES MS 1240.7 (M–H)).

Example 116

Synthesis Of Ac-PLG-Hof-Orn-L-Dox (SEQ ID NO: 116).

The peptide acid (Ac-PLG-Hof-Orn(allyl)-L-COOH) was synthesized on the solid phase from commercially available Fmoc-Leu-Wang resin (0.28 g, 0.25 mmol). The synthesis was performed on an ABI 433A peptide synthesizer using four equivalents of Fmoc protected amino acids and HBTU activation. The peptide resin was acetylated with acetic anhydride. The peptide was cleaved from the resin with 90% TFA in water for 2h.

After solvent removal the peptide was dissolved in H$_2$O: CH$_3$CN and freeze dried.

Product was confirmed by ES MS 800.7 (M+H)$^+$, 822.7 (M+Na)$^+$. Analytical HPLC on a Metachem Monochrom C18 reverse phase column (50×4.6 mm) showed crude peptide to be 90% pure. To this intermediate (0.320 g, 0.4 mmol) dissolved in DMF (2.0 mL) in a small amber vial was added PyBop (0.204 g, 0.4 mmol). Doxorubicin hydrochloride (0.148 g, 0.26 mmol) was added as a suspension in DMF (1.0 mL) followed by diisopropylethylamine (DIEA) (0.28 mL, 1.6 mmol). The reaction was stirred for 2.5 h. Solvent was removed under vacuum. Sample was dissolved in H$_2$O: CH$_3$CN and purified using a Phenomenex LUNA C18 reverse phase column (250×21.2 mm) with a linear gradient from 45–55% acetonitrile, 0.05% ammonium acetate over 30 minutes with a flow rate of 18 mL/minute. Fractions were pooled and freeze dried to afford the purified Ac-PLG-Hof-Orn(allyl)-L-Dox (SEQ ID NO: 116). (ES MS 1325.4 (M+H)$^+$, 911.4 (M+H-414)$^+$). Side chain protected peptide (0.076 g, 0.06 mmol) was dissolved in dry DCM (7 mL) under Ar$_2$. [(Ph$_3$)P]$_4$Pd (0.014 g, 0.012 mmol) in DCM (1 mL) was added followed by morpholine (0.052 mL, 0.6 mmol). The reaction was stirred at rt for 2h and monitored by HPLC. Product was precipitated from EtOAc and washed with EtOAc (2×). Solvent was removed with a N$_2$ flow. Unprotected conjugate (Ac-PLG-Hof-OrnL-Dox) (SEQ ID NO: 116) was purified using a Phenomenex LUNA C18 reverse phase column (250×21.2 mm) with a linear gradient from 2540% acetonitrile, 0.05% ammonium acetate over 30 minutes with a flow rate of 18 mL/minute. Fractions were pooled and freeze dried to afford the purified product (95% pure) (ES MS 1241.9 (M+H)$^+$, 827.7 (M+H-414)$^+$).

Alternate Solid Phase Synthesis Of Doxorubicin Conjugates

Example 11

Synthesis Of Acp-PLGLL-Dox (SEQ ID NO: 11).

Acp=4-(2-aminoethyl)-1-carboxymethyl piperazine. The Fmoc protected peptide acid (Fmoc-Acp-PLGLL-COOH) (SEQ ID NO: 240) was synthesized on the solid phase from commercially available Fmoc-Leu-Wang resin (1.6 g, 1.0 mmol). The synthesis of PLGLL-resin (SEQ ID NO: 212) was performed on an ABI 433A peptide synthesizer using three equivalents of Fmoc protected amino acids and HBTU activation. A portion of the peptide resin (0.18 g, 0.1 mmol) was then coupled to Fmoc-Acp dihydrochloride (0.193 g, 0.4 mmol) with HBTU (0.152 g, 0.4 mmol) and DIEA (0.143 mL, 0.8 mmol) in DMF (2 mL) for 2 h. The peptide was cleaved from the resin with 90% TFA in water for 2h. After solvent removal the peptide was dissolved in H$_2$O: CH$_3$CN and freeze dried. To this intermediate (0.036 g, 0.04 mmol) dissolved in DMF (0.2 mL) in a small amber vial was added PyBop (0.021 g, 0.04 mmol). Doxorubicin hydrochloride (0.018 g, 0.032 mmol) was added as a suspension in DMF (0.11 nL) followed by diisopropylethylamine (DIEA) (0.014 mL, 0.08 mmol). The reaction was stirred for 2 h. Solvent was removed under vacuum. Sample was dissolved in H$_2$O: CH$_3$CN and purified using a Phenomenex LUNA C18 reverse phase column (250×21.2 mm) with a linear gradient from 20–50% acetonitrile, 0.05% ammonium acetate over 30 minutes with a flow rate of 18 mL/minute. Fractions were pooled and freeze dried to afford the Fmoc-Acp-PLGLL-Dox (SEQ ID NO: 240) (ES MS 1428.9 (M+H)$^+$, 1014.7 (M+414)$^+$). Fmoc protected peptide (0.020 g, 0.014 mmol) was dissolved in a cold solution of 50% diethylamine in DCM (6 mL).

The reaction was stirred protected from light at 0° for 3h. The solvent was removed under vacuum. DCM was added to redissolve the sample and was removed under vacuum 4×.

The sample was dried further with a flow of N$_2$. The sample was then washed with Hex:Et$_2$O, 1:1 5X followed by evaporation under vacuum and a final flow of N$_2$. Sample was dissolved in acetate buffer: CH$_3$CN and purified using a Phenomenex LUNA C18 reverse phase column (250×21.2 mm) with a linear gradient from 15–50% acetonitrile, 0.05% ammonium acetate over 35 minutes with a flow rate of 18 mL/minute. Fractions were pooled and freeze dried to afford the purified (90% pure) Acp-PLGLL-Dox (SEQ ID NO: 11) (ES MS 1207 (M+H)$^+$, 793 (M+H-414)$^+$).

For examples of this invention where unusual amino acids are coupled to the chemotherapeutic agent, for example doxorubicin, the requisite solid support is frequently not commercially available. The following example illustrates how the modified support is prepared in these cases.

Example 182

Synthesis Of Ac-PLG-Hof-Y-Hol-Dox (SEQ ID NO: 182).

Coupling of unnatural amino acids to solid support.

Triphenyl phosphine (4.78 g, 18.25 mmol) was dissolved in DMF (100 mL) and the solution was cooled to 0° C. Wang resin (5.2 g, 4.45 mmol) was added, the reaction was stirred for 10 minutes followed by addition of carbon tetrabromide (6.06 g, 18.25 mmol). The reaction was stirred for 5 h. The resin was washed and dried. A portion of the resin (0.281 g, 0.25 mmol) was swelled in DMF (2.5 mL), Fmoc-Hol (0.138 g, 0.375 mmol) was added, followed by DIEA (0.065 mL, 0.375 mmol) and Cesium iodide (0.065 g, 0.25 mmol). The reaction was rocked overnight. The resin was washed and completion of reaction was corroborated by ninhydrin test. The resin was then transferred to the peptide synthesizer for subsequent couplings. Coupling to Doxorubicin was done as in Example 47. Ac-PLG-Hof-Y-Hol-Dox (SEQ ID NO: 182). (ES MS 1326.3 (M+Na)$^+$, 890.4 (M+H-414)$^+$).

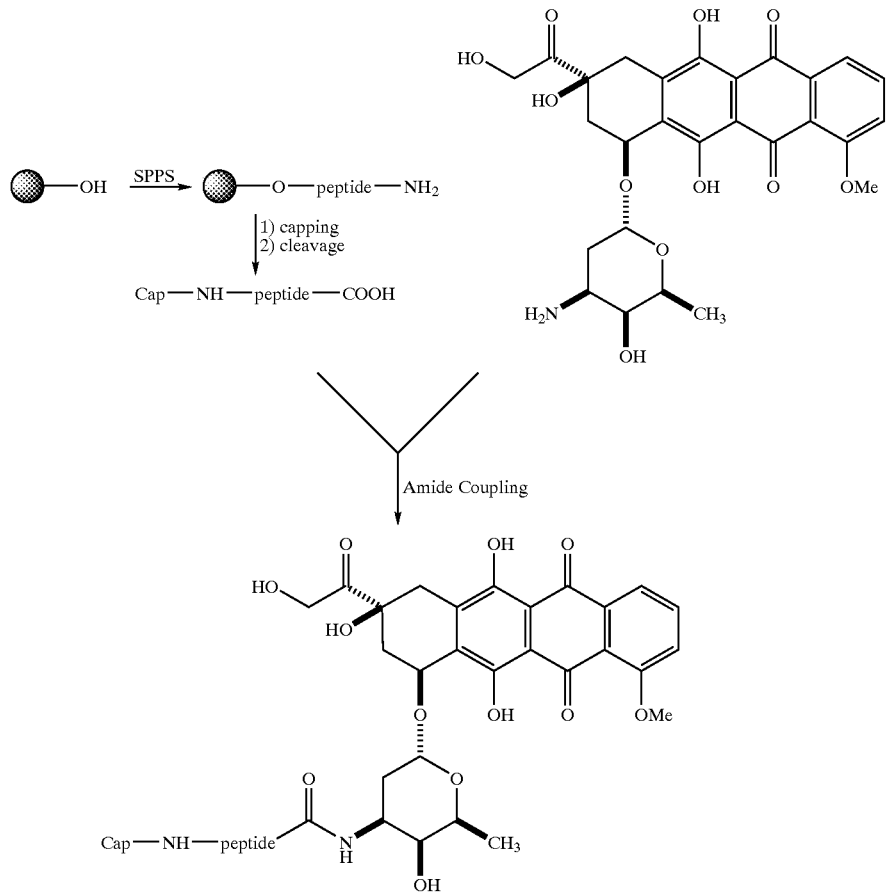

Scheme 1
Solid Phase Synthesis of Doxorubicin Conjugates

Solution Phase Synthesis of Conjugates

Example 104

Synthesis Of Ac-Pro-Leu-Gly-Hof-Gly (morpholinylpropyl)Leu-Dox (SEQ ID NO: 104). (Scheme 2)

(Step 1a): To a mixture of Z-Leu-OH (2.65 g, 10 mmol), H-Gly-OtBu hydrochloride (1.7 g, 10 mmol) and EDCI (2.3 g, 12 mmol) in 200 mL CH$_2$Cl$_2$ was added diisopropylethylamine (3.0 mL) slowly at 0° C. The resulted mixture was stirred at this temperature for 30 min and at room temperature for 2 hrs. Then, the reaction mixture was diluted with CH$_2$Cl$_2$, washed with 1N HCl solution, Sat. NaHCO$_3$, water and brine, and dried over MgSO$_4$. After filtration and concentration, the desired dipeptide Z-Leu-Gly-OtBu was obtained as white solid (3.75 g, >95%). MS found (M+1)+ 379.2.

(Step 1b): The dipeptide obtained from (Step 1a) (3.75 g, 10 mmol) was dissolved in methanol (200 mL), and the mixture was hydrogenated in the presence of catalytic amount of Pd/C (0.1 mol %) and a few drops of 4N HCl in dioxane at 1 atm for 3 hrs. The reaction mixture was filtered, concentrated and dried.

The amine obtained above was dissolved in CH$_2$Cl$_2$ (500 mL), and to this mixture were added Ac-Pro-OH (1.57 g, 10 mmol), EDCI (2.3 g, 12 mmol), catalytic amount of HOBT (100 mg), and diisopropylethylamine (4.0 mL). The mixture was stirred at room temperature for 3.5 hrs. Then, the reaction mixture was diluted with CH$_2$Cl$_2$, washed with 1N HCl solution, Sat. NaHCO$_3$, water and brine, and dried over MgSO$_4$. Chromatography on silica gel (20% EtOAc in hexane) yielded the desired tripeptide Ac-Pro-Leu-Gly-OtBu as white solid(3.63 g, 95%). MS found (M+1)+384.3.

(Step 1c): The tripeptide obtained from (Step 1b) (3.63 g, 9.5 mmol) was dissolved in CH$_2$Cl$_2$ (100 nL), and TFA (100 mL) was added slowly at 0° C. The mixture was stirred at 0° C. for 15 min. and room temperature for 2 hrs. Evaporation of solvent provided the desired acid Ac-Pro-Leu-Gly-OH as white solid (3.08 g, >95%). MS found (M+1)+328.2.

(Step 2a): A mixture of Z-Glu-OtBu (3.0 g, 8.9 mmol), morpholine (2.0 mL, 23 mmol), EDCI (2.22 g, 11.6 mmol),), catalytic amount of HOBT (50 mg), and diisopropylethylamine (2.0 mL) in THF (60 mL) was stirred at room temperature for 3 hrs. Most of the solvent was removed, the residue was dissolved in EtOAc (100 mL) and washed with 1N HCl solution, Sat. NaHCO$_3$, water, brine, and dried over MgSO$_4$.

Evaporation of solvent provided the desired compound as white solid (3.6 g, >95%). MS found (M+1)+407.2.

(Step 2b): The material from (Step 2a) (3.5 g, 8.62 mmol) was dissolved in THF (50 mL). To this mixture was added BH$_3$ THF (1.0 M, 10 mL) and the resulted mixture was stirred at reflux for 1.5 hr and room temperature for 30 min.

Solvent was removed, the residue was dissolved in EtOAc (100 mL) and washed with Sat. NaHCO₃, water, brine. Chromatography on silica gel (60% EtOAc in hexane) yielded the desired Z-Gly(morpholinylpropyl)-OtBu as white solid (2.7 g, 81%). MS found (M+1)+393.1.

(Step 2c): Following a procedure analogous to (Step 1c) (2.7 g, 6.89 mmol), the material from (Step 2b) was treated with TFA to give acid Z-Gly(morpholinylpropyl)-OH as white solid (2.3 g, >95%). MS found (M−1)⁻ 335.1.

(Step 2d): The material obtained from (Step 2c) (392 mg, 1.0 mmol) was dissolved in DMF (10 mL). To this mixture were added H-Leu-OMe hydrochloride salt (182 mg, 1.0 mmol), BOP (442 mg, 1.0 mmol) and DIEA (0.52 mL, 3.0 mmol). The resulted mixture was stirred at room temperature for 2 hrs. Most of the solvent was removed, and the residue was diluted with EtOAc (80 mL), washed with 1N HCl solution, Sat. NaHCO₃, water, brine, and dried over MgSO₄. After HPLC purification (CNCH₃/H₂O), the desired dipeptide Z-Gly(morpholinylpropyl)-Leu-OMe was obtained as white solid (393 mg, 85%). MS found (M+1)+ 464.6.

(Step 2e): The dipeptide obtained from (Step 2d) (393 mg, 0.85 mmol) was dissolved in methanol (100 mL), and the mixture was hydrogenated in the present of catalytic amount of Pd/C (0.1 mol %) and a few drops of 4N HCl in dioxane at 1 atm for 3 hrs. The reaction mixture was filtered, concentrated and dried.

Following a procedure analogous to (Step 2d), the material from above was coupled with Boc-Hof-OH to give desired tripeptide Boc-Hof-Gly(morpholinylpropyl)-Leu-OMe as white solid (381 mg, 76%). MS found (M+1)+ 591.4.

(Step 2f): Following a procedure analogous to (Step 1c), the material obtained from (Step 2e) (381 mg, 0.65 mmol) was treated with TFA to provide the corresponding amine. MS found (M+1)+491.4.

Following a procedure analogous to (Step 2d), the material from above was coupled with tripeptide Ac-Pro-Leu-Gly-OH to give the desired hexapeptide Ac-Pro Leu-Gly-Hof-Gly(morpholinylpropyl)-Leu-Ome (SEQ ID NO: 104) as white solid (437 mg, 84%). MS found (M+1)⁺ 800.5.

(Step 2g): To a solution of the material (400 mg, 0.5 mmol) obtained from (Step 2f) in THF (5 mL) at 0° C. was added IN LiOH solution (5 mL). After stirring at this temperature for 3 hrs, the reaction mixture was acidified with 1N HCl (5 mL) to pH 5. Solvent was removed and the mixture was purified by HPLC (CNCH3/H₂O). The desired hexapeptide was obtained as white solid (337 mg, 86%). MS found (M−1) 784.5.

(Step 2h): To a solution of the material obtained from (Step 2g) (39 mg, 0.05 mmol) in DMF (5 mL) at 0° C. were added BOP (27 mg, 0.06 mmol) and DIEA (0.05 mL). After stirring at this temperature for 5 min., doxorubicin hydrochloride (30 mg, 0.05 mmol) was added to the above mixture. The resulted mixture was stirred in dark at 0° C. for 1 hr and at room temperature for 2 hrs. Most of the solvent was removed and the residue was purified by HPLC [CH₃CN (0.1% NH₄Ac)/IH₂O(0.1% NH₄Ac)]. MS found (M−1) 1309.1. (Note: There are two HPLC peaks with the desired mass. These may be the two diastereomers caused by racemization during the coupling).

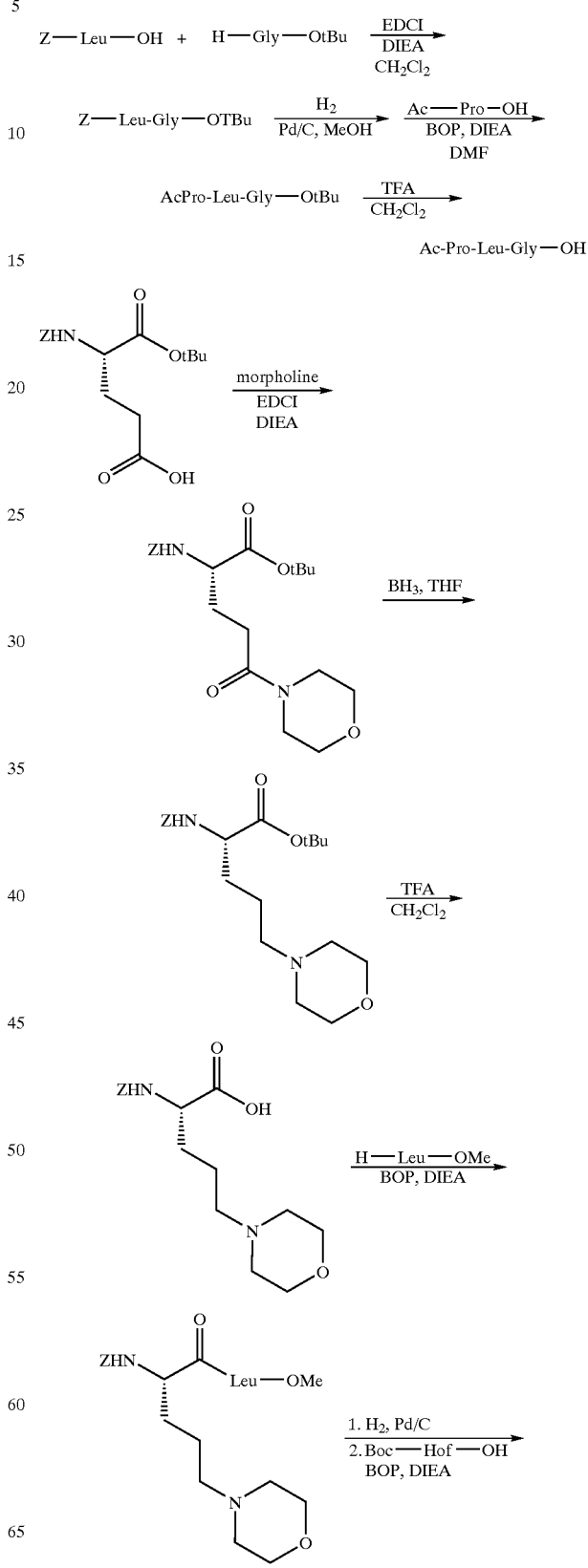

Scheme 2
Solution Phase Synthesis of a
Representative Doxorubicin Conjugate

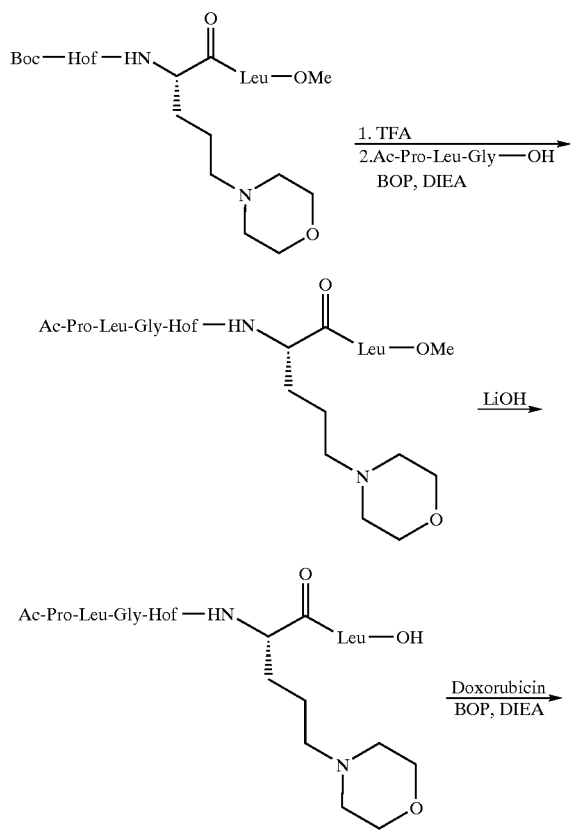

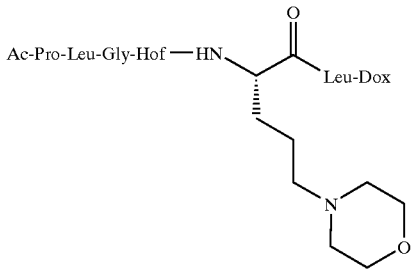

Synthetic methodology is known in the literature for the selective acylation of the important chemotherapeutic agent paclitaxel. For example, L-alanine has been introduced onto the 2' hydroxyl of paclitaxel (Sundfor, 1998). Should ester prove to have suboptimal stability properties, it is known in the art that a carbamate-based linker strategy will generate more stable conjugates (de Groot This methodology has previously been used to deliver paclitaxel to tumors using plasmin; however, appropriate engineering of the peptide sequence as disclosed in this invention should generate conjugates that are cleavable by MMPs.

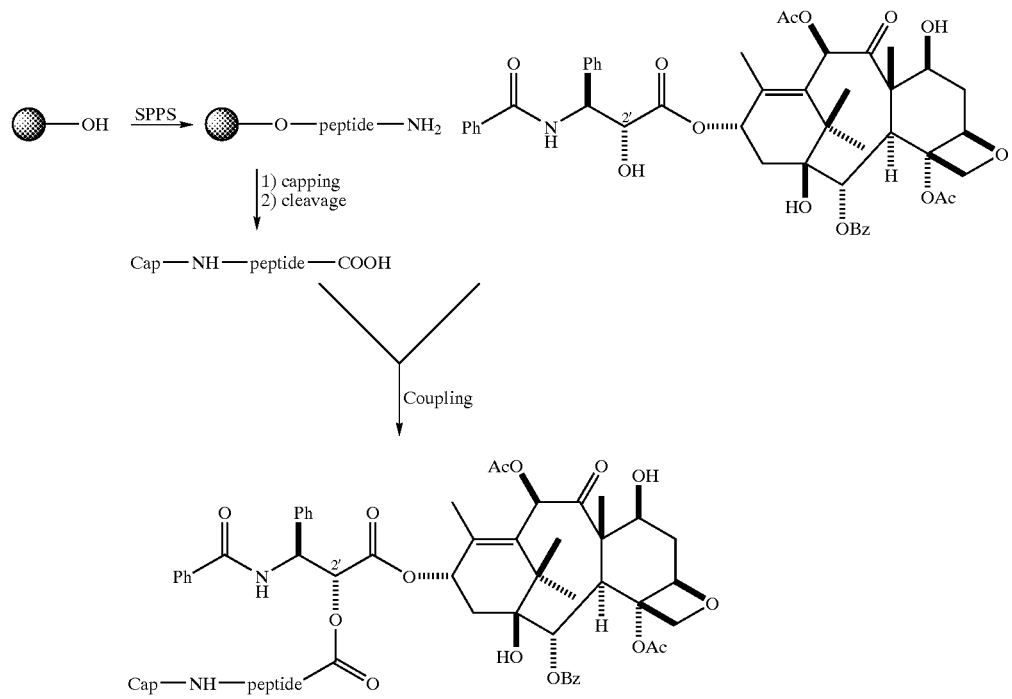

Scheme 3
Synthesis of Paclitaxel Conjugates

It has been shown in the literature that peptides may be attached to Vinca alkaloids, such as vinblastine and vincristine. For example, the carbomethoxy group of vinblastine may be selectively activated and attached to the N-terminus of a peptide chain (Kandukuri). A skilled artisan could combine this technology with the peptide sequences of this invention to generate MMP cleavable vinca alokaloid conjugates.

Example 1000

Evaluation of Stability of Conjugates in Blood

The stability of doxorubicin conjugated peptides in human or nude mouse blood was evaluated by reverse phase HPLC with fluorescence detection after an 80% acetonitrile extraction. Individual peptides are prepared as 60 μmolar solutions in Hepes buffer pH 7.5 (50 mM), with CaCl$_2$ (10 mM), Brij-35 (0.1%), followed by dilution to 10 μmolar in fresh heparinized whole blood or buffer. Solutions are incubated (37° C.) with slow continuous rocking. 50 μl reactions are terminated at designated times ranging from 1 minute to 24 hours by vortexing into 200 μl acetonitrile. After a brief centrifugation (1 min, 14,000×g) to pellet the precipitate, the acetonitrile is collected and evaporated to dry under a flow of nitrogen. Extracted samples are resuspended in 50 μl acetonitrile, followed by 100 μl distilled H$_2$O, and transferred to HPLC autoinjector vials. Samples are chromatographed using a Nova-Pak C18 column (3.9×150 mm; WAT086344, Waters Corp. Milford, Ma), with a 12 minute linear gradient from 33.3 to 77.7% acetonitrile, 0.1% TFA, using a flow rate of 1 ml/min. A scanning fluorescence detector (#474, Waters Corp) monitoring 480 nm excitation, 580 nm emission quantitates AUC of peaks of interest; mass is extrapolated from a standard curve generated under matching conditions. Results are presented in Table 1, below.

TABLE 1

Conjugate Stability Summary in Blood After 5.5 Hours
(Percent of Control (In Buffer, T = 0))

| | Buffer | Human Blood | Nude Mouse Blood | SEQ ID NO: |
|---|---|---|---|---|
| Ac-PLG-LYAL-Dox | 91.3% | 37.5% | 20.0% | SEQ ID NO: 155 |
| Ac-PLG-LLAL-Dox | 102.0 | 55.6 | 19.2 | SEQ ID NO: 154 |
| Ac-PLG-LAL-Dox | 96.8 | 49.1 | 9.0 | SEQ ID NO: 46 |
| Ac-PLG-LYL-Dox | 112 | 90.1 | — | SEQ ID NO: 47 |
| Ac-PLG-LL-Dox | 106 | 87.2 | 63.8 | SEQ ID NO: 3 |
| Ac-GPLG-LL-Dox | 105 | 42.6 | 25.8 | SEQ ID NO: 52 |
| Ac-GPLG-LAL-Dox | 92.2 | 15.4 | 5.8 | SEQ ID NO: 156 |
| Ac-PLG-L-Dox | 99.2 | 74.7 | 68.2 | SEQ ID NO: 238 |
| Ac-GPLG-L-Dox | 106 | 10.2 | 5.9 | SEQ ID NO: 239 |

Evaluation of Conjugates as MMP and Neprilysin Substrates

Compounds of this invention should be good substrates for specific MMPs but should not be substrates for related proteases which are not exclusively expressed in the tumor environment. An example of such an unwanted protease activity is neprilysin, which was identified as a major metalloprotease in several human tumor cell lines. Neprilysin is expressed in kidney, macrophages, and brain tissues (Li et al.). To enhance the targeting of conjugates to tumor tissue, conjugates were tested as substrates for MMPs and neprilysin. Compounds of this invention have $k_{cat}/K_m > 1000$ mM$^{-1}$s$^{-1}$ when assayed using a relevant MMP and have $k_{cat}/K_m < 1000$ mM$^{-1}$s$^{-1}$ when assayed using neprilysin.

Example 1001

Cleavage of doxorubicin-peptide conjugates with MMPs and Neprilysin

Doxorubicin-peptide conjugates were dissolved in DMSO to 10 mM. The conjugate was initially diluted to 10 μM in Metalloprotease Reaction Buffer (50 mM Hepes pH 7.5, 0.1% Brij 35, 10 mM CaCl$_2$). MMP2, 9, or 14, or neprilysin were diluted to a final concentration of 10 μM into Metalloprotease Reaction Buffer plus 400 mM NaCl. In a reaction volume of 1 ml, the dox-conjugate was diluted to 1 μM in Metalloprotease reaction buffer. The reaction was equilibrated at 37° C. Enzyme was added to initiate reaction, 2 nM MMP-9, or 4 nM MMP-2, or 2.5 nM MMP-14 or 10 nM neprilysin. 100 μL aliquots were withdrawn at indicated time points (0, 5, 10, 15, 20, 30, 40, 50, 60 minutes) and quenched with 10 μL of 0.5 M EDTA. The conjugates and products were separated by reverse phase HPLC on a Waters Alliance HPLC system (2690 separations module with 474 scanning fluorescence detector). A 20 μL sample was loaded on a 3.9 mm X 150 mm Waters C18 Novapak column, and eluted with a 12 minute gradient from 27% to 63% acetonitrile/ 0.1% TFA at 1 ml/minute. Doxorubicin containing peaks were detected by fluorescence, excitation at 480 nM, emission at 580 nM. Peak areas were integrated and the substrate peak area was plotted against time. Data was fitted to a single exponential decay curve where $y=A_o e[-kt]$. $A_o$ is the initial value of y, the area of the substrate peak, and k is the rate constant of the reaction. Since the reaction was run under first order conditions (substrate<<Km), $k_{cat}/K_m$ can be calculated from $k_{cat}/K_m = k/[E_t]$. Results are presented in Table 2.

TABLE 2

| | Enzyme* MMP-9 | MMP-2 | MMP-14 | Neprilysin | SEQ ID NO: |
|---|---|---|---|---|---|
| AcPLG-LYL-Dox | 390,000 | 88,000 | — | 22,000 | SEQ ID NO: 47 |
| AcPLG-LYAL-Dox | 296,000 | 190,000 | 134,000 | 388,000 | SEQ ID NO: 155 |
| AcPLG-LAAL-Dox | 165,000 | 110,000 | — | 120,000 | SEQ ID NO: 157 |
| AcPLG-LLSL-Dox | 149,000 | 103,000 | — | 82,000 | SEQ ID NO: 159 |
| AcPLG-LLAL-Dox | 130,000 | 63,000 | — | 100,000 | SEQ ID NO: 154 |
| AcPLG-LL-Dox | 130,000 | 18,000 | 4,100 | 22,000 | SEQ ID NO: 3 |
| AcGPLG-LL-Dox | 95,000 | 30,000 | — | 20,000 | SEQ ID NO: 52 |
| AcGPLG-LY-Dox | 110,000 | 40,000 | — | 19,000 | SEQ ID NO: 54 |
| AcPLG-LAL-Dox | 24,000 | 53,000 | — | 49,000 | SEQ ID NO: 46 |
| AcGPLG-LAL-Dox | 19,000 | 86,000 | — | 42,000 | SEQ ID NO: 156 |
| AcPLG-HofYL-Dox | 34,000 | >120,000 | >120,000 | <1000 | SEQ ID NO: 103 |
| SucPLG-HofYL-Dox | >120,000 | >120,000 | >120,000 | <1000 | SEQ ID NO: 106 |
| AcPLG-HofOrnL-Dox | 26,000 | 136,000 | >120,000 | <1000 | SEQ ID NO: 116 |

*Where more than one measurement was taken, the value given is an average of the multiple measurements.

Example 1002

Evaluation of conjugates as aminopeptidase substrates.

Conjugates were incubated with 1 nM MMP2 for 3 hours at 37° C. in 50 mM HEPES, 10 mM CaCl$_2$, 0.1% Brij, pH 7.5 to generate LYL-Dox, the post-MMP product. Aminopeptidase N (Boehringer Mannheim #102 768) was then added to 12.5 mUnits/ml to initiate post-MMP processing. Aliquots of the reaction mixture (0.045 mL) were removed after various times (3, 6, 9, 15, 20, 30, and 100 min) and added to tubes with 0.005 ml 0.5 mM EDTA to inhibit aminopeptidase activity. One half of the aliquot from each time was separated on a Novapak C18 column (3.9×150 mm) at a flow rate of 1 mL/min using the gradient outlined in Table 3. For the HPLC gradients: Solvent A is 14 mM NaPi, 0.5 mM triethylamine, pH 4.2; Solvent B is 50% A, 50% Acetonitrile; and Solvent C is Acetonitrile. The fractional composition was determined using the integrated peak areas.

TABLE 3

HPLC Gradient

| Time, min | A, % | B, % | C, % |
|---|---|---|---|
| 0 | 50 | 50 | 0 |
| 12 | 0 | 100 | 0 |
| 18 | 0 | 100 | 0 |
| 19 | 0 | 0 | 100 |
| 22 | 0 | 0 | 100 |
| 22.5 | 50 | 50 | 0 |
| 27 | 50 | 50 | 0 |

Example 1003

Evaluation of Cytotoxicity of Conjugates

The conjugates were tested for cytotoxic effect against the HT1080 cell line, which expresses multiple MMPs. Cells can vary significantly in expression of active MMPS; thus, a given cell line may not be optimal for the evaluation of a given conjugate. HT 1080 cells in culture have significant levels of MMPs 2, 9, and 14 and are consequently especially suitable for the evaluation of conjugates that are substrates for that enzyme.

The cell line was grown in tissue MEM with Earl's salts containing 10% fetal bovine serum (FBS). On day one, 500 cells were seeded into 96 well plates in 200 ul of cell culture medium that containing 10% FBS which had been stripped of bovine gelatinases by prior passage over a gelatin-sepharose column. On day two, peptidyl-Doxorubicin conjugates and Doxorubicin as a control were added to the plates. The cells were incubated for three days at 37° C., 5% $CO_2$ in a tissue culture cell incubator. MTS reagent was added to each microplate well using the manufacturer's instructions (ref). The plates were incubated for 2 hours at 37° C., 5% $CO_2$. The plates were read on a Molecular Devices Spectropmax 250 plate reader at 490 nM. The viability of the cells in each well was then calculated for each concentration of compound tested and compared to the control wells where no compound was added. Representative compounds of the present invention have demonstrated EC50 for cell kill<1=10 µM in this assay; more preferably representative compounds of the present invention have demonstrated EC50 for cell kill<1 µM.

TABLE 4

Cytotoxicity of Conjugates on HT1080 Cells

| Compound | $EC_{50}$ (nM) | SEQ ID NO: |
|---|---|---|
| Doxorubicin | 8–9 | |
| Ac-PLG-LYAL-Dox | <10,000 | SEQ ID NO: 155 |
| Ac-PLG-LLAL-Dox | <10,000 | SEQ ID NO: 155 |

TABLE 4-continued

Cytotoxicity of Conjugates on HT1080 Cells

| Compound | $EC_{50}$ (nM) | SEQ ID NO: |
|---|---|---|
| Ac-PLG-LL-Dox | <10,000 | SEQ ID NO: 3 |
| Ac-PLG-LAL-Dox | <10,000 | SEQ ID NO: 46 |

Alternatively, delivery of active cytotoxic agent may be assessed by incubating the conjugates with cells and assaying the levels of active species by HPLC. An example of this method of evaluation follows.

Example 1004

Analysis of processing by HT1080 cultures

Actively growing HT1080 cells are seeded in a 12 well plate at 2×10⁵ cells per well in DMEM with 10% serum. On the next day, media is removed and cells are washed twice with PBS. 1.5 of DMEM containing 0.1% BSA, 11M Ac-PLG-HofK(Me2)L-Dox (SEQ ID NO: 127) and 40 nM PMA is then added to each well. A broad spectrum MMP inhibitor is added to some samples so that the amount of processing that is due to MMPs can be determined. At the indicated times, 0.1 ml aliquots are removed, added to 0.4 ml acetonitrile, vortexed, and centrifuged for 2 minutes. 0.4 of cleared supernatant is removed and dried using a nitrogen stream. The dried pellet is suspended in 0.12 ml of HPLC Buffer A and analyzed as in Example 1000.

Results from a typical analysis are summarized in Table 5. At the times used in this experiment, the only detectable metabolite is L-Dox. HofK(Me2)L-Dox and K(Me2)L-Dox are not detected since they are rapidly converted to L-Dox. At later times, Dox is formed from L-Dox. Processing is greatly reduced by the MMP inhibitor showing that MMPs are the major processing enzymes in these cells.

TABLE 5

Analysis of processing in HT1080 cultures

| | Fraction of L-Dox | |
|---|---|---|
| Time, hours | Minus MMP inhibitor | Plus MMP inhibitor |
| 0 | 0 | 0 |
| 3 | 0.10 | 0.004 |
| 5.5 | 0.20 | 0.01 |
| 8 | 0.46 | 0.02 |

Example 1005

Chromatographic Studies Designed To Evaluate Preferential Accumulation Of Dox In HT1080 Xenografts Relative To Heart And Plasma Tissues Are Described As Follows.

Conjugate administration and tissue harvesting:

HT1080 tumors are transplanted into naïve Swiss Nude mice from tumor xenograft fragments and allowed to grow in vivo for 1 week. Experimental Dox-conjugates are dissolved in N,N-Dimethyl-acetamide (DMAC) and then diluted with water to yield the desired conjugate concentration in 10% DMAC. 0.2 ml conjugate solution is then injected into tail veins. At various times following injection, three mice are anesthetized with $CO_2$ and blood is collected by cardiac puncture in a syringe containing 0.1 ml Na Citrate. Blood is transferred to a microfuge tube and centrifuged for 2 min in an Eppendorf centrifuge. 0.3 ml of plasma is then transferred to a fresh tube and frozen using liquid nitrogen. Following death, the tumor, left kidney, and heart are removed and frozen using liquid nitrogen. Tissues are stored at −80° C. until extraction.

Tissue extraction:

Samples are thawed, weighed and minced with scissors and cold, citrated mouse plasma (Cocalico Biological (#30–0931) is added. Iced slurries are homogenized for about 1 min. with IKA Ultra-Turrex homogenizer and 0.5 ml is then transferred to a microfuge tube. 0.1 ml of 33% Silver nitrate solution is added immediately after homogenization. 0.5 ml of acetonitrile is then added and the resulting mixture is vortexed briefly, mixed for 15 min, and centrifuged for 5 min. The supernatant is transferred to a fresh tube, dried with a nitrogen stream at 37 degrees C., and stored a−80 degrees C.

Separation, identification and quantification of Dox and Dox-containing compounds in extracted samples:

0.06 ml acetonitrile is added to the thawed, dried samples and vortexed briefly. 0.6 ml Buffer A is then added, and vortexed briefly followed by a 1 min. sonication in a water bath. Samples are centrifuged for 10 min to remove insoluble material and the cleared supernatant is diluted with 60 UL Buffer A to match the composition of the HPLC buffer upon injection. 0.1 ml is then injected onto a Novapak C18 column (3.9×150 mm) at a flow rate of 1 ml/min and eluted with the following gradient:

| Time | % A | % B | % C |
|---|---|---|---|
| 0 | 50 | 50 | 0 |
| 12 | 0 | 100 | 0 |
| 18 | 0 | 100 | 0 |
| 19 | 0 | 0 | 100 |
| 33 | 0 | 0 | 100 |
| 34 | 50 | 50 | 0 |
| 40 | 50 | 50 | 0 (end of run) |

Buffer A: 14 mM NaPi, 0.5 mM Triethylamine, pH 4.2
Buffer B: 50% Buffer A, 50% Acetonitrile
Buffer C: 100% Acetonitrile Detection method is fluorescence, with excitation of 480 mm, emission of 580 mm.

Samples from mouse tissues typically show three major peaks that co-migrate with parental conjugate, authentic Leu-dox and Doxorubicin. To calculate the amount of these species, peak areas from tissue samples are converted to pmol/injection using the equation derived from a Dox standard curve. Pmol/injection values are then multiplied by 2.4 to yield pmol/sample. Pmol/sample values are divided by the tissue mass analyzed (plasma=0.3 ml, tumor=0.086 mg, heart, kidney, liver=0.042 mg) to yield pmol/mass. Average and standard errors are then calculated from pmol/mass values for the 3 samples from each time and tissue. Concentration-time curves, PK parameters, and relative tissue distribution are determined from these average pmol/ mass values.

Additional examples of this invention have been prepared using the methods desclosed herein and evaluated using the methodology described in the Examples above. Representatives of this invention are given in Table 6a through 6g.

TABLE 6a

| Example | Cap-P1-P1'-P2'-X--Doxorubicin | M/Z: | SEQ ID NO: |
|---|---|---|---|
| Example 164 | 4-(2-(5,6,7,8-tetrahydro-naphthenyl))butyl-G-Hof-Y-L-Dox | 1256.6 (M + H + H2O) | SEQ ID NO: 164 |

TABLE 6b

| Example | Cap-P2-P1-P1'-P2'-X--Doxorubicin | M/Z: | SEQ ID NO: |
|---|---|---|---|
| Example 1 | 4-methoxy-benzenesulfonyl-β-Ala-G-Hof-Y-L-Dox | 1277.1 (M − H) | SEQ ID NO: 1 |
| Example 2 | 1,2-C$_6$H$_4$(CO)$_2$-H-G-Hof-Y-L-Dox | 1305.5 (M + H) | SEQ ID NO: 2 |
| Example 41 | acetyl-L-G-L-Y-L-Dox | 1145.8 (M + H) | SEQ ID NO: 41 |
| Example 42 | cyclopropylcarbonyl-L-G-L-Y-L-Dox | 1171.7 (M + H) | SEQ ID NO: 42 |
| Example 43 | cyclobutylcarbonyl-L-G-L-Y-L-Dox | 1185.7 (M + H) | SEQ ID NO: 43 |
| Example 44 | pivaloyl-L-G-L-Y-L-Dox | 1187.8 (M + H) | SEQ ID NO: 44 |

TABLE 6c

| Example | Cap-P3-P2-P1-P1'-X--Doxorubicin | M/Z: | SEQ ID NO: |
|---|---|---|---|
| Example 3 | Acetyl-P-L-G-L-L-Dox | 1079 | SEQ ID NO: 3 |
| Example 4 | Acetyl-P-(R)L-G-L-L-Dox | 1079 | SEQ ID NO: 4 |
| Example 5 | Acetyl-P-(β-Ala)-G-L-L-Dox | 1037 | SEQ ID NO: 5 |
| Example 6 | Acetyl-P-(γ-Abu)-G-L-L-Dox | 1051 | SEQ ID NO: 6 |
| Example 7 | Acetyl-P-Cha-G-L-L-Dox | 1119 (M + Na) | SEQ ID NO: 7 |
| Example 8 | P-L-G-L-L-Dox | 1059.5 (M + Na) | SEQ ID NO: 8 |
| Example 9 | MeOCH$_2$CH$_2$OCH$_2$C(=O)-P-L-G-L-L-Dox | 1153 | SEQ ID NO: 9 |
| Example 10 | MeOCH$_2$CH$_2$OCH$_2$CH$_2$OCH$_2$C(=O)-P-L-G-L-L-Dox | 1197.9 (M + H) | SEQ ID NO: 10 |
| Example 11 | H$_2$NCH$_2$CH$_2$N(CH$_2$CH$_2$)$_2$NCH$_2$C(=O)-P-L-G-L-L-Dox | 1206 | SEQ ID NO: 11 |
| Example 12 | AcHNCH$_2$CH$_2$N(CH$_2$CH$_2$)$_2$NCH$_2$C(=O)-P-L-G-L-L-Dox | 1248 | SEQ ID NO: 12 |
| Example 13 | AcN(CH$_2$CH$_2$)$_2$NCH$_2$C(=O)-P-L-G-L-L-Dox | 1205 | SEQ ID NO: 13 |
| Example 17 | Dmg-P-R-Sar-Hof-L-Dox | 1227 | SEQ ID NO: 17 |
| Example 18 | Acetyl-P-H-G-Hof-L-Dox | 1151.2 (M + H) | SEQ ID NO: 18 |
| Example 19 | Acetyl-P-Orn-G-Hof-L-Dox | 1128.4 (M + H) | SEQ ID NO: 19 |
| Example 20 | Acetyl-P-Dap-G-Hof-L-Dox | 1100 | SEQ ID NO: 20 |
| Example 21 | Acetyl-P-Cit-G-Hof-L-Dox | 1171 | SEQ ID NO: 21 |
| Example 22 | Acetyl-P-L-G-(O-(3-pyridyl-))Y-L-Dox | 1206.523 (M + H) | SEQ ID NO: 22 |
| Example 23 | Acetyl-P-L-G-(O-(4-pyridyl-))Y-L-Dox | 1206.524 (M + H) | SEQ ID NO: 23 |
| Example 24 | Acetyl-P-L-G-(4-aza-)Hof-L-Dox | 1128.517 (M + H) | SEQ ID NO: 24 |
| Example 25 | Acetyl-P-L-G-(O-benzyl-)S-L-Dox | 1141.5 (M − H) | SEQ ID NO: 25 |
| Example 26 | Cbz-P-L-G-(O-(4-pyridylmethyl-))Y-L-Dox | 1312.8 (M + H) | SEQ ID NO: 26 |
| Example 27 | Acetyl-P-L-Sar-L-L-Dox | 1093.534 (M + H) | SEQ ID NO: 27 |

TABLE 6c-continued

| Example | Cap-P3-P2-P1-P1'-X--Doxorubicin | M/Z: | SEQ ID NO: |
|---|---|---|---|
| Example 28 | Acetyl-P-(N-Me-)L-G-L-L-Dox | 1115.518 (M + Na) | SEQ ID NO: 28 |
| Example 29 | Acetyl-P-L-G-(N-Me-)L-L-Dox | 1115.517 (M + Na) | SEQ ID NO: 29 |
| Example 30 | Acetyl-Hyp-L-G-L-L-Dox | 1117.494 (M + Na) | SEQ ID NO: 30 |
| Example 31 | Acetyl-Tzc-L-G-L-L-Dox | 1119.454 (M + Na) | SEQ ID NO: 31 |
| Example 32 | Acetyl-(Homo-P)-L-G-L-L-Dox | 1115.516 (M + Na) | SEQ ID NO: 32 |
| Example 33 | Acetyl-(Homo-P)-L-G-Hof-L-Dox | 1163.516 (M + Na) | SEQ ID NO: 33 |
| Example 34 | Acetyl-(Homo-P)-Orn-G-Hof-L-Dox | 1142.529 (M + Na) | SEQ ID NO: 34 |
| Example 35 | Acetyl-Nipecotate-L-G-L-L-Dox | 1142.529 (M + Na) | SEQ ID NO: 35 |
| Example 36 | Acetyl-Aze-L-G-L-L-Dox | 1087.485 (M + Na) | SEQ ID NO: 36 |
| Example 37 | Acetyl-Chg-L-G-L-L-Dox | 1143.548 (M + Na) | SEQ ID NO: 37 |
| Example 38 | Acetyl-P-valerolactam-G-L-L-Dox | 1085.468 (M + Na) | SEQ ID NO: 38 |
| Example 39 | Acetyl-G-P-L-G-L-F-Dox | 1170.9 (M + H) | SEQ ID NO: 39 |
| Example 40 | Acetyl-G-P-L-G-F-F-Dox | 1204.9 (M + H) | SEQ ID NO: 40 |
| Example 141 | Acetyl-(4-fluoro-F)-L-G-L-L-Dox | 1226.528 (M + Na) | SEQ ID NO: 141 |

TABLE 6d

| Example | Cap-P3-P2-P1-P1'-P2'-X--Doxorubicin | M/Z: | SEQ ID NO: |
|---|---|---|---|
| Example 46 | acetyl-P-L-G-L-A-L-Dox | 1148.8 (M − H) | SEQ ID NO: 46 |
| Example 47 | acetyl-P-L-G-L-Y-L-Dox | 1240.9 (M − H) | SEQ ID NO: 47 |
| Example 48 | Peg-P-L-G-L-Y-L-Dox | 1360.9 (M + H) | SEQ ID NO: 48 |
| Example 49 | H3CC(=O)NH-Peg-P-L-G-L-Y-L-Dox | 1388 | SEQ ID NO: 49 |
| Example 50 | AcHNCH2CH2N(CH2CH2)2NCH2C(=O)-P-L-G-L-Y-L-Dox | 1411.8 (M + H) | SEQ ID NO: 50 |
| Example 51 | acetyl-P-L-G-L-S-L-Dox | 1166 | SEQ ID NO: 51 |
| Example 55 | acetyl-P-L-G-L-L-L-Dox | 1193.4 (M + H) | SEQ ID NO: 55 |
| Example 101 | acetyl-P-L-G-Hof-H-L-Dox | 1264.3 (M + H) | SEQ ID NO: 101 |
| Example 102 | acetyl-P-L-G-Hof-A-L-Dox | 1196.8 (M − H) | SEQ ID NO: 102 |
| Example 103 | acetyl-P-L-G-Hof-Y-L-Dox | 1288.8 (M − H) | SEQ ID NO: 103 |
| Example 104 | acetyl-P-L-G-Hof-(morpholinylpropyl-G)-L-Dox | 1311.6 (M + H) | SEQ ID NO: 104 |
| Example 106 | succinyl-P-L-G-Hof-Y-L-Dox | 1349.6 (M + H) | SEQ ID NO: 106 |
| Example 107 | acetyl-P-L-G-Hof-(O-(4-pyridylmethyl)-Y)-L-Dox | 1381.8 (M + H) | SEQ ID NO: 107 |
| Example 108 | acetyl-P-L-G-(homo-Y)-Y-L-Dox | 1304.6 (M − H) | SEQ ID NO: 108 |
| Example 109 | acetyl-P-L-G-(4-aza-Hof)-Y-L-Dox | 1291.8 (M + H) | SEQ ID NO: 109 |
| Example 110 | acetyl-P-L-G-(O-(4-pyridyl-)-Y)-L-Dox | 1367.6 (M − H) | SEQ ID NO: 110 |
| Example 111 | acetyl-P-L-G-(phenylpropyl-G)-Y-L-Dox | 1302.4 (M − H) | SEQ ID NO: 111 |
| Example 112 | acetyl-P-L-G-(styryl-A)-Y-L-Dox | 1300.5 (M − H) | SEQ ID NO: 112 |
| Example 113 | acetyl-P-L-G-(O-benzyl-S)-Y-L-Dox | 1367.6 | SEQ ID NO: 112 |
| Example 114 | acetyl-P-(N,N-dimethyl-K)-G-Hof-Y-L-Dox | 1333 | SEQ ID NO: 114 |
| Example 115 | acetyl-P-L-G-Hof-Dap-L-Dox | 1213.4 | SEQ ID NO: 115 |
| Example 116 | acetyl-P-L-G-Hof-Orn-L-Dox | 1241.6 (M + H) | SEQ ID NO: 116 |
| Example 117 | Peg-P-L-G-Hof-Orn-L-Dox | 1359.9 (M + H) | SEQ ID NO: 117 |
| Example 120 | acetyl-P-Orn-G-Hof-Orn-L-Dox | 1242 | SEQ ID NO: 120 |
| Example 121 | acetyl-P-Orn-G-Hof-Y-L-Dox | 1351 | SEQ ID NO: 121 |
| Example 123 | acetyl-P-Orn-G-L-Y-L-Dox | 1243.3 (M + H) | SEQ ID NO: 123 |
| Example 124 | acetyl-P-(4-aza-F)-G-L-Y-L-Dox | 1277 | SEQ ID NO: 124 |
| Example 125 | acetyl-P-L-G-Hof-Dab-L-Dox | 1227.6 (M + H) | SEQ ID NO: 125 |
| Example 126 | acetyl-P-L-G-Hof-K-L-Dox | 1254 | SEQ ID NO: 126 |
| Example 127 | acetyl-P-L-G-Hof-(N,N-dimethyl-K)-L-Dox | 1283.6 (M + H) | SEQ ID NO: 127 |
| Example 129 | Peg-P-L-G-Hof-(N,N-dimethyl-K)-L-Dox | 1401 | SEQ ID NO: 128 |
| Example 132 | acetyl-P-L-G-Hof-(N,N-dimethyl-K)-Nle-Dox | 1283 | SEQ ID NO: 132 |
| Example 133 | acetyl-P-L-G-Hof-(N,N-dimethyl-K)-Cha-Dox | 1323 | SEQ ID NO: 133 |
| Example 134 | acetyl-P-L-G-Hof-Cit-L-Dox | 1284.4 (M + H) | SEQ ID NO: 134 |
| Example 136 | acetyl-P-L-G-Hof-Q-L-Dox | 1255.8 (M + H) | SEQ ID NO: 136 |
| Example 137 | acetyl-P-L-G-Hof-(4-aza-F)-L-Dox | 1275.6 (M + H) | SEQ ID NO: 137 |
| Example 138 | acetyl-P-L-G-Hof-V-L-Dox | 1224.1 (M − H) | SEQ ID NO: 138 |
| Example 142 | acetyl-(homo-P)-L-G-L-Y-L-Dox | 1278.578 (M + Na) | SEQ ID NO: 142 |
| Example 143 | acetyl-(homo-P)-L-G-Hof-Orn-L-Dox | 1256.624 (M + Na) | SEQ ID NO: 143 |
| Example 144 | acetyl-Aze-L-G-L-Y-L-Dox | 1250.549 (M + Na) | SEQ ID NO: 144 |
| Example 145 | acetyl-Aze-L-G-Hof-Orn-L-Dox | 1227.585 (M + Na) | SEQ ID NO: 145 |
| Example 146 | acetyl-P-L-G-L-Y-G-Dox | 1208.5020 (M + Na) | SEQ ID NO: 146 |
| Example 147 | acetyl-P-L-G-Hof-Y-G-Dox | 1256.5040 (M + Na) | SEQ ID NO: 147 |
| Example 148 | acetyl-P-L-G-L-Y-(β-homo-L)-Dox | 1278.5830 (M + Na) | SEQ ID NO: 148 |
| Example 149 | acetyl-P-L-G-Hof-Y-(β-homo-L)-Dox | 1326.5810 (M + Na) | SEQ ID NO: 149 |
| Example 150 | acetyl-P-L-G-L-Y-(β-Ala)-Dox | 1222.5150 (M + Na) | SEQ ID NO: 150 |
| Example 151 | acetyl-P-L-G-L-Y-Ahx-Dox | 1264.5650 (M + Na) | SEQ ID NO: 151 |
| Example 152 | acetyl-P-L-G-L-Y-Aph-Dox | 1326.5820 (M + Na) | SEQ ID NO: 152 |
| Example 153 | acetyl-P-L-G-L-Y-Amh-Dox | 1292.5950 (M + Na) | SEQ ID NO: 153 |
| Example 165 | acetyl-P-L-G-Hof-(N-methylpiperazinepropyl-G)-L-Dox | 1324.6 (M + H) | SEQ ID NO: 165 |
| Example 166 | tetrazoleacetyl-P-L-G-Hof-Y-L-Dox | 1356.4 (M − H) | SEQ ID NO: 166 |
| Example 167 | tetrazoleacetyl-P-L-G-(O-benzyl-S)-Y-L-Dox | 1372.5 (M − H) | SEQ ID NO: 167 |
| Example 168 | tetrazoleacetyl-P-L-G-Hof-Y-Nle-Dox | 1356.5 (M − H) | SEQ ID NO: 168 |
| Example 169 | P-L-G-(O-benzyl-S)-Y-L-Dox | 1264.5 (M − H) | SEQ ID NO: 169 |
| Example 170 | acetyl-P-L-G-Hof-(homoY)-L-Dox | 1302.5 (M − H) | SEQ ID NO: 170 |
| Example 171 | acetyl-P-AzaHof-G-AzaHof-Y-L-Dox | 1340.4 (M + H) | SEQ ID NO: 171 |
| Example 172 | acetyl-P-L-G-(O-allyl-S)-Y-L-Dox | 1254.6 (M − H) | SEQ ID NO: 172 |

TABLE 6d-continued

| Example | Cap-P3-P2-P1-P1'-P2'-X--Doxorubicin | M/Z: | SEQ ID NO: |
|---|---|---|---|
| Example 173 | acetyl-P-L-G-(4-nitro-Hof)-Y-L-Dox | 1333.4 (M − H) | SEQ ID NO: 173 |
| Example 174 | acetyl-P-L-G-Hof-AzaHof-L-Dox | 1289.6 (M + H) | SEQ ID NO: 174 |
| Example 175 | acetyl-P-L-G-(O-methyl-S)-Y-L-Dox | 1228.6 (M − H) | SEQ ID NO: 175 |
| Example 178 | 3-pyridinecarbonyl-P-L-G-Hof-Y-L-Dox | 1353.6 (M + H) | SEQ ID NO: 178 |
| Example 179 | 2-pyrazinecarbonyl-P-L-G-Hof-Y-L-Dox | 1352.7 (M − H) | SEQ ID NO: 179 |
| Example 180 | Ac-P-L-G-Hof-K(ME2)-Nle-Dox | 1283.5 (M + H) | SEQ ID NO: 180 |
| Example 181 | Ac-P-L-G-Hof-Y-Hos Dox | 1300.5 (M + Na) | SEQ ID NO: 181 |
| Example 182 | Ac-P-L-G-Hof-Y-Hol-Dox | 1326.2 (M + Na) | SEQ ID NO: 182 |
| Example 183 | Ac-P-L-G-Thr(OBzl)-Y-L-Dox | 1342.4 (M + Na) | SEQ ID NO: 183 |

TABLE 6e

| Example | Cap-P4-P3-P2-P1-P1'-X-Doxorubicin | M/Z: | SEQ ID NO: |
|---|---|---|---|
| Example 45 | Hyp-G-P-L-G-L-L-Dox | 1207 | SEQ ID NO: 45 |
| Example 52 | acetyl-G-P-L-G-L-L-Dox | 1136 | SEQ ID NO: 52 |
| Example 53 | O(CH$_2$CH$_2$)NCH$_2$CH$_2$NHC(=O)-G-P-L-G-L-L-Dox | 1250 | SEQ ID NO: 53 |
| Example 54 | acetyl-G-P-L-G-L-Y-Dox | 1208.5 (M + Na) | SEQ ID NO: 54 |
| Example 56 | acetyl-G-P-L-G-Bip-F-Dox | 1280 | SEQ ID NO: 56 |
| Example 57 | acetyl-G-P-L-G-Nle-F-Dox | 1170 | SEQ ID NO: 57 |
| Example 58 | Cbz-G-P-L-G-L-L-Dox | 1251 | SEQ ID NO: 58 |
| Example 59 | AcHNCH$_2$CH$_2$N(CH$_2$CH$_2$)$_2$NCH$_2$C(=O)-G-P-L-G-L-L-Dox | 1306 | SEQ ID NO: 59 |
| Example 60 | H$_2$NCH$_2$CH$_2$N(CH$_2$CH$_2$)$_2$NCH$_2$C(=O)-G-P-L-G-L-L-Dox | 1262 | SEQ ID NO: 60 |
| Example 61 | Dmg-P-L-G-L-L-Dox | 1122 | SEQ ID NO: 61 |
| Example 62 | acetyl-γ-E-P-L-G-L-L-Dox | 1208 | SEQ ID NO: 62 |
| Example 63 | acetyl-G-P-L-G-Tha-F-Dox | 1210 | SEQ ID NO: 63 |
| Example 64 | acetyl-G-P-L-G-Phg-F-Dox | 1190.8 (M + H) | SEQ ID NO: 64 |
| Example 65 | methoxyacetyl-G-P-L-G-L-L-Dox | 1166 | SEQ ID NO: 65 |
| Example 66 | Dmg-P-L-G-Tha-L-Dox | 1220 | SEQ ID NO: 66 |
| Example 67 | Dmg-P-L-G-Phg-L-Dox | 1199 | SEQ ID NO: 67 |
| Example 68 | Dmg-P-L-G-(O-benzyl-Y)-L-Dox | 1319 | SEQ ID NO: 68 |
| Example 69 | Dmg-P-L-G-Bip-L-Dox | 1289 | SEQ ID NO: 69 |
| Example 70 | acetyl-G-P-L-G-F-Bip-Dox | 1279 | SEQ ID NO: 70 |
| Example 71 | acetyl-G-P-L-G-L-Bip-Dox | 1247 | SEQ ID NO: 71 |
| Example 72 | acetyl-G-P-L-G(2Nal)-Bip-Dox | 1130 | SEQ ID NO: 72 |
| Example 73 | acetyl-G-P-L-G-F-A-Dox | 1127 | SEQ ID NO: 73 |
| Example 74 | acetyl-G-P-L-G-Bip-A-Dox | 1204 | SEQ ID NO: 74 |
| Example 75 | acetyl-G-P-L-G-L-A-Dox | 1094 | SEQ ID NO: 75 |

TABLE 6e-continued

| Example | Cap-P4-P3-P2-P1-P1'-X-Doxorubicin | M/Z: | SEQ ID NO: |
|---|---|---|---|
| Example 76 | acetyl-G-P-L-G-(O-benzyl-Y)-F-Dox | 1310 | SEQ ID NO: 76 |
| Example 77 | acetyl-G-P-Q-G-L-L-Dox | 1151.8 (M + H) | SEQ ID NO: 77 |
| Example 78 | acetyl-G-P-R-G-L-L-Dox | 1179 | SEQ ID NO: 78 |
| Example 79 | acetyl-G-P-L-G-L-(4-pyridyl-A)-Dox | 1171 | SEQ ID NO: 79 |
| Example 80 | acetyl-G-P-L-G-L-R-Dox | 1178 | SEQ ID NO: 80 |
| Example 81 | acetyl-G-P-L-G-L-W-Dox | 1208 | SEQ ID NO: 81 |
| Example 82 | acetyl-G-P-L-G-L-V-Dox | 1121 | SEQ ID NO: 82 |
| Example 83 | acetyl-G-P-L-G-Hof-L-Dox | 1184.8 (M + H) | SEQ ID NO: 83 |
| Example 84 | acetyl-G-P-L-A-L-L-Dox | 1150 | SEQ ID NO: 84 |
| Example 85 | Dmg-P-I-G-Bip-L-Dox | 1232.8 (M + H) | SEQ ID NO: 85 |
| Example 86 | Dmg-P-Chg-G-Bip-L-Dox | 1258 | SEQ ID NO: 86 |
| Example 87 | acetyl-G-P-V-G-L-L-Dox | 1122 | SEQ ID NO: 87 |
| Example 88 | Dmg-P-I-G-L-L-Dox | 1122 | SEQ ID NO: 88 |
| Example 89 | Dmg-P-R-G-Bip-L-Dox | 1274 | SEQ ID NO: 89 |
| Example 90 | acetyl-G-P-L-G-L-(O-benzyl-Y)-Dox | 1276 | SEQ ID NO: 90 |
| Example 91 | acetyl-G-P-L-G-E-L-Dox | 1152 | SEQ ID NO: 91 |
| Example 92 | Dmg-P-K-G-Bip-L-Dox | 1247 | SEQ ID NO: 92 |
| Example 93 | acetyl-G-P-L-G-L-E-Dox | 1152 | SEQ ID NO: 93 |
| Example 94 | acetyl-G-P-L-G-Bip-E-Dox | 1262 | SEQ ID NO: 94 |
| Example 98 | acetyl-G-P-L-G-N-L-Dox | 1137 | SEQ ID NO: 98 |
| Example 99 | acetyl-G-P-L-G-S-L-Dox | 1110.3 (M + H) | SEQ ID NO: 99 |
| Example 100 | acetyl-G-P-L-G-(4-hydroxy-phenyl-G)-L-Dox | 1172 | SEQ ID NO: 100 |
| Example 140 | acetyl-G-Aze-L-G-L-L-Dox | 1144.5 (M + Na) | SEQ ID NO: 140 |

TABLE 6f

| Example | Cap-P4-P3-P2-P1-P1'-P2'-X--Doxorubicin | M/Z: | SEQ ID NO: |
|---|---|---|---|
| Example 95 | Dmg-P-R-Sar-Hof-R-L-Dox | 1384 | SEQ ID NO: 95 |
| Example 96 | Dmg-P-R-G-Hof-R-L-Dox | 1370 | SEQ ID NO: 96 |
| Example 97 | Dmg-P-R-G-Bip-R-L-Dox | 1432 | SEQ ID NO: 97 |
| Example 105 | acetyl-γ-E-P-L-G-Hof-Y-L-Dox | 1419.8 (M + H) | SEQ ID NO: 105 |
| Example 118 | acetyl-γ-E-P-L-G-Hof-Orn-L-Dox | 1370 | SEQ ID NO: 118 |
| Example 119 | γ-E-P-L-G-Hof-Orn-L-Dox | 1328 | SEQ ID NO: 119 |
| Example 122 | acetyl-γ-E-P-Orn-G-Hof-E-L-Dox | 1386 | SEQ ID NO: 122 |
| Example 128 | Dmg-P-L-G-Hof-(N,N-dimethyl-K)-L-Dox | 1326 | SEQ ID NO: 128 |
| Example 130 | acetyl-γ-E-P-L-G-Hof-(N,N-dimethyl-K)-L-Dox | 1410 | SEQ ID NO: 130 |
| Example 131 | γ-E-P-L-G-Hof-(N,N-dimethyl-K)-L-Dox | 1370 | SEQ ID NO: 131 |

TABLE 6f-continued

| Example | Cap-P4-P3-P2-P1-P1'-P2'-X--Doxorubicin | M/Z: | SEQ ID NO: |
|---|---|---|---|
| Example 135 | acetyl-γ-E-P-L-G-Hof-Cit-L-Dox | 1413 | SEQ ID NO: 135 |
| Example 139 | acetyl-γ-E-P-L-G-Hof-E-L-Dox | 1407.4 (M + Na) | SEQ ID NO: 139 |
| Example 156 | acetyl-G-P-L-G-L-A-L-Dox | 1207 | SEQ ID NO: 156 |
| Example 161 | Dmg-P-L-G-L-Y-L-Dox | 1285 | SEQ ID NO: 161 |
| Example 162 | Dmg-P-R-G-Phg-Y-L-Dox | 1348 | SEQ ID NO: 162 |
| Example 163 | acetyl-G-P-L-G-L-R-L-Dox | 1292 | SEQ ID NO: 163 |
| Example 176 | acetyl-γ-E-P-L-G-(O-benzyl-S)-Y-L-Dox | 1433.5 (M − H) | SEQ ID NO: 176 |
| Example 177 | acetyl-γ-E-P-L-G-(O-benzyl-S)-Y-Nle-Dox | 1433.5 (M − H) | SEQ ID NO: 177 |
| Example 184 | Ac-γ-E-P-L-G-Hof-Y-Nle-Dox | 1419.9 (M + H) | SEQ ID NO: 184 |

TABLE 6g

| Example | Cap-P3-P2-P1-P1'-P2'-P3'--X--Doxorubicin | M/Z: | SEQ ID NO: |
|---|---|---|---|
| Example 154 | acetyl -P-L-G-L-L-A-L-Dox | 1263 | SEQ ID NO: 154 |
| Example 155 | acetyl -P-L-G-L-Y-A-L-Dox | 1313 | SEQ ID NO: 155 |
| Example 157 | acetyl -P-L-G-L-A-A-L-Dox | 1221 | SEQ ID NO: 157 |
| Example 158 | acetyl -P-L-G-L-A-L-L-Dox | 1263 | SEQ ID NO: 158 |
| Example 159 | acetyl -P-L-G-L-L-S-L-Dox | 1279 | SEQ ID NO: 159 |
| Example 160 | acetyl -P-L-G-L-L-L-L-Dox | 1306 | SEQ ID NO: 160 |

What is claimed is:

1. A compound of Formula (I):

$$E^{cp}\text{-A} \qquad (I)$$

or a pharmaceutically acceptable salt form thereof, wherein;

$E^{cp}$ is an enzyme cleavable peptide conjugated to A and selected from:

Cap-Paa-Xa2-Gly-Xp1-Laa-;
Cap-Xa2-Gly-Xp1-Laa-;
Cap-Paa-Xa2-Gly-Xp1-Xp2-Laa-;
Cap-Xa2-Gly-Xp1-Xp2-Laa-;
Cap-Gly-Xp1-Xp2-Laa-;
Cap-Paa-Xa2-Gly-Xp1-Xp2-Xp3-Laa-;
Cap-Xa2-Gly-Xp1-Xp2-Xp3-Laa-;
Cap-Gly-Xp1-Xp2-Xp3-Laa-;
Cap-Paa-Xa2-Sar-Xp1-Laa-;
Cap-Xa2-Sar-Xp1-Laa-;
Cap-Paa-Xa2-Sar-Xp1-Xp2-Laa-;
Cap-Xa2-Sar-Xp1-Xp2-Laa-;
Cap-Sar-Xp1-Xp2-Laa-;
Cap-Paa-Xa2-Sar-Xp1-Xp2-Xp3-Laa-;
Cap-Xa2-Sar-Xp1-Xp2-Xp3-Laa-; and
Cap-Sar-Xp1-Xp2-Xp3-Laa-;

Paa is a Pro, Hyp, Aze, homo-Pro, Chg, Fph, Npa, Tzc, or proline mimetic;

Xa2 is a natural amino acid;

Xp1 is an amino acid wherein -Gly-Xp1- or -Sar-Xp1- form a bond cleavable by a matrixin;

Xp2 is an amino acid;

Xp3 is an amino acid;

Laa is an amino acid selected from Leu, Ile, Nle, β-homo-Leu, Hol, Hos, Ala, β-Ala, Cha, Cba, Cta, 4-pyridyl-Ala, 3-pyridyl-Ala, 2-pyridyl-Ala, Gly, Abu, Aib, Iva, Nva, Ahx, Aph, Amh, Phe, Bip, Glu, Arg, Trp, Tyr, O—($C_1$–$C_4$ alkyl)-Tyr, O-(phenyl($C_1$–$C_4$ alkyl)-)-Tyr, ($C_3$–$C_8$ alkyl)-Gly, and aminoalkyl carboxylic acid;

Cap is an N-terminus group selected from R—; Xa4-; and R-Xa4-;

Xa4- is an amino acid;

R is an amino capping group; and

A is an antineoplastic agent;

with the following provisos:
a) Cap is not hydrogen;
b) Cap is not a polyhydroxyalkanoyl;
c) Cap is not a non-natural amino acid or succinyl;
d) Cap is not benzyloxycarbonyl (Cbz);
e) $E^{cp}$ does not comprise a dipeptide linkage selected from -Tyr-Ser-; -Tyr-Thr-; -Phe-Ser-; -Gln-Ser-; -Gln-Thr-, and -Asn-Ser; and
f) $E^{cp}$ is not -Gly-Gly-Arg-Leu-(SEQ ID NO: 225), $E_{cp}$ is not -Gly-Val-Phe-Arg-(SEQ ID NO: 226), $E_{cp}$ is not -Ala-Pro-Gly-Leu-(SEQ ID NO: 227), $E_{cp}$ is not 2-thienylalanine-Gly-Ala-Leu-, $E_{cp}$ is not 2-naphthylalanine -Gly-Ala-Leu-, or $E_{cp}$ is not -Gly-Leu-Gly-Leu-(SEQ ID NO: 230).

2. A compound of claim 1 wherein A is doxorubicin, a doxorubicin derivative, or a doxorubicin analogue.

3. A compound of claim 2 wherein A is doxorubicin.

4. A compound of claim 3 of Formula (Ia):

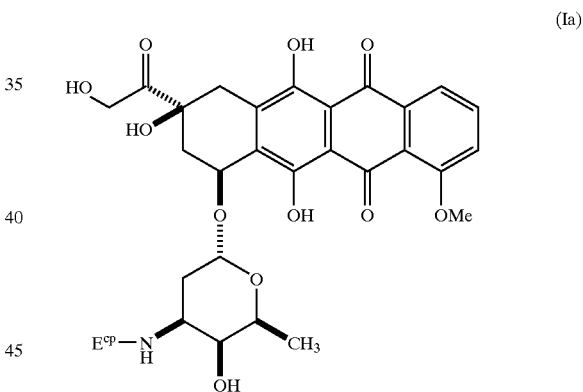

(Ia)

or a pharmaceutically acceptable salt form thereof, wherein;

$E_{cp}$ is an enzyme cleavable peptide selected from:
Cap-Paa-Xa2-Gly-Xp1-Laa-;
Cap-Xa2-Gly-Xp1-Laa-;
Cap-Paa-Xa2-Gly-Xp1-Xp2-Laa-;
Cap-Xa2-Gly-Xp1-Xp2-Laa-;
Cap-Gly-Xp1-Xp2-Laa-;
Cap-Paa-Xa2-Gly-Xp1-Xp2-Xp3-Laa-;
Cap-Xa2-Gly-Xp1-Xp2-Xp3-Laa-;
Cap-Gly-Xp1-Xp2-Xp3-Laa-;
Cap-Paa-Xa2-Sar-Xp1-Laa-;
Cap-Xa2-Sar-Xp1-Laa-;
Cap-Paa-Xa2-Sar-Xp1-Xp2-Laa-;
Cap-Xa2-Sar-Xp1-Xp2-Laa-;
Cap-Sar-Xp1-Xp2-Laa-;
Cap-Paa-Xa2-Sar-Xp1-Xp2-Xp3-Laa-;

Cap-Xa2-Sar-Xp1-Xp2-Xp3-Laa-; and
Cap-Sar-Xp1-Xp2-Xp3-Laa-;

Paa is a Pro, Hyp, Aze, homo-Pro, Chg, Fph, Npa, Tzc, or proline mimetic;

Xa2 is an amino acid;

Xp1 is an amino acid wherein-Gly-Xp1- or-Sar-Xp1-form a bond cleavable by a matrixin;

Xp2 is an amino acid;

Xp3 is an amino acid;

Laa is an amino acid selected from Leu, Ile, Nle, β-homo-Leu, Hol, Hos, Ala, β-Ala, Cha, Cba, Cta, 4-pyridyl-Ala, 3-pyridyl-Ala, 2-pyridyl-Ala, Gly, Abu, Aib, Iva, Nva, Ahx, Aph, Amh, Phe, Bip, Glu, Arg, Trp, Tyr, O—($C_1$–$C_4$ alkyl)-)-Tyr, O-(phenyl($C_1$–$C_4$ alkyl)-)-Tyr, ($C_3$–$C_8$ alkyl)-Gly, and aminoalkyl carboxylic acid;

Cap is an N-terminus group selected from R—; Xa4-; and R-Xa4-;

Xa4-is an amino acid;

R is selected from: $H_3CC(=O)—$;
 $HOC(=O)—(CH_2)_vC(=O)-$,
  wherein v is 1, 2, 3, 4, 5, or 6;
 $H_3CO—(CH_2CH_2O)_t—CH_2C(=O)—$,
 $HO_2CCH_2O—(CH_2CH_2O)_t—CH_2C(=O)—$,
 $H_2N—(CH_2CH_2O)_t—CH_2C(=O)—$, and
 $H_3CC(=O)HN—(CH_2CH_2O)_t—CH_2C(=O)—$,
  wherein t is 1, 2, 3, or 4;
 $R^1—C(=O)—$;
 $R^1—S(=O)_2—$;
 $R^1—NHC(=O)—$;
 $R^{1a}-CH_2C(=O)—$;
 proline substituted with —$OR^3$;
 $C_1$–$C_4$ alkyl substituted with 0–1 $R^4$; and
 2-carboxyphenyl-C(=O)—;

$R^1$ is $C_3$–$C_6$ cycloalkyl substituted with 0, 1, or 2 substituents selected from —OH, methoxy and —$CO_2H$;
 5–6 membered heterocycle; said heterocycle being saturated, partially saturated or unsaturated; said heterocycle containing 1, 2, 3, or 4 heteroatoms selected from N, O, and S; said heterocycle optionally substituted with 1 or 2-OH, methoxy or —$CO_2H$;
 phenyl substituted with 0, 1, or 2 substituents selected from —OH, methoxy and —$CO_2H$; or
 $C_1$–$C_6$ alkyl substituted with 0–4 $R^{1a}$;

$R^{1a}$ is —OH, $C_1$–$C_3$ alkyl, $C_1$–$C_4$ alkoxy, —$CO_2H$, —N($CH_2CH_2$)$_2$N—$R^2$, —$SO_3H$;
 $C_3$–$C_6$ cycloalkyl substituted with 0, 1, or 2 substituents selected from methoxy and —OH;
 5–6 membered heterocycle; said heterocycle being saturated, partially saturated or unsaturated; said heterocycle containing 1, 2, 3, or 4 heteroatoms selected from N, O, and S; said heterocycle optionally substituted with 1 or 2-OH; or
 phenyl substituted with 0, 1, or 2 substituents selected from methoxy and —OH;

$R^2$ is —H, $H_2N(C_2$–$C_4$ alkyl)-, acetyl(H)N($C_2$–$C_4$ alkyl)-, or acetyl;

$R^3$ is —H, $C_1$–$C_4$ alkyl, $C_3$–$C_6$ cycloalkyl, phenyl, or benzyl;

$R^4$ is —OH, $C_1$–$C_3$ alkyl, $C_1$–$C_4$ alkoxy, —$CO_2H$, —N($CH_2CH_2$)$_2$N—$R^2$;
 $C_3$–$C_6$ cycloalkyl substituted with 0, 1, or 2 substituents selected from methoxy and —OH;

5–6 membered heterocycle; said heterocycle being saturated, partially saturated or unsaturated; said heterocycle containing 1, 2, 3, or 4 heteroatoms selected from N, O, and S; said heterocycle optionally substituted with 1 or 2—OH; or
 $C_6$–$C_{10}$ carbocycle substituted with 0, 1, or 2 substituents selected from methoxy and —OH.

5. A compound of claim 4 of Formula (Ia), or a pharmaceutically acceptable salt form thereof, wherein;

$E^{CP}$ is an enzyme cleavable peptide selected from:

Cap-Paa-Xa2-Gly-Xp1-Laa-;
Cap-Xa2-Gly-Xp1-Laa-;
Cap-Paa-Xa2-Gly-Xp1-Xp2-Laa-;
Cap-Xa2-Gly-Xp1-Xp2-Laa-;
Cap-Gly-Xp1-Xp2-Laa-;
Cap-Paa-Xa2-Gly-Xp1-Xp2-Xp3-Laa-;
Cap-Xa2-Gly-Xp1-Xp2-Xp3-Laa-; and
Cap-Gly-Xp1-Xp2-Xp3-Laa-;

Paa is a Pro, Hyp, Aze, homo-Pro, Chg, Fph, Npa, Tzc, or proline mimetic;

Xa2 is an amino acid;

Xp1 is an amino acid wherein-Gly-Xp1-forms a bond cleavable by a matrixin;

Xp2 is an amino acid;

Xp3 is an amino acid;

Laa is an amino acid selected from Leu, Ile, Nle, p-homo-Leu, Hol, Hos, Ala, β-Ala, Cha, Cba, Cta, 4-pyridyl-Ala, Abu, Aib, Iva, Nva, Phe, Bip, Tyr, and O-benzyl-Tyr; and Cap is an N-terminus group selected from R—; Xa4-; and R-Xa4-;

Xa4-is an amino acid;

R is selected from: $H_3CC(=O)—$;
 $HOC(=O)—(CH2)_vC(=O)$,
  wherein v is 1, 2, 3, or 4;
 $H_3CO—(CH_2CH_2O)_t—CH_2C(=O)—$,
 $HO_2CCH_2O—(CH_2CH_2O)_t—CH_2C(=O)—$,
 $H_2N—(CH_2CH_2O)_tCH_2C(=O)—$, and
 $H_3CC(=O)HN—(CH_2CH_2O)_tCH_2C(=O)—$,
  wherein t is 1, 2, or 3;
 $R^1—C(=O)—$;
 $R^1—S(=O)_2—$;
 $R^1—NHC(=O)—$;
 $R^{1a}-CH_2C(=O)—$;
 proline substituted with —$OR^3$;
 $C_1$–$C_4$ alkyl substituted with 0–1 $R^4$;
 $HO_3SCH_2CH(NH_2)C(=O)—$; and
 2-carboxyphenyl-C(=O)—;

$R^1$ is $C_3$–$C_6$ cycloalkyl substituted with 0, 1, or 2 substituents selected from —OH, methoxy and —$CO_2H$;
 5–6 membered heterocycle; said heterocycle being saturated, partially saturated or unsaturated; said heterocycle containing 1, 2, 3, or 4 heteroatoms selected from N, O, and S; said heterocycle optionally substituted with 1 or 2—OH, methoxy or —$CO_2H$;
 phenyl substituted with 0, 1, or 2 substituents selected from —OH, methoxy and —$CO_2H$; or
 $C_1$–$C_6$ alkyl substituted with 0–4 $R^{1a}$;

$R^{1a}$ is —OH, $C_1$–$C_3$ alkyl, $C_1$–$C_4$ alkoxy, —$CO_2H$, —N($CH_2CH_2$)$_2$N—$R^2$, —$SO_3H$;
 $C_3$–$C_6$ cycloalkyl substituted with 0, 1, or 2 substituents selected from methoxy and —OH;

5–6 membered heterocycle; said heterocycle being saturated, partially saturated or unsaturated; said heterocycle containing 1, 2, 3, or 4 heteroatoms selected from N, O, and S; said heterocycle optionally substituted with 1 or 2-OH; or phenyl substituted with 0, 1, or 2 substituents selected from methoxy and —OH;

$R^2$ is —H, $H_2N(C_2-C_4$ alkyly, acetyl(H)N($C_2-C_4$ alkyl)-, or acetyl;

$R^3$ is —H, $C_1-C_4$ alkyl, $C_3-C_6$ cycloalkyl, phenyl, or benzyl;

$R^4$ is —OH, $C_1-C_3$ alkyl, $C_1-C_4$ alkoxy, —$CO_2H$, —$N(CH_2CH_2)_2N$—$R^2$;

$C_3-C_6$ cycloalkyl substituted with 0, 1, or 2 substituents selected from methoxy and —OH;

5–6 membered heterocycle; said heterocycle being saturated, partially saturated or unsaturated; said heterocycle containing 1, 2, 3, or 4 heteroatoms selected from N, O, and S; said heterocycle optionally substituted with 1 or 2—OH; or $C_6-C_{10}$ carbocycle substituted with 0, 1, or 2 substituents selected from methoxy and —OH.

6. The compound of claim 5, wherein -Gly-Xp1- forms a bond cleavable by the matrixin selected from MMP-2, MMP-9, and MMP-14.

7. The compound of claim 5, wherein -Gly-Xp1- forms a bond cleavable by the matrixin selected from MMP-2 and MMP-9.

8. The compound of claim 5, wherein -Gly-Xp1- forms a bond cleavable by the matrixin MMP-14.

9. The compound of claim 5, wherein -Gly-Xp1- forms a bond cleavable by MMP-2, MMP-9, and MMP-14.

10. A compound of claim 5 of Formula (Ia), or a pharmaceutically acceptable salt form thereof, wherein;

$E^{cp}$ is an enzyme cleavable peptide selected from:

Cap-Paa-Xa2-Gly-Xp1-Laa-;

Cap-Xa2-Gly-Xp1-Laa-;

Cap Paa-Xa2-Gly-Xp1-Xp2-Laa-;

Cap-Xa2-Gly-Xp1-Xp2-Laa-;

Cap-Gly-Xp1-Xp2-Laa-;

Cap-Paa-Xa2-Gly-Xp1-Xp2-Xp3-Laa-;

Cap-Xa2-Gly-Xp1-Xp2-Xp3-Laa-; and

Cap-Gly-Xp1-Xp2-Xp3-Laa-;

wherein -Gly-Xp1- forms a bond cleavable by a matrixin;

Paa is a Pro, Hyp, Aze, homo-Pro, Chg, Fph, Npa, Tzc, or proline mimetic of formula:

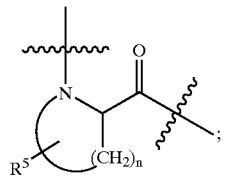

wherein $R^5$ is selected from H, halogen, $C_1-C_6$ alkyl, —OH, $C_1-C_6$ alkoxy, and benzyloxy; and n is 2, 3, 4, or 5;

Xa2 is an amino acid selected from

Hof, Leu, His, Arg, Gin, lie, Val, Lys, (R)-Leu, Orn, β-Ala, γ-Abu, Cha, Chg, Dap, Cit, N-methyl-Leu, valerolactam, N,N-dimethyl-Lys, 4aza-Phe, morpholinylpropyl-Gly, N-methylpiperazinepropyl-Gly, 4-aza-Hof, Ala, Asn, Asp, Aze, Cys, Glu, Gly, Hyp, Irg, Met, Phe, Phe(4-fluoro), Pro, Sar, Ser, Thr, Trp, Tyr, Cya, Hca, and Spa;

Xp1 is an amino acid selected from Hof; Leu; Bip; Phe; nor-Leu; Tha; Phg; Val; Glu; Asn; Ser; Ala; homo-Tyr; Aze; 4aza-Hof; O-(3-pyridyl)Tyr; O-(4-pyridyl)-Tyr; O-benzyl-Tyr; O-benzyl-Thr; O-benzyl-Ser; O-methyl-Ser; O-allyl-Ser; 4-nitro-Hof; N-methyl-Leu; O-(4-pyridylmethyl)Tyr; 4-hydroxy-phenyl-Gly; phenylpropyl-Gly; styryl-Ala, and 2Nal;

Xp2 is an amino acid selected from Tyr; Ala; Ser; Leu; Gln; Val; Glu, His; Lys; Arg; Orn; Aze; Hof; homo-Tyr; Cit; 4-aza-Phe; N,N-dimethyl-Lys; Dab; Dap; Asn, Asp, Aze, Cha, Cys, Gly, Hyp, Ile, Irg, Met, Phe, Phe(4-fluoro), Pro, Sar, Thr, Trp, Cya, Hca, Spa, morpholinylpropyl-Gly; O-(4-pyridylmethylyl)-Tyr; and N-methylpiperazinepropyl-Gly;

Xp3 is an amino acid selected from Tyr, Ala, Ser, Leu, Hof, Arg, Asn, Asp, Aze, Cha, Cys, Dpa, Gin, Glu, Gly, His, Hyp, Ile, Irg, Lys, Met, Orn, Phe, Phe(4-fluoro), Pro, Sar, Thr, Trp, and Val;

Laa is an amino acid selected from Leu, Ile, Nle, p-homo-Leu, Hol, Hos, Ala, β-Ala, Cha, Cba, Cta, 4-pyridyl-Ala, Abu, Aib, Iva, Nva, and Phe;

Cap is an N-terminus group selected from R—; Xa4-; and R-Xa4-;

Xa4- is an amino acid selected from Gly, Pro, γ-Glu, Dmg, Ala, Arg, Asn, Asp, β-Asp, Aze, Cha, Cys, Dpa, Gin, Glu, His, Hyp, Ile, Irg, Leu, Lys, Met, Orn, Phe, Sar, Ser, Thr, Trp, Tyr, and Val;

R is selected from: $H_3CC(=O)$—;
$HOC(=O)CH_2CH_2C(=O)$—;
$HOC(=O)CH_2CH_2CH_2C(=O)$—;
$HOC(=O)CH_2CH2CH_2CH_2C(=O)$—;
$H_3COCH_2CH_2OCH_2C(=O)$—;
$H_3COCH_2CH_2OCH_2CH_2OCH_2C(=O)$—;
$HO_2CCH_2OCH_2CH_2OCH_2C(=O)$—;
$H_2NCH_2CH_2OCH_2C(=O)$—;
$H_2NCH_2CH_2OCH_2CH_2OCH_2C(=O)$—;
$H_3CC(=O)HNCH_2CH_2OCH_2C(=O)$—;
$H_3CC(=O)HNCH_2CH_2OCH_2CH_2OCH_2C(=O)$—;
$H_2NCH_2CH_2N(CH_2CH_2)_2NCH_2C(O)$—;
$H_3CC(=O)HNCH_2CH_2N(CH_2CH_2)_2NCH_2C(O)$—;
$H_3CC(=O)N(CH_2CH_2)_2NCH_2C(O)$—;
$O(CH_2CH_2)_2NCH_2CH_2NHC(O)$—;
$HO_2CCH_2C(CO_2H)(OH)CH_2C(=O)$—;
$HO_2CCH_2C(CH_3)(OH)CH_2C(=O)$—;
2-carboxycyclohexyl-C(=O)—;
2carboxycyclopentyl-C(=O)—;
carbobenzyloxy;
4-methoxy-benzenesulfonyl;
cyclopropylcarbonyl;
cyclobutylcarbonyl;
3-pyridinecarbonyl;
2-pyrazinecarbonyl;
tetrazoleacetyl;
pivaloyl;
methoxyacetyl;
hydroxyproline; and
4-(2-(5,6,7,8-tetrahydronaphthenyl))butyl.

11. The compound of claim 10, wherein -Gly-Xp1- forms a bond cleavable by the matrixin selected from MMP-2, MMP-9, and MMP-14.

12. The compound of claim 10, wherein -Gly-Xp1- forms a bond cleavable by the matrixin selected from MMP-2 and MMP-9.

13. The compound of claim 10, wherein -Gly-Xp1- forms a bond cleavable by the matrixin MMP-14.

14. The compound of claim 10, wherein -Gly-Xp1- forms a bond cleavable by MMP-2, MMP-9, and MMP-14.

15. A compound of Formula (Ia), or a pharmaceutically acceptable salt form thereof, wherein;

$E^{cp}$ is an enzyme cleavable peptide selected from:
Cap-Paa-Xa2-Gly-Leu-Laa-;
Cap-Paa-Xa2-Gly-Hof-Laa-;
Cap-Xa2-Gly-Leu-Laa-;
Cap-Xa2-Gly-Hof-Laa-;
Cap-Paa-Xa2-Gly-Leu-Xp2-Laa-;
Cap-Paa-Xa2-Gly-Hof-Xp2-Laa-;
Cap-Xa2-Gly-Leu-Xp2-Laa-;
Cap-Xa2-Gly-Hof-Xp2-Laa-;
Cap-Gly-Leu-Xp2-Laa-; and
Cap-Gly-Hof-Xp2-Laa-;
wherein-Gly-Leu- and-Gly-Hof-form a bond cleavable by a matrixin;

Paa is a Pro, Hyp, Aze, homo-Pro, or Npa;

Xa2 is an amino acid selected from
Hof, Leu, His, Arg, Gin, Ile, Val, Lys, (R)-Leu, Orn, β-Ala, γ-Abu, Cha, Chg, Dap, Cit, N-methyl-Leu, valerolactam, N,N-dimethyl-Lys, 4-aza-Phe, morpholinylpropyl-Gly, N-methylpiperazinepropyl-Gly, 4-aza-Hof, Ala, Asn, Asp, Aze, Cys, Glu, Gly, Hyp, Irg, Met, Phe, Phe(4-fluoro), Pro, Sar, Ser, Thr, Trp, Tyr, Cya, Hca, and Spa;

Xp2 is an amino acid selected from Tyr; Ala; Ser; Leu; Gin; Val, Glu, His; Lys; Arg; Orn; Aze; Hof; homo-Tyr, Cit; 4-aza-Phe; N,N-dimethyl-Lys; Dab; Dap; Asn, Asp, Aze, Cha, Cys, Gly, Hyp, Ile, Irg, Met, Phe, Phe(4-fluoro), Pro, Sar, Thr, Trp, Cya, Hca, Spa, morpholinylpropyl-Gly; O-(4-pyridylmethyl)-Tyr; and N-methylpiperazinepropyl-Gly;

Laa is an amino acid selected from Leu, Cha, Nle, and Hol;

Cap is an N-terminus group selected from R—; Xa4-; and R-Xa4-;

Xa4-is an amino acid selected from Gly, Pro, γ-Glu, and Dmg;

R is selected from: $H_3CC(=O)$—;
$HOC(=O)CH_2CH_2C(=O)$—;
$HOC(=O)CH_2CH_2CH_2C(=Op$;
$HOC(=O)CH_2CH_2CH_2CH_2C(=O)$—;
$H_3COCH2CH_2OCH_2C(=O)$—;
$H_3COCH_2CH_2OCH_2CH_2OCH_2C(=O)$—;
$HO_2CCH_2OCH_2CH_2OCH_2C(=O)$—;
$H_2NCH_2CH_2OCH_2C(=O)$—;
$H_2NCH_2CH_2OCH_2CH_2OCH_2C(=O)$—;
$H_3CC(=O)HNCH_2CH_2OCH_2C(=O)$—;
$H_3CC(=O)HNCH_2CH_2OCH_2CH_2OCH_2C(=O)$—;
$H_2NCH_2CH_2N(CH_2CH_2)_2NCH_2C(O)$—;
$H_3CC(=O)HNCH_2CH_2N(CH_2CH_2)_2NCH_2C(O)$—;
$H_3CC(=O)N(CH_2CH_2)_2NCH_2C(O)$—;
$O(CH_2CH_2)_2NCH_2CH_2NHC(O)$—;
$HO_2CCH_2C(CO_2H)(OH)CH_2C(=O)$—;
$HO_2CCH_2C(CH_3)(OH)CH_2C(=O)$—;
2-carboxycyclohexyl-$C(=O)$—;
2-carboxycyclopentyl-$C(=O)$—;
carbobenzyloxy;
4-methoxy-benzenesulfonyl;
cyclopropylcarbonyl;
cyclobutylcarbonyl;
3-pyridinecarbonyl;
2-pyrazinecarbonyl;
tetrazoleacetyl;
pivaloyl;
methoxyacetyl;
hydroxyproline; and
4-(2-(5,6,7,8-tetrahydronaphthenyl))butyl.

16. The compound of claim 15, wherein -Gly-Leu- and -Gly-Hof- form a bond cleavable by the matrixin selected from MMP-2, MMP-9, and MMP-14.

17. The compound of claim 15, wherein -Gly-Leu- and -Gly-Hof- form a bond cleavable by the matrixin selected from MMP-2 and MMP-9.

18. The compound of claim 15, wherein -Gly-Leu- and -Gly-Hof- form a bond cleavable by the matrixin MMP-14.

19. The compound of claim 15, wherein -Gly-Leu- and -Gly-Hof- form a bond cleavable by MMP-2, MMP-9, and MMP-14.

20. A compound of claim 15 of Formula (Ia), or a pharmaceutically acceptable salt form thereof, wherein;

$E^{cp}$ is an enzyme cleavable peptide selected from:
Cap-Paa-Xa2-Gly-Leu-Leu-;
Cap-Paa-Xa2-Gly-Leu-Cha-;
Cap-Paa-Xa2-Gly-Leu —Nle-;
Cap-Paa-Xa2-Gly-Leu-Hol-;
Cap-Paa-Xa2-Gly-Hof-Leu-;
Cap-Paa-Xa2-Gly-Hof-Cha-;
Cap-Paa-Xa2-Gly-Hof-Nle-;
Cap-Paa-Xa2-Gly-Hof-Hol-;
Cap-Paa-Xa2-Gly-Leu-Xp2-Leu-;
Cap-Paa-Xa2-Gly-Leu-Xp2-Cha-;
Cap-Paa-Xa2-Gly-Leu-Xp2-Nle-;
Cap-Paa-Xa2-Gly-Leu-Xp2-Hol-;
Cap-Paa-Xa2-Gly-Hof-Xp2-Leu-;
Cap-Paa-Xa2-Gly-Hof-Xp2-Cha-;
Cap-Paa-Xa2-Gly-Hof-Xp2-Nle-; and
Cap-Paa-Xa2-Gly-Hof-Xp2-Hol-;
wherein-Gly-Leu- and-Gly-Hof-form a bond cleavable by a matrixin;

Paa is a Pro, Hyp, Aze, homo-Pro, or Npa;

Xa2 is an amino acid selected from
Hof, Leu, His, Arg, Gin, Ile, Val, Lys, (R)-Leu, Om, β-Ala, γ-Abu, Cha, Chg, Dap, Cit, N-methyl-Leu, valerolactam, N,N-dimethyl-Lys, 4-aza-Phe, morpholinylpropyl-Gly, N-methylpiperazinepropyl-Gly, 4-aza-Hof, Ala, Asn, Asp, Aze, Cys, Glu, Gly, Hyp, Irg, Met, Phe, Phe(4-fluoro), Pro, Sar, Ser, Thr, Trp, and Tyr;

Xp2 is an amino acid selected from Tyr; Ala; Ser; Leu; Gin; Val; Glu, His; Lys; Arg; Orn; Aze; Hof; homo-Tyr; Cit; 4-aza-Phe; N,N-dimethyl-Lys; Dab; Dap; Asn, Asp, Aze, Cha, Cys, Gly, Hyp, Ile, Irg, Met, Phe, Phe(4-fluoro), Pro, Sar, Thr, Trp; morpholinylpropyl-Gly; O-(4-pyridylmethyl)-Tyr; and N-methylpiperazinepropyl-Gly;

Cap is an N-terminus group selected from R—; Xa4-; and R-Xa4-;

Xa4- is an amino acid selected from Gly, Pro, γ-Glu, and Dmg;

R is selected from: $H_3CC(=O)$—;
$HOC(=O)CH_2CH_2C(=O)$—;
$HOC(=O)CH_2CH_2CH_2C(=O)$—;
$HOC(=O)CH_2CH_2CH_2CH_2C(=O)$—;
$H_3COCH_2CH_2OCH_2C(=O)$—;
$H_3COCH_2CH_2OCH_2CH_2OCH_2C(=O)$—;
2-carboxycyclohexyl-$C(=O)$—;
2-carboxycyclopentyl-$C(=O)$—; and
tetrazoleacetyl.

21. The compound of claim 20, wherein -Gly-Leu- and -Gly-Hof- form a bond cleavable by the matrixin selected from MMP-2, MMP-9, and MMP-14.

22. The compound of claim 20, wherein -Gly-Leu- and -Gly-Hof- form a bond cleavable by the matrixin selected from MMP-2 and MMP-9.

23. The compound of claim 20, wherein -Gly-Leu- and -Gly-Hof- form a bond cleavable by the matrixin MMP-14.

24. The compound of claim 20, wherein -Gly-Leu- and -Gly-Hof- form a bond cleavable by MMP-2, MMP-9, and MMP-14.

25. A compound of claim 15 of Formula (Ia), or a pharmaceutically acceptable salt form thereof, wherein;

$E^{cp}$ is an enzyme cleavable peptide selected from:
Cap-Xa2-Gly-Leu-Leu-;
Cap-Xa2-Gly-Leu-Cha-;
Cap-Xa2-Gly-Leu-Nle-;
Cap-Xa2-Gly-Leu-Hol-;
Cap-Xa2-Gly-Hof-Leu-;
Cap-Xa2-Gly-Hof-Cha-;
Cap-Xa2-Gly-Hof-Nle-;
Cap-Xa2-Gly-Hof-Hol-;
Cap-Xa2-Gly-Leu-Xp2-Leu-;
Cap-Xa2-Gly-Leu-Xp2-Cha-;
Cap-Xa2-Gly-Leu-Xp2-Nle-;
Cap-Xa2-Gly-Leu-Xp2-Hol-;
Cap-Xa2-Gly-Hof-Xp2-Leu-;
Cap-Xa2-Gly-Hof-Xp2-Cha-;
Cap-Xa2-Gly-Hof-Xp2-Nle-; and
Cap-Xa2-Gly-Hof-Xp2-Hol-;
wherein -Gly-Leu- and -Gly-Hof- form a bond cleavable by a matrixin;

Xa2 is an amino acid selected from
Hof, Leu, His, Arg, Gln, Ile, Val, Lys, (R)-Leu, Orn, β-Ala, γ-Abu, Cha, Chg, Dap, Cit, N-methyl-Leu, valerolactam, N,N-dimethyl-Lys, 4-aza-Phe, morpholinylpropyl-Gly, N-methylpiperazinepropyl-Gly, 4-aza-Hof, Ala, Asn, Asp, Aze, Cys, Glu, Gly, Hyp, Irg, Met, Phe, Phe(4-fluoro), Pro, Sar, Ser, Thr, Trp, and Tyr;

Xp2 is an amino acid selected from Tyr; Ala; Ser, Leu; Gln; Val; Glu, His; Lys; Arg; Orn; Aze; Hof; homo-Tyr; Cit; 4-aza-Phe; N,N-dimethyl-Lys; Dab; Dap; Asn, Asp, Aze, Cha, Cys, Gly, Hyp, Ile, Irg, Met, Phe, Phe(4-fluoro), Pro, Sar, Thr, Trp; morpholinylpropyl-Gly; O-(4-pyridylmethyl)-Tyr; and N-methylpiperazinepropyl-Gly;

Cap is an N-terminus group selected from R—; Xa4-; and R-Xa4-;

Xa4- is an amino acid selected from Gly, Pro, γ-Glu, and Dmg;

R is selected from: $H_3CC(=O)$—;
$HOC(=O)CH_2CH_2C(=O)$—;
$HOC(=O)CH_2CH_2CH_2C(=O)$—;
$HOC(=O)CH_2CH_2CH_2CH_2C(=O)$—;
$H_3COCH_2CH_2OCH_2C(=O)$—;
$H_3COCH_2CH_2OCH_2CH_2OCH_2C(=O)$—;
2-carboxycyclohexyl-$C(=O)$—;
2-carboxycyclopentyl-$C(=O)$—; and
tetrazoleacetyl.

26. The compound of claim 25, wherein -Gly-Leu- and -Gly-Hof- form a bond cleavable by the matrixin selected from MMP-2, MMP-9, and MMP-14.

27. The compound of claim 25, wherein -Gly-Leu- and -Gly-Hof- form a bond cleavable by the matrixin selected from MMP-2 and MMP-9.

28. The compound of claim 25, wherein -Gly-Leu- and -Gly-Hof- form a bond cleavable by the matrixin MMP-14.

29. The compound of claim 25, wherein -Gly-Leu- and -Gly-Hof- form a bond cleavable by MMP-2, MMP-9, and MMP-14.

30. A pharmaceutical composition comprising a compound of claim 1 and a pharmaceutically acceptable carrier.

31. A method of treating a mammal afflicted with a cancer comprising administering to a mammal afflicted with a cancer a therapeutically effective amount of a compound of claim 1.

32. The method of claim 31 wherein the cancer is a breast, ovarian, brain, stomach, lung, colon, prostate or liver cancer or wherein the cancer is a leukemia, lymphoma, carcinoma, sarcoma, or melanoma.

33. A method of delivering a compound to the cells of a mammal afflicted with a cancer comprising contacting the cells of a mammal afflicted with a cancer with a compound of claim 1, wherein the contacting is in the presence of a peptidase comprising a matrixin.

34. The method of claim 33, wherein the cancer is a breast, ovarian, brain, stomach, lung, colon, prostate or liver cancer or wherein the cancer is a leukemia, lymphoma, carcinoma, sarcoma, or melanoma.

35. A compound of claim 4 of Formula (I), or a pharmaceutically acceptable salt form thereof, wherein;

$E^{cp}$ is an enzyme cleavable peptide selected from:
R-γ-E-P-L-G-(O-benzyl-S)—Y-L-;
(SEQ ID NO: 186)

R is selected from: $H_3CC(=O)$—;
$HOC(=O)$—$(CH2)_vC(=O)$—;
wherein v is 1, 2, 3, 4, 5, or 6;
$H_3CO$—$(CH_2CH_2O)_t$—$CH_2C(=O)$—;
$HO_2CCH_2O$—$(CH_2CH_2O)_tCH_2C(=O)$—;
$H_2N$—$(CH_2CH_2O)_tCH_2C(=O)$—; and
$H_3CC(=O)HN$—$(CH_2CH_2O)_t$-$CH_2C(=O)$—;
wherein t is 1, 2, 3, or 4;
$R^1$—$C(=O)$—;
$R^1$—$S(=O)_2$—;
$R^1$—$NHC(=Oy$;
$R^{1a}$-$CH_2C(=O)$—;
proline substituted with —$OR^3$;
$C_1$-$C_4$ alkyl substituted with 0–1 $R^4$; and
2-carboxyphenyl-$C(=O)$—;

$R^1$ is $C_3$-$C_6$ cycloalkyl substituted with 0, 1, or 2 substituents selected from —OH, methoxy and —$CO_2H$;
5–6 membered heterocycle; said heterocycle being saturated, partially saturated or unsaturated; said heterocycle containing 1, 2, 3, or 4 heteroatoms selected from N, O, and S; said heterocycle optionally substituted with 1 or 2-OH, methoxy or —$CO_2H$;
phenyl substituted with 0, 1, or 2 substituents selected from —OH, methoxy and —$CO_2H$; or
$C_1$-$C_6$ alkyl substituted with O-4 $R^{1a}$;

$R^{1a}$ is —OH, $C_1$-$C_3$ alkyl, $C_1$-$C_4$ alkoxy, —$CO_2H$, —$N(CH_2CH_2)_2N$—$R^2$, —$SO_3H$;
$C_3$-$C_6$ cycloalkyl substituted with 0, 1, or 2 substituents selected from methoxy and —OH;
5–6 membered heterocycle; said heterocycle being saturated, partially saturated or unsaturated; said heterocycle containing 1, 2, 3, or 4 heteroatoms selected from N, O, and S; said heterocycle optionally substituted with 1 or 2-OH; or phenyl substituted with 0, 1, or 2 substituents selected from methoxy and —OH;

$R^2$ is —H, $H_2N(C_2-C_4$ alkyly, acetyl(H)N($C_2-C_4$ alkyl)-, or acetyl;

$R^3$ is —H, $C_1-C_4$ alkyl, $C_3-C_6$ cycloalkyl, phenyl, or benzyl;

$R^4$ is —OH, $C_1-C_3$ alkyl, $C_1-C_4$ alkoxy, —$CO_2H$, —N($CH_2CH_2$)$_2$N—$R^2$;

$C_3-C_6$ cycloalkyl substituted with 0, 1, or 2 substituents selected from methoxy and —OH;

5–6 membered heterocycle; said heterocycle being saturated, partially saturated or unsaturated; said heterocycle containing 1, 2, 3, or 4 heteroatoms selected from N, O, and S; said heterocycle optionally substituted with 1 or 2-OH; or $C_6-C_{10}$ carbocycle substituted with 0, 1, or 2 substituents selected from methoxy and —OH.

36. A compound of claim 35 of Formula (I), or a pharmaceutically acceptable salt form thereof, wherein;

$E^{cp}$ is an enzyme cleavable-peptide selected from:
R-γ-E-P-L-G-(O-benzyl-S)—Y-L-;
(SEQ ID NO: 186)

R is selected from: $H_3CC(=O)$—;
$HOC(=O)CH_2CH_2C(=O)$—;
$HOC(=O)CH_2CH_2CH_2C(=O)$—;
$HOC(=O)CH_2CH_2CH_2CH_2C(=O)$—;
$H_3COCH_2CH_2OCH_2C(=O)$—;
$H_3COCH_2CH_2OCH_2CH_2OCH_2C(=O)$—;
$HO_2CCH_2OCH_2CH_2OCH_2C(=O)$—;
$H_2NCH_2CH_2OCH_2C(=O)$—;
$H_2NCH_2CH_2OCH_2CH_2OCH_2C(=O)$—;
$H_3CC(=O)HNCH_2CH_2OCH_2C(=O)$—;
$H_3CC(=O)HNCH_2CH_2OCH_2CH_2OCH_2C(=O)$—;
$H_2NCH_2CH_2N(CH_2CH_2)_2NCH_2C(O)$—;
$H_3CC(=O)HNCH_2CH_2N(CH_2CH_2)_2NCH_2C(O)$—;
$H_3CC(=O)N(CH_2CH_2)_2NCH_2C(O)$—;
$O(CH_2CH_2)_2NCH_2CH_2NHC(O)$—;
$HO_2CCH_2C(CO_2H)(OH)CH_2C(=O)$—;
$HO_2CCH_2C(CH_3)(OH)CH_2C(=O)$—;
2-carboxycyclohexyl-C(=O)—;
2-carboxycyclopentyl-C(=O)—;
carbobenzyloxy;
4-methoxy-benzenesulfonyl;
cyclopropylcarbonyl;
cyclobutylcarbonyl;
3-pyridinecarbonyl;
2-pyrazinecarbonyl;
tetrazoleacetyl;
pivaloyl;
methoxyacetyl;
hydroxyproline; and
4-(2-(5,6,7,8-tetrahydronaphthenyl))butyl.

37. A compound of claim 35 of Formula (I), or a pharmaceutically acceptable salt form thereof, wherein;

$E^{cp}$ is an enzyme cleavable peptide selected from:
R-γ-E-P-L-G-(O-benzyl-S)—Y-L-;
(SEQ ID NO: 186)

R is selected from: $H_3CC(=O)$—;
$HOC(=O)CH_2CH_2C(=O)$—;
$HOC(=O)CH_2CH_2CH_2C(=O)$—;
$HOC(=O)CH_2CH_2CH_2CH_2C(=O)$—;
$H_3COCH_2CH_2OCH_2C(=O)$—;
$H_3COCH_2CH_2OCH_2CH_2OCH_2C(=O)$—; and
tetrazoleacetyl.

* * * * *